(12) United States Patent
Jin et al.

(10) Patent No.: US 12,123,880 B2
(45) Date of Patent: *Oct. 22, 2024

(54) METHODS FOR DETECTING AAV

(71) Applicant: Genzyme Corporation, Cambridge, MA (US)

(72) Inventors: Xiaoying Jin, Cambridge, MA (US); Catherine O'Riordan, Cambridge, MA (US); Lin Liu, Cambridge, MA (US); Kate Zhang, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,542

(22) Filed: May 22, 2023

(65) Prior Publication Data

US 2024/0044910 A1 Feb. 8, 2024

Related U.S. Application Data

(62) Division of application No. 16/325,653, filed as application No. PCT/US2017/046814 on Aug. 14, 2017, now Pat. No. 11,698,377.

(Continued)

(51) Int. Cl.
*G01N 33/68* (2006.01)
*C12N 15/86* (2006.01)
(Continued)

(52) U.S. Cl.
CPC ......... *G01N 33/6848* (2013.01); *C12N 15/86* (2013.01); *G01N 30/72* (2013.01);
(Continued)

(58) Field of Classification Search
None
See application file for complete search history.

(56) References Cited

U.S. PATENT DOCUMENTS 6,989,264 B2  1/2006  Atkinson et al.
7,588,772 B2  9/2009  Kay et al.
(Continued)

FOREIGN PATENT DOCUMENTS

CN     1826414 A     8/2006
JP     H-10-502526 A  3/1998
(Continued)

OTHER PUBLICATIONS

"RIPA Buffer" (2021). Brochure For Product Data, located at <https://www.sigmaaldrich.com/GB/en/product/sigma/r0278>, last visited on Nov. 9, 2021, 9 pages.
(Continued)

*Primary Examiner* — Xiaoyun R Xu
(74) *Attorney, Agent, or Firm* — MORRISON & FOERSTER LLP

(57) ABSTRACT

Provided herein are methods for determining the serotype of a virus particle and/or or determining the heterogeneity of a virus particle (e.g., an AAV particle). In other embodiments, the invention provides methods to determine the heterogeneity of AAV particles. In some aspects, the invention provides viral particles (e.g., rAAV particles) with improved stability and/or improved transduction efficiency by increasing the acetylation and/or deamidation of capsid proteins.

21 Claims, 27 Drawing Sheets

Specification includes a Sequence Listing.

Related U.S. Application Data

(60) Provisional application No. 62/375,314, filed on Aug. 15, 2016.

(51) Int. Cl.
    *G01N 30/72*     (2006.01)
    *G01N 30/02*     (2006.01)

(52) U.S. Cl.
    CPC .............. *C12N 2750/14123* (2013.01); *C12N 2750/14143* (2013.01); *G01N 2030/027* (2013.01)

(56) References Cited

U.S. PATENT DOCUMENTS

| | | |
|---|---|---|
| 7,629,322 B2 | 12/2009 | Kleinschmidt et al. |
| 8,137,948 B2 | 3/2012 | Qu et al. |
| 8,283,151 B2 | 10/2012 | Schmidt et al. |
| 9,169,299 B2 | 10/2015 | Lisowski et al. |
| 9,441,244 B2 | 9/2016 | Schaffer et al. |
| 11,698,377 B2 | 7/2023 | Jin et al. |
| 2011/0275529 A1 | 11/2011 | Heilbronn |
| 2012/0066783 A1 | 3/2012 | Kay et al. |
| 2012/0164106 A1 | 3/2012 | Kay et al. |
| 2013/0217789 A1 | 8/2013 | Taylor et al. |
| 2013/0323226 A1 | 12/2013 | Wilson et al. |
| 2014/0017716 A1 | 1/2014 | Anderson et al. |
| 2015/0065562 A1 | 3/2015 | Yazicioglu et al. |
| 2021/0041451 A1 | 2/2021 | Jin et al. |

FOREIGN PATENT DOCUMENTS

| | | |
|---|---|---|
| WO | WO-199600058 A1 | 1/1996 |
| WO | WO-2003042397 A2 | 5/2003 |
| WO | WO-2004027019 A2 | 4/2004 |
| WO | WO-2005005610 A2 | 1/2005 |
| WO | WO-2007046703 A2 | 4/2007 |
| WO | WO-2010093784 A2 | 8/2010 |
| WO | WO-2010148143 A1 | 12/2010 |
| WO | WO-2013158879 A1 | 10/2013 |
| WO | WO-2015114365 A1 | 8/2015 |
| WO | WO-2015137802 A1 | 9/2015 |

OTHER PUBLICATIONS

Ahmadiankia, A.N. et al. (Jul. 1, 2013). "Generation of Helper Plasmids Encoding Mutant Adeno-Associated Virus Type 2 Capsid Proteins with Increased Resistance against Proteasomal Degradation", Iran J Basic Med Sci 16:813-821.

Arnesen, T. et al. (May 19, 2009, e-pub. May 6, 2009). "Proteomics Analyses Reveal The Evolutionary Conservation and Divergence of N-Terminal Acetyltransferases From Yeast and Humans," *Proc Natl Acad Sci USA* 106:8157-8162.

Asokan, A., et al. (Sep. 2006). "Adeno-Associated Virus Type 2 contains an Integrin alpha5beta1 Binding Domain Essential for Viral Cell Entry," *J Virol* 2006. 80(18):8961-8969.

Bark, S.J. et al. (Feb. 1, 2001, e-pub Jan. 31, 2001). "High-Temperature Protein Mass Mapping Using a Thermophilic Protease", *Journal of the American Chemical Society* 123(8):1774-1775.

Bartlett, J.S. et al. (Mar. 2000). "Infectious Entry Pathway of Adeno-Associated Virus and Adeno-Associated Virus Vectors," *J. Virol.* 74(6):2777-2785.

Benevento, M. et al. (Apr. 18, 2014). "Adenovirus Composition, Proteolysis, and Disassembly Studied By in-Depth Qualitative And Quantitative Proteomics," Journal of Biological Chemistry 289(16):11421-11430.

Ben-Saadon, R. et al. (Oct. 1, 2004). "The Tumor Suppressor Protein p16$^{INK4a}$ and the Human Papillomavirus Oncoprotein-58 E7 Are Naturally Occurring Lysine-less Proteins That Are Degraded by the Ubiquitin System," *J Biol Chem* 279(40): 41414-41421.

Bleker, S. et al. (Feb. 2005). "Mutational Analysis of Narrow Pores at The Fivefold Symmetry Axes of Adeno-Associated Virus Type 2 Capsids Reveals a Dual Role in Genome Packaging and Activation of Phospholipase A2 Activity," *J Virol* 79(4): 2528-2540.

Bossis, I. et al. (Jun. 2003). "Cloning of an Avian Adeno-Associated Virus (AAAV) and Generation of Recombinant AAAV Particles," *J. Virol.* 77(12):6799-6810.

Brown, J.L. et al. (Feb. 25, 1976). "Evidence that Approximately Eighty per Cent of the Soluble Proteins from Ehrlich Ascites Cells are $N^\alpha$-Acetylated," *J Biol Chem* 251: 1009-1014.

Calderaro, A. et al.(Oct. 30, 2014). "Matrix-Assisted Laser Desorption/Ionization Time-of-Flight (MALDI-TOF) 5 Mass Spectrometry Applied to Virus Identification", Scientific Reports 4(6803):1-10.

Cheng, K. et al. (Feb. 21, 2013). "MS-H: A Novel Proteomic Approach to Isolate and Type the *E.coli* H Antigen Using Membrane Filtration and Liquid Chromatography-Tandem Mass Spectrometry (LCMS/MS)", Plos One 8(2):e57339, 12 pages.

Coulton, A.T. et al. (Oct. 1, 2010, e-pub. Aug. 31, 2010). "The Recruitment of Acetylated and Unacetylated Tropomyosin to Distinct Actin Polymers Permits the Discrete Regulation of Specific Myosins in Fission Yeast," *J Cell Sci* 123: 3235-3243.

Dimattia, M.A. et al. (Jun. 2012). "Structural Insight Into the Unique Properties of Adeno-Associated Virus Serotype 9," *J Virol* 86(12):6947-6958.

Dong, B. et al.(Feb. 3, 2014). "Proteomics Analysis of Co-Purifying Cellular Proteins Associated with rAAV Vectors", PLoS One 9(2):e86453, 7 pages.

Forte, G.M.A. et al. (May 4, 2011). "N-Terminal Acetylation Inhibits Protein Targeting to the Endoplasmic Reticulum," *PLoS Biology* 9(5)e1001073, 13 pages.

Gao et al. (Sep. 2002, e-pub. Aug. 21, 2002). "Novel Adeno-Associated Viruses From Rhesus Monkeys as Vectors For Human Gene Therapy," *PNAS* 99(18):11854-11859.

Gao, et al. (Jun. 2004). "Clades of Adeno-Associated Viruses Are Widely Disseminated in Human Tissues," *J. Virol.* 78(12):6381-6388.

Gao, G. et al. (May 13, 2003, e-pub. Apr. 25, 2003). "Adeno-Associated Viruses Undergo Substantial Evolution in Primates During Natural Infections," *PNAS* 100(10):6081-6086.

Gautschi, M. et al. (Oct. 2003). "The Yeast $N^\alpha$-Acetyltransferase NatA is Quantitatively Anchored to the Ribosome and Interacts with Nascent Polypeptides," *Mol Cell Biol* 23(20):7403-7414.

Girod, A. et al. (May 2002). "The VP 1 Capsid Protein of Adeno-Associated Virus Type 2 is Carrying a Phospholipase A2 Domain Required For Virus Infectivity," *J Gen Virol.* 83(Pt 5):973-978.

Hershko, A. et al. (Nov. 1984). "Role of the α-Amino Group of Protein in Ubiquitin-Mediated Protein Breakdown," *Proc Natl Acad Sci USA* 81:7021-7025.

Hwang, C.S. et al. (Feb. 19, 2010, e-pub. Jan. 28, 2010). "N-Terminal Acetylation of Cellular Proteins Creates Specific Degradation Signals," *Science* 327(5968):973-977.

Jornvall, H. (Nov. 1975). "Acetylation of Protein N-Terminal Amino Groups Structural Observations on Alpha-Amino Acetylated Proteins," *J Theor Biol* 55(1):1-12.

Kashiwakura, Y. et al. (Jan. 2005). "Hepatocyte Growth Factor Receptor is a Co-receptor for Adeno-Associated Virus Type 2 Infection," *J Virol.* 79(1):609-614.

Kern, A. et al. (Oct. 2003). "Identification of a Heparin-Binding Motif on Adeno-Associated Virus Type 2 Capsids," *J Virol.* 77(20):11072-11081.

Konietzny, R. et al. (May 2012). "Detection of BK Virus In Urine From Renal Transplant Subjects By Mass Spectrometry", Clinical Proteomics 9(4):1-9, 10 pages.

Kronenberg, S. et al. (May 2005). "A Conformational Change in the Adeno-Associated Virus Type 2 Capsid Leads to the Exposure of Hidden VP1 N Termini," *J Virol* 79(9):5296-5303.

Majchrzykiewicz-Koehorst, J.A. et al. (Mar. 1, 2015, e-pub. Dec. 8, 2014). "Rapid and Generic Identification of Influenza A and other Respiratory Viruses with Mass Spectrometry", *Journal of Virological Methods* 213:75-83.

Micromass UK Limited. (not dated). "Quattro LC User's Guide", PDF located at <https://www.waters.com/webassets/cms/support/docs/quattro_lc_guide_issue2.pdf>, last visited on Nov. 9, 2021, 164 pages.

(56) References Cited

OTHER PUBLICATIONS

Murray, S. et al (May 26, 2006). "Characterization of the Capsid Protein Glycosylation of Adeno-Associated Virus Type 2 by High-Resolution Mass Spectrometry", *Journal of Virology.* 80(12):6171-6176.

Nam, H.J. et al. (Nov. 2007, e-pub. Aug. 29, 2007). "Structure of Adeno-Associated Virus Serotype 8, a Gene Therapy Vector," *J Virol.* 81(22):12260-12271.

Notice of Opposition for European Patent No. 3497207, dated Jan. 6, 2021, Proprietor Genzyme Corporation, Opponent Definition IP Limited, 39 pages.

Notice of Opposition for European Patent No. 3497207, dated Jan. 6, 2021, Proprietor Genzyme Corporation, Opponent Definition IP Limited, 13 pages.

Opie, S.R. et al. (Jun. 2003). "Identification of Amino Acid Residues in the Capsid Proteins of Adeno-Associated Virus Type 2 That Contribute to Heparan Sulfate Proteoglycan Binding," *J. Virol.* 77(12):6995-7006.

Perry, R.H. et al. (Nov.-Dec. 2008). "Orbitrap Mass Spectrometry: Instrumentation, Ion Motion and Applications," *Mass. Spectrom. Rev.* 27(6):661-699.

Persson, B. et al. (Nov. 4, 1985). "Structures of N-Terminally Acetylated Proteins," *Eur J Biochem* 152:523-527.

Pestana, A. et al. (Apr. 8, 1975). "Acetylation of Nascent Polypeptide Chains on Rat Liver Polyribosomes In Vivo and In Vitro," *Biochemistry* 14(7):1404-1412.

Pierson, E.E. et al. (Jul. 5, 2016). "Resolving Adeno-Associated Viral Particle Diversity With Charge Detection Mass Spectrometry," *Analytical Chemistry* 88:6718-6725.

Plumb, R. et al. (2004). "Ultra-Performance Liquid Chromatography Coupled to Quadrupole-Orthogonal Time-of-Flight Mass Spectrometry," *Rapid Commun. Mass Spectrom.* 18(19):2331-2337.

Polevoda, B. et al. (Aug. 15, 2003, e-pub. Jun. 3, 2003). "Nat3p and Mdm20p are Required for Function of Yeast NatB Nα-Terminal Acetyltransferase and of Actin and Tropomyosin," *J Biol Chem* 278(33):30686-30697.

Popa-Wagner, R. et al. (Sep. 2012). "Impact of VP1-Specific Protein Sequence Motifs on Adeno-Associated virus type 2 Intracellular Trafficking and Nuclear Entry," *J Virol.* 86(17):9163-9174.

Qing, K. et al. (Jan. 1999). "Human Fibroblast Growth Factor Receptor 1 is a Co-Receptor For Infection By Adeno-Associated Virus 2," *Nat Med.* 5(1):71-77.

Qu et al. (Mar. 2007, e-pub. Dec. 28, 2006). "Separation of Adeno-Associated Virus Type 2 Empty Particles From Genome Containing Vectors By Anion-Exchange Column Chromatography," *J. Virol. Methods* 140(1-2):183-192.

Rabinowitz, J.E. et al. (Jan. 2002). "Cross-Packaging of a Single Adeno-Associated Virus (AAV) Type 2 Vector Genome into Multiple AAV Serotypes Enables Transduction with Broad Specificity," *J. Virol.* 76(2):791-801.

Salganik, M. et al. (Nov. 2012). "Evidence for pH-Dependent Protease Activity in the Adeno-Associated Virus Capsid," *J Virol.* 86(21):11877-11885.

Sanlioglu, S. et al. (Oct. 2000). "Endocytosis and Nuclear Trafficking of Adeno-Associated Virus Type 2 Are Controlled By Rac 1 and Phosphatidylinositol-3 Kinase Activation," *J. Virol.* 74(19):9184-9196.

Scheltema, R.A. et al. (Dec. 2014, e-pub. Oct. 30, 2014). "The Q Exactive HF, a Benchtop Mass Spectrometer with a Pre-filter, High-performance Quadrupole and an Ultra-high-field Orbitrap Analyzer," *Mol. Cell Proteomics* 13(12):3698-3708.

Scigelova, M. et al. (Jul. 2011, May 9, 2011). "Fourier Transform Mass Spectrometry," *Mol. Cell Proteomics* 10(7):M111.009431, 19 pages.

She, Y-M. et al. (Jun. 8, 2001). "Determination of the Complete Amino Acid Sequence For the Coat Protein of Brome Mosaic Virus By Time-of-Flight Mass Spectrometry", Journal of Biological Chemistry 276(23):20039-20047.

Snijder, J. et al. (May 1, 2014). "Defining the Stoichiometry and Cargo Load of Viral and Bacterial Nanoparticles by Orbitrap Mass Spectrometry," *J. Am. Chem. Soc.* 136: 7295-7299.

Sonntag, F. et al. (Nov. 2006). "Adeno-associated virus type 2 capsids with externalized VP1/VP2 trafficking domains are generated prior to passage through the cytoplasm and are maintained until uncoating occurs in the nucleus," *J Virol.* 80(22):11040-11054.

Stahnke, S. et al. (Jan. 5, 2011, e-pub. Oct. 25, 2010). "Intrinsic Phospholipase A2 Activity of Adeno-Associated Virus is Involved in Endosomal Escape of Incoming Particles," *Virology* 409(1):77-83.

Strobel, B. et al. (Jul. 28, 2015). "Comparative Analysis of Cesium Chloride- and Iodixanol-Based Purification of Recombinant Adeno-Associated Viral Vectors for Preclinical Applications", Human Gene Therapy Methods 26(4):147-157.

Submission in Opposition Proceedings for European Patent No. 3497207, dated Feb. 25, 2022, Proprietor Genzyme Corporation, Opponent Definition IP Limited, 2 pages.

Summerford, C. (Feb. 1998). "Membrane-Associated Heparan Sulfate Proteoglycan is a Receptor for Adeno-Associated Virus Type 2 Virions," *J. Virol.* 72(2):1438-1445.

Summerford, C. (Jan. 1999). "aVB5 Integrin: A Co-Receptor For Adeno-Associated Virus Type 2 Infection," *Nat Med* 5(1):78-82.

Tan, S. et al.(2000). "Rapid Simultaneous Detection of Two Orchid Viruses Using LC- and/or MALDI-mass Spectrometry", Journal of Virological Methods 85:93-99.

Team TFS (Jul. 22, 2016). "Liquid Chromatography as the Future Replacement for Gel Electrophoresis", a website article available at URL:<https://www.analyteguru.com/t5/Blog/Liquid-Chromatography-as-10 the-Future-Replacement-for-Gel/ba-p/3171>, last visited on Nov. 9, 2021, 9 pages.

Thomas, J.J. et al. (Sep. 15, 1998). "Viral Characterization by Direct Analysis of Capsid Proteins," *Anal Chem.* 70(18):3863-3867.

Van Vliet, K. et al. (Aug. 1, 2009, e-pub. Mar. 26, 2009). "Adeno-Associated Virus Capsid Serotype Identification: Analytical Methods Development and Application", *Journal of Virological Methods* 159(2):167-177.

Wang, L. et al. (Jun. 2001). "Detecting Structural Changes in Viral Capsids by Hydrogen Exchange and Mass Spectrometry," *Protein Sci.* 10(6):1234-1243.

Waters (The Science of What's Possible) (Copyright Date 2021). "Beginner's Guide to UPLC", Introduction, a website article located at: <https://www.waters.com/waters/en US/UPLC---Ultra-Performance-Liguid-Chromatography-Beginner%27s-Guide/nav.htm?cid=134803622 &1ocale=en US>, last visited on Nov. 9, 2021, 2 pages.

Xiao, X. et al. (Mar. 1998). "Production of High-Titer Recombinant Adeno-Associated Virus Vectors in the Absence of Helper Adenovirus," *Journal of Virology* 72(3):2224-2232.

Xiaoying, J. et al. (Oct. 2017, Jun. 16, 2017). "Direct Liquid Chromatography/Mass Spectrometry Analysis for Complete Characterization of Recombinant Adeno-Associated Virus Capsid Proteins," *Human Gene Therapy Methods* 28(5):255-267.

Xie, Q. et al. (Aug. 6, 2002). "The Atomic Structure of Adeno-Associated Virus (AAV-2), a Vector for Human Gene Therapy," *PNAS USA* 99(16):10405-10410.

Yamashita, M. et al. (1984). "Electrospray Ion Source. Another Variation on the Free-Jet Theme," *J. Phys. Chem.* 88(20):4451-4459.

Yan, Z. et al. (Mar. 2002). "Ubiquitination of both Adeno-Associated Virus Type 2 and 5 Capsid Proteins Affects the Transduction Efficiency of Recombinant Vectors," *J Virol.* 76(5):2043-2053.

Zhao, W. et al. (Sep. 30, 2006, e-pub. Jul. 10, 2006). "Role of Cellular FKBP52 Protein in Intracellular Trafficking of Recombinant Adeno-associated Virus 2 Vectors," *Virology* 353(2):283-293.

Zhong, L. et al. (Jun. 3, 2008, May 29, 2008). "Next Generation of Adeno-Associated Virus 2 Vectors: Point Mutations in Tyrosines Lead to High-Efficiency Transduction at Lower Doses," *Proc Natl Acad Sci USA* 105(22):7827-7832.

1   MAADGYLPDWLEDTLSEGIRQWWKLKPGPPPPKPAERHKDDSRGLVLPGY   50

51  KYLGPFNGLDKGEPVNEADAAALEHDKAYDRQLDSGDNPYLKYNHADAEF   100

101 QERLKEDTSFGGNLGRAVFQAKKRVLEPLGLVEEPVKTAPGKKRPVEHSP   150

151 VEPDSSSGTGKAGQQPARKRLNFGQTGDADSVPDPQPLGQPPAAPSGLGT   200

201 NTMATGSGAPMADNNEGADGVGNSSGNWHCDSTWMGDRVITTSTRTWALP   250

251 TYNNHLYKQISSQSGASNDNHYFGYSTPWGYFDFNRFHCHFSPRDWQRLI   300

301 NNNWGFRPKRLNFKLFNIQVKEVTQNDGTTTIANNLTSTVQVFTDSEYQL   350

351 PYVLGSAHQGCLPPFPADVFMVPQYGYLTLNNGSQAVGRSSFYCLEYFPS   400

401 QMLRTGNNFTFSYTFEDVPFHSSYAHSQSLDRLMNPLIDQYLYYLSRTNT   450

451 PSGTTTQSRLQFSQAGASDIRDQSRNWLPGPCYRQQRVSKTSADNNNSEY   500

501 SWTGATKYHLNGRDSLVNPGPAMASHKDDEEKFPPQSGVLIFGKQGSEKT   550

551 NVDIEKVMITDEEEIRTTNPVATEQYGSVSTNLQRGNRQAATADVNTQGV   600

601 LPGMVWQDRDVYLQGPIWAKIPHTDGHFHPSPLMGGFGLKHPPPQILIKN   650

651 TPVPANPSTTFSAAKFASFITQYSTGQVSVEIEWELQKENSKRWNPEIQY   700

701 TSNYNKSVNVDFTVDTNGVYSEPRPIGTRYLTRNL                 735

Deacetylation AAV5 Mutant Vectors

| Lane | Sample |
|---|---|
| 1 | Mark12 Marker |
| 2 | deAC-AAV5 (S2G)/CBA-eGFP X17052C |
| 3 | deAC-AAV5 (S2L)/CBA-eGFP X17052D |
| 4 | deAC-AAV5 (S2GVP3)/CBA-eGFP X17058D |
| 5 | deAC-AAV5 (S2LVP3)/CBA-eGFP X17065A |
| 6 | deAC-AAV5 (S2PVP1VP3)/CBA-eGFP X17065B |
| 7 | deAC-AAV5 (S2GVP1VP3)/CBA-eGFP X17065C |
| 8 | deAC-AAV5 (S2PVP3)/CBA-eGFP X17065D |
| 9 | deAC-AAV5 (S2P)/CBA-eGFP X17065E |
| 10 | deAC-AAV5 (S2LVP1VP3)/CBA-eGFP X17072B |

(~1E10 VGs/Lane)

FIG. 9

Deamidation of N57(G)

| | % Deamidation on N57 | replicate |
|---|---|---|
| AAV2(A35N) | 17.8 | 1 |
| AAV2(G58D) | 1.1 | 1 |
| AAV2 control | 5.7 | 2 |

AAV2(A35N) has been stored at 4C for 1 months

FIG. 15

METHODS FOR DETECTING AAV

CROSS REFERENCE TO RELATED APPLICATIONS

This application is a divisional application of U.S. patent application Ser. No. 16/325,653, which adopts the international filing date of Aug. 14, 2017, which is a National Phase application under 35 U.S.C. § 371 of International Application No. PCT/US2017/046814, filed Aug. 14, 2017, which claims the priority benefit of U.S. Provisional Application No. 62/375,314, filed Aug. 15, 2016, the disclosure of each of which is hereby incorporated by reference in its entirety.

REFERENCE TO AN ELECTRONIC SEQUENCE LISTING

The contents of the electronic Sequence Listing 159792014110SEQLIST.xml; Size 56,201 bytes, and date of creation: May 18, 2023) is herein incorporated by reference in its entirety.

FIELD OF THE INVENTION

The present invention relates to methods for serotyping and/or determining the heterogeneity of a viral particle (e.g., an adeno-associated virus (AAV) particle) using mass determination, e.g., by employing liquid chromatography/mass spectrometry (LC/MS) or liquid chromatography/mass spectrometry-mass spectrometry (LC/MS/MS). In some aspects, the present invention relates to methods to improve the stability of AAV particles.

BACKGROUND OF THE INVENTION

Complete characterization of the viral capsid proteins of viral vectors (e.g., AAV vectors), including their sequence and post-translation modifications, is desired in gene therapy research and development since viral capsid proteins (VPs) are critical for viral infectivity.

Viral vector products such as recombinant Adeno-Associated Virus (rAAV) products are typically identified using molecular tools targeting the nucleic acid transgene. These methods may include polymerase chain reaction (PCR) targeting transgene-specific sequences and Restriction Fragment Length Polymorphism (RFLP) techniques. As rAAV technologies evolve, many facilities are beginning to investigate multiple AAV capsid serotypes encoding their therapeutic transgene in an effort to improve targeted tissue tropism.

Traditional molecular identification methods identify products containing unique transgenes but are unable to discern those that have differing AAV capsid serotypes. Currently, most AAV serotype identity tests are based on SDS-PAGE banding patterns, an antibody-based ELISA, or a Western blot assay. However, the banding patterns and antibodies are not specific enough to differentiate different AAV serotypes. Gel-LC/MS/MS has been reported as a capsid serotype identification method. However, this method involves multiple steps including SDS-PAGE, in-gel digestion, and LC/MS/MS and thus requires multiple days for the analysis while providing limited sequence coverage. Methods for identifying vectors such as rAAV vectors are of interest to gene therapy vectors (see, e.g., U.S. PG Pub. No. US20110275529). Thus, it would be useful to have improved methods of characterizing viral particles.

All references cited herein, including patent applications and publications, are incorporated by reference in their entirety.

BRIEF SUMMARY OF THE INVENTION

Using rAAV as an example, described herein is the use of LC/MS as an analytical tool to specifically identify different viral capsid serotypes (e.g., rAAV capsid serotypes). As part of viral characterization, LC/MS can be used to augment the molecular identification methods. This analytical combination can satisfy regulatory requirements by discerning both the identity of the product's therapeutic transgene and the identity of the capsid serotype. This method can be used e.g., as an AAV serotype identity test or to monitor viral capsid protein heterogeneity in recombinant AAV gene therapy development. It can also be used to confirm VP sequences in capsid engineering research. In addition, this technique can be used to study the impact of post translation modifications, such as N terminal acetylation of viral capsid proteins, on transfection potency and intracellular protein trafficking.

The methods described herein can also be used to design AAV particles for greater stability and/or improved transduction efficiency; for example by altering the amino acid residue at position 2 of VP1 and/or VP3 of the AAV capsid such that the amino acid at position 2 is acetylated to a higher extent compared to a wild type AAV capsid. In some embodiments, the methods can be used to design AAV particles with reduced transduction efficiency; for example by altering the amino acid residue at position 2 of VP1 and/or VP3 of the AAV capsid such that the amino acid at position 2 is deacetylated to a higher or lower extent compared to a wild type AAV capsid.

In some aspects, the invention provides a method to determine the serotype of a viral particle comprising a) denaturing the viral particle, b) subjecting the denatured viral particle to liquid chromatography/mass spectrometry (LC/MS), and c) determining the masses of one or more capsid proteins of the viral particle; wherein the specific combination of masses of the one or more capsid proteins are indicative of the virus serotype. In some embodiments, the calculated masses of the one or more capsid proteins are compared to the theoretical masses of the one or more capsid proteins of one or more virus serotypes.

In some aspects, the invention provides a method of determining the heterogeneity of a viral particle comprising a) denaturing the viral particle, b) subjecting the denatured viral particle to liquid chromatography/mass spectrometry/mass spectrometry (LC/MS/MS), c) determining the masses of one or more capsid proteins of the viral particle, and d) comparing the masses of step c) with the theoretical masses of the one or more capsid proteins of the virus serotype; wherein a deviation of one or more of the masses of the one or more capsid proteins are indicative of the viral capsid heterogeneity. In some embodiments, the heterogeneity comprises one or more of mixed serotypes, variant capsids, capsid amino acid substitutions, truncated capsids, or modified capsids.

In some embodiments of the above aspects, the liquid chromatography is reverse phase liquid chromatography, size exclusion chromatography, hydrophilic interaction liquid chromatography, or cation exchange chromatography. In some embodiments, the viral particle comprises a viral vector encoding a heterologous transgene.

In some aspects, the invention provide a method to determine the serotype of a viral particle comprising a) denaturing the viral particle, b) subjecting the denatured viral particle to reduction and/or alkylation, c) subjecting the denatured viral particle to digestion to generate fragments of one or more capsid proteins of the viral particle, d) subjecting the fragments of the one or more capsid proteins to liquid chromatography/mass spectrometry-mass spectrometry (LC/MS/MS), and e) determining the masses of fragments of the one or more capsid proteins of the viral particle; wherein the specific combination of masses of fragments of the one or more capsid proteins are indicative of the viral serotype. In some embodiments, the calculated masses of the fragments of the one or more capsid proteins are compared to the theoretical masses of fragments of the one or more capsid proteins of one or more viral serotypes.

In some aspects, the invention provides a method of determining the heterogeneity of a serotype of a viral particle comprising a) denaturing the viral particle, b) subjecting the denatured viral particle to reduction and/or alkylation, c) subjecting the denatured viral particle to digestion to generate fragments of one or more capsid proteins of the viral particle, d) subjecting the fragments of the one or more capsid proteins to liquid chromatography/mass spectrometry-mass spectrometry (LC/MS/MS), e) determining the masses of fragments of the one or more capsid proteins of the viral particle, and f) comparing the masses of step e) with the theoretical masses of fragments of the one or more capsid proteins of the viral serotype; wherein a deviation of one or more of the masses of the one or more capsid proteins are indicative of the viral capsid heterogeneity. In some embodiments, the heterogeneity comprises one or more of mixed serotypes, variant capsids, capsid amino acid substitutions, truncated capsids, or modified capsids. In some embodiments, the liquid chromatography is reverse phase liquid chromatography, size exclusion chromatography, hydrophilic interaction liquid chromatography, or cation exchange chromatography.

As shown herein the methods can be performed in the absence of a gel separation step (e.g., sodium dodecyl sulfate polyacrylamide gel electrophoresis (SDS-PAGE)).

In some embodiments of the above aspects and embodiments, the viral particle comprises a viral vector encoding a heterologous transgene. In some embodiments, the viral particle belongs to a viral family selected from the group consisting of Adenoviridae, Parvoviridae, Retroviridae, Baculoviridae, and Herpesviridae. In some embodiments, the viral particle belongs to a viral genus selected from the group consisting of *Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus*, and *Rhadinovirus*.

In some aspects, the invention provides a method to determine the serotype of an adeno-associated virus (AAV) particle comprising a) denaturing the AAV particle, b) subjecting the denatured AAV particle to liquid chromatography/mass spectrometry (LC/MS), and c) determining the masses of VP1, VP2 and VP3 of the AAV particle; wherein the specific combination of masses of VP1, VP2 and VP3 are indicative of the AAV serotype. In some embodiments, the calculated masses of VP1, VP2 and VP3 are compared to the theoretical masses of VP1, VP2 and VP3 of one or more AAV serotypes.

In some aspects, the invention provides a method of determining the heterogeneity of an AAV particle comprising a) denaturing the AAV particle, b) subjecting the denatured AAV particle to liquid chromatography/mass spectrometry/mass spectrometry (LC/MS/MS), c) determining the masses of VP1, VP2 and VP3 of the AAV particle, and d) comparing the masses of step c) with the theoretical masses of VP1, VP2 and VP3 of the AAV serotype; wherein a deviation of one or more of the masses of VP1, VP2 or VP3 are indicative of the AAV capsid heterogeneity. In some embodiments, the heterogeneity comprises one or more of mixed serotypes, variant capsids, capsid amino acid substitutions, truncated capsids, or modified capsids.

In some embodiments of the above aspects and embodiments, the AAV particle is denatured with acetic acid, guanidine hydrochloride and/or an organic solvent. In some embodiments, the liquid chromatography is reverse phase liquid chromatography, size exclusion chromatography, hydrophilic interaction liquid chromatography, or cation exchange chromatography. In some embodiments, the liquid chromatography is reverse phase liquid chromatography. In some embodiments, the reverse phase chromatography is a C4 or C8 reverse chromatography. In some embodiments, the chromatography uses a mobile phase A comprising formic acid in water. In some embodiments, the mobile phase A comprises about 0.1% formic acid. In some embodiments, the chromatography comprises a mobile phase B comprising formic acid in acetonitrile. In some embodiments, the mobile phase B comprises about 0.1% formic acid. In some embodiments, the proportion of mobile phase B in the chromatography increases over time. In some embodiments, the proportion of mobile phase B in the chromatography increases in a stepwise manner. In some embodiments, mobile phase B increases from about 10% to about 20%, from about 20% to about 30%, and from about 30% to about 38%. In some embodiments, mobile phase B increases from about 10% to about 20% in about 6 minutes, from about 20% to about 30% in about 10 minutes, and from about 30% to about 38% in about 40 minutes. In some embodiments, the liquid chromatography is ultra-performance liquid chromatography (UPLC).

In some embodiments of the above aspects and embodiments, the mass spectrometry comprises a capillary voltage of about 3.5 kV. In some embodiments, the mass spectrometry comprises a sampling cone voltage of about 45 V. In some embodiments, the mass spectrometry comprises assisted calibration. In some embodiments, sodium iodide is used as a calibrant.

In some embodiments of the above aspects and embodiments, the N-terminus of VP1 and/or VP3 is acetylated. In some embodiments, the AAV particle is a recombinant AAV (rAAV) particle. In some embodiments, the AAV particle comprises an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV LK03 capsid, an AAV2R471A capsid, an AAV2/2-7m8 capsid, an AAV DJ capsid, an AAV DJ8 capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1). In some embodiments, the AAV capsid comprises a tyrosine mutation or a heparin binding mutation. In some embodiments, the masses of VP1, VP2, and VP3 are compared to the theoretical masses of one or more of AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV LK03 capsid, an AAV2R471A capsid, an AAV2/2-7m8 capsid, an AAV DJ capsid, an AAV DJ8 capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1), an AAV2HBKO capsid, an AAVPHP.B capsid or an AAVPHP.eB capsid.

In some embodiments of the above aspects and embodiments, the viral particle comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11 ITR, or an AAV12 ITR. In some embodiments, the AAV particle comprises an AAV vector encoding a heterologous transgene.

In some aspects, the invention provides a method to determine the serotype of an adeno-associated virus (AAV) particle comprising a) denaturing the AAV particle, b) subjecting the denatured AAV particle to reduction and/or alkylation, c) subjecting the denatured AAV particle to digestion to generate fragments of VP1, VP2 and/or VP3 of the AAV particle, d) subjecting the fragments of VP1, VP2 and/or VP3 to liquid chromatography/mass spectrometry-mass spectrometry (LC/MS/MS), and e) determining the masses of fragments of VP1, VP2 and VP3 of the AAV particle; wherein the specific combination of masses of fragments of VP1, VP2 and VP3 are indicative of the AAV serotype. In some embodiments, the calculated masses of the fragments of VP1, VP2 and/or VP3 are compared to the theoretical masses of fragments of VP1, VP2 and/or VP3 of one or more AAV serotypes.

In some aspects, the invention provides a method of determining the heterogeneity of a serotype of an AAV particle comprising a) denaturing the AAV particle, b) subjecting the denatured AAV particle to reduction and/or alkylation, c) subjecting the denatured AAV particle to digestion to generate fragments of VP1, VP2 and/or VP3 of the AAV particle, d) subjecting the fragments of VP1, VP2 and/or VP3 to liquid chromatography/mass spectrometry-mass spectrometry (LC/MS/MS), e) determining the masses of fragments of VP1, VP2 and VP3 of the AAV particle, and f) comparing the masses of step e) with the theoretical masses of fragments of VP1, VP2 and VP3 of the AAV serotype; wherein a deviation of one or more of the masses of VP1, VP2 or VP3 are indicative of the AAV capsid heterogeneity. In some embodiments, the heterogeneity comprises one or more of mixed serotypes, variant capsids, capsid amino acid substitutions, truncated capsids, or modified capsids. In some embodiments, the reduction is by subjecting the AAV particle to dithiothreitol, beta-mercaptoethanol, or tris(2-carboxyethyl)phosphine (TCEP). In some embodiments, the alkylation is by subjecting the AAV particle to iodoacetic acid, iodoacetamide, or 4-vinylpyridine. In some embodiments, the digestion is an enzymatic digestion or a chemical digestion. In some embodiments, the enzymatic digestion is an endopeptidase digestion. In some embodiments, the enzymatic digestion is a trypsin digestion, a LysC digestion, an Asp-N digestion or a Glu-C digestion. In some embodiments, the chemical digestion is cyanogen bromide digestion or an acid digestion. In some embodiments, the AAV particle is denatured with acetic acid, guanidine hydrochloride and/or an organic solvent.

In some embodiments of the above aspects and embodiments, the liquid chromatography is reverse phase liquid chromatography, size exclusion chromatography, hydrophilic interaction liquid chromatography, or cation exchange chromatography. In some embodiments, the liquid chromatography is reverse phase liquid chromatography. In some embodiments, the reverse phase chromatography is a C18 reverse chromatography. In some embodiments, the chromatography uses a mobile phase A comprising formic acid in water. In some embodiments, the mobile phase A comprises about 0.1% formic acid. In some embodiments, the chromatography comprises a mobile phase B comprising formic acid in acetonitrile. In some embodiments, the mobile phase B comprises about 0.1% formic acid. In some embodiments, the proportion of mobile phase B in the chromatography increases over time. In some embodiments, mobile phase B increases from about 2% to about 60%. In some embodiments, mobile phase B increases from about 2% to about 60% in about 121 minutes. In some embodiments, the liquid chromatography is high-performance liquid chromatography (HPLC).

In some embodiments of the above aspects and embodiments, the mass spectrometry comprises a capillary voltage of about 3.5 kV. In some embodiments, the mass spectrometry comprises a sampling cone voltage of about 45 V. In some embodiments, the mass spectrometry comprises assisted calibration. In some embodiments, sodium iodide is used as a calibrant.

In some embodiments of the above aspects and embodiments, the N-terminus of VP1 and/or VP3 is acetylated. In some embodiments, the AAV particle is a recombinant AAV (rAAV) particle. In some embodiments, the AAV particle comprises an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV LK03 capsid, an AAV2R471A capsid, an AAV2/2-7m8 capsid, an AAV DJ capsid, an AAV DJ8 capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1). In some embodiments, the AAV capsid comprises a tyrosine mutation or a heparin binding mutation. In some embodiments, the masses of VP1, VP2, and VP3 are compared to the theoretical masses of one or more of AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV LK03 capsid, an AAV2R471A capsid, an AAV2/2-7m8 capsid, an AAV DJ capsid, an AAV DJ8 capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1).

In some embodiments of the above aspects and embodiments, the viral particle comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11

ITR, or an AAV12 ITR. In some embodiments, the AAV particle comprises an AAV vector encoding a heterologous transgene.

In some embodiments, the invention provides a recombinant AAV (rAAV) particle comprising an amino acid substitution at amino acid residue 2 of VP1 and/or VP3; wherein the amino acid substitution at amino acid residue 2 of VP1 and/or VP3 alters N-terminal acetylation compared to N-terminal acetylation at amino acid residue 2 of VP1 and/or VP3 of the parent AAV particle. In some embodiments, the substitution results in a higher frequency of N-terminal acetylation or a lower frequency of N-terminal acetylation. In some embodiments, the rAAV particle comprises an amino acid substitution at amino acid residue 2 of VP1; wherein the amino acid substitution at amino acid residue 2 of VP1 alters N-terminal acetylation compared to N-terminal acetylation at amino acid residue 2 of VP1 of the parent AAV particle. In some embodiments, the rAAV particle comprises an amino acid substitution at amino acid residue 2 of VP3; wherein the amino acid substitution at amino acid residue 2 of VP3 alters N-terminal acetylation compared to N-terminal acetylation at amino acid residue 2 of VP3 of the parent AAV particle. In some embodiments, amino acid residue 2 is substituted with Cys, Ser, Thr, Val, Gly, Asn, Asp, Glu, Ile, Leu, Phe, Gln, Lys, Met, Pro or Tyr. In some embodiments, amino acid residue 2 is substituted with Ser, Asp or Glu.

In some embodiments of the above aspects and embodiments, the AAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, an AAV DJ8 capsid, AAV2 N587A, AAV2 E548A, AAV2 N708A, AAV V708K, goat AAV, AAV1/AAV2 chimeric, bovine AAV, mouse AAV, rAAV2/HBoV1, AAV2HBKO, AAVPHP.B, or AAVPHP.eB serotype capsid. In some embodiments, the AAV capsid further comprises a tyrosine mutation or a heparin binding mutation. In some embodiments, the rAAV particle comprises a rAAV vector. In some embodiments, the rAAV vector comprises one or more AAV ITRs. In some embodiments, the rAAV vector comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11 ITR, or an AAV12 ITR. In some embodiments, the AAV capsid and the AAV ITRs are derived from the same serotype. In some embodiments, the AAV capsid and the AAV ITRs are derived from different serotypes. In some embodiments, the AAV particle comprises an AAV vector encoding a heterologous transgene flanked by one or more AAV ITRs.

In some embodiments of the above aspects and embodiments, the rAAV vector is a self-complementary vector. In some embodiments, the rAAV vector comprises first nucleic acid sequence encoding the transgene and a second nucleic acid sequence encoding a complement of the transgene, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the rAAV particle is produced by transfecting a host cell with nucleic acid encoding the rAAV vector and nucleic acid encoding AAV rep and cap functions, and providing nucleic acid encoding AAV helper functions. In some embodiments, the AAV helper functions are provided by transfecting the host cell with nucleic acid encoding the AAV helper functions. In some embodiments, the AAV helper functions are provided by infecting the host cell with an AAV helper virus that provides the AAV helper functions. In some embodiments, the AAV helper virus is an adenovirus, a herpes simplex virus or a baculovirus. In some embodiments, the rAAV particle is produced by an AAV producer cell comprising nucleic acid encoding the rAAV vector and nucleic acid encoding AAV rep and cap functions, and providing nucleic acid encoding AAV helper functions. In some embodiments, the AAV producer cell comprises nucleic acid encoding AAV helper functions. In some embodiments, the AAV helper functions are provided by infecting the AAV producer cells with an AAV helper virus that provides the AAV helper functions. In some embodiments, the AAV helper virus is an adenovirus, a herpes simplex virus, or a baculovirus. In some embodiments, the AAV cap functions provide an amino acid substitution at amino acid residue 2 of VP1 and/or VP3, wherein the amino acid substitution at amino acid residue 2 of VP1 and/or VP3 alters N-terminal acetylation compared to N-terminal acetylation at amino acid residue 2 of VP1 and/or VP3 of the parent AAV particle.

In some aspects, the invention provides a pharmaceutical composition comprising the rAAV particle as described herein. In some aspects, the invention provides a kit comprising the rAAV particle or the pharmaceutical composition as described herein. In some aspects, the invention provides an article of manufacture comprising the rAAV particle or the pharmaceutical composition as described herein.

In some aspects, the invention provides as AAV capsid protein comprising an amino acid substitution at amino acid residue 2 of a parent AAV capsid protein; wherein the amino acid substitution at amino acid residue 2 alters N-terminal acetylation compared to N-terminal acetylation at amino acid residue 2 of the parent AAV capsid protein. In some embodiments, the substitution results in a higher frequency of N-terminal acetylation or a lower frequency of N-terminal acetylation. In some embodiments, the AAV capsid protein is VP1 or VP3. In some embodiments, amino acid residue 2 of the AAV capsid protein is substituted with Cys, Ser, Thr, Val, Gly, Asn, Asp, Glu, Ile, Leu, Phe, Gln, Lys, Met, Pro or Tyr. In some embodiments, amino acid residue 2 of the AAV capsid protein is substituted with Ser, Asp or Glu. In some embodiments, the amino acid substitution results in less deamidation of the AAV capsid.

In some embodiments of the above aspects and embodiments, the AAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, an AAV DJ8 capsid, AAV2 N587A, AAV2 E548A, AAV2 N708A, AAV V708K, goat AAV, AAV1/AAV2 chimeric, bovine AAV, mouse AAV, rAAV2/HBoV1, AAV2HBKO, AAVPHP.B, or AAVPHP.eB serotype capsid. In some embodiments, the AAV capsid further comprises a tyrosine mutation or a heparin binding mutation.

In some aspects, the invention provides a method of improving stability of a rAAV particle comprising substituting amino acid residue 2 of VP1 and/or VP3 of a parent VP1 and/or VP3; wherein the substituting amino acid residue 2 alters N-terminal acetylation of VP1 and/or VP3, as compared to amino acid residue 2 of the parent VP1 and/or VP3. In some aspects, the invention provides a method of improving assembly of rAAV particles in a cell comprising substituting amino acid residue 2 of VP1 and/or VP3 or a parental VP1 and/or VP3; wherein substituting amino acid at position 2 alters N-terminal acetylation of VP1 and/or VP3, as compared to amino acid residue 2 of the parent VP1 and/or VP3. In some aspects, the invention provides a method of improving the transduction of rAAV particles in a cell comprising substituting amino acid residue 2 of VP1 and/or VP3 or a parental VP1 and/or VP3; wherein substituting amino acid residue 2 alters N-terminal acetylation of VP1 and/or VP3, as compared to amino acid residue 2 of the parent VP1 and/or VP3. In some embodiments, the substituted amino acid results in a higher frequency of N-terminal acetylation or a lower frequency of N-terminal acetylation. In some embodiments, the amino acid substitution at amino acid residue 2 of VP1 is substituted. In some embodiments, the amino acid substitution at amino acid residue 2 of VP3 is substituted. In some embodiments, amino acid residue 2 is substituted with Cys, Ser, Thr, Val, Gly, Asn, Asp, Glu, Ile, Leu, Phe, Gln, Lys, Met, Pro or Tyr. In some embodiments, amino acid residue 2 is substituted with Ser, Asp or Glu. In some aspects, the invention provides a method of reducing the transduction of rAAV particles in a cell comprising substituting amino acid residue 2 of VP1 and/or VP3; wherein the substituted amino acid at position 2 alters N-terminal acetylation of VP1 and/or VP3, as compared to amino acid residue 2 of the parent VP1 and/or VP3.

In some embodiments of the above aspects and embodiments, the AAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, an AAV DJ8 capsid, AAV2 N587A, AAV2 E548A, AAV2 N708A, AAV V708K, goat AAV, AAV1/AAV2 chimeric, bovine AAV, mouse AAV, rAAV2/HBoV1, AAV2HBKO, AAVPHP.B, or AAVPHP.eB serotype capsid. In some embodiments, the AAV capsid further comprises a tyrosine mutation or a heparin binding mutation. In some embodiments, the rAAV particle comprises a rAAV vector. In some embodiments, the rAAV vector comprises one or more AAV ITRs. In some embodiments, the rAAV vector comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11 ITR, or an AAV12 ITR. In some embodiments, the AAV capsid and the AAV ITRs are derived from the same serotype. In some embodiments, the AAV capsid and the AAV ITRs are derived from different serotypes. In some embodiments, the AAV particle comprises an AAV vector encoding a heterologous transgene flanked by one or more AAV ITRs.

In some embodiments of the above aspects and embodiments, the rAAV vector is a self-complementary vector. In some embodiments, the rAAV vector comprises first nucleic acid sequence encoding the transgene and a second nucleic acid sequence encoding a complement of the transgene, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the rAAV particle is produced by transfecting a host cell with nucleic acid encoding the rAAV vector and nucleic acid encoding AAV rep and cap functions, and providing nucleic acid encoding AAV helper functions. In some embodiments, the AAV helper functions are provided by transfecting the host cell with nucleic acid encoding the AAV helper functions. In some embodiments, the AAV helper functions are provided by infecting the host cell with an AAV helper virus that provides the AAV helper functions. In some embodiments, the AAV helper virus is an adenovirus, a herpes simplex virus or a baculovirus. In some embodiments, the rAAV particle is produced by an AAV producer cell comprising nucleic acid encoding the rAAV vector and nucleic acid encoding AAV rep and cap functions, and providing nucleic acid encoding AAV helper functions. In some embodiments, the AAV producer cell comprises nucleic acid encoding AAV helper functions. In some embodiments, the AAV helper functions are provided by infecting the AAV producer cells with an AAV helper virus that provides the AAV helper functions. In some embodiments, the AAV helper virus is an adenovirus, a herpes simplex virus, or a baculovirus. In some embodiments, the AAV cap functions provide an amino acid substitution at amino acid residue 2 of VP1 and/or VP3, wherein the amino acid substitution at amino acid residue 2 of VP1 and/or VP3 alters N-terminal acetylation compared to N-terminal acetylation at amino acid residue 2 of VP1 and/or VP3 of the parent AAV particle.

In some aspects, the invention provides a recombinant AAV (rAAV) particle comprising one or more amino acid substitutions at amino acid residue A35, N57, G58, N382, G383, N511, G512, N715, or G716 of VP1 or VP3 of a parent particle, residue numbering based on VP1 of AAV2; wherein the one or more amino acid substitutions alters deamidation as compared to deamidation of VP1 and/or VP3 of the parent AAV particle. In some embodiments, the one or more amino acid substitution is at amino acid residue A35, N57 of VP1, G58 of VP1, N382 of VP3, G383 of VP3, N511 of VP3, G512 of VP3, N715 of VP3, or G716 of VP3 and alters deamidation as compared to deamidation of VP1 and/or VP3 of the parent AAV particle. In some embodiments, the one or more amino acid substitutions comprises a substitution with Asp at N57 of VP1, N382 of VP3, N511 of VP3, or N715 of VP3; and results in a higher frequency of deamidation as compared to deamidation of VP1 and/or VP3 of the parent AAV particle. In some embodiments, the one or more amino acid substitutions comprise a N57K or a N57Q substitution and results in a lower frequency of deamidation as compared to deamidation of VP1 and/or VP3 of the parent AAV particle. In some embodiments, the one or more amino acid substitution comprise a substitution with Asp at A35 of VP1 and results in a higher frequency of deamidation as compared to deamidation of VP1 of the parent AAV particle. In some embodiments, the one or more amino acid substitutions is at G58 of VP1, G383 of VP3, G512 of VP3, or G716 of VP3 and results in a lower frequency of deamidation as compared to deamidation of VP1 and/or VP3 of the parent AAV particle. In some embodiments, the G58 of VP1 is substituted with Asp. In some embodiments, the rAAV particle is an AAV1 particle or an AAV2 particle.

In some aspects, the invention provides pharmaceutical compositions comprising AAV particles comprising one or more amino acid substitutions at amino acid residue A35, N57, G58, N382, G383, N511, G512, N715, or G716 of VP1 or VP3, residue numbering based on VP1 of AAV2; wherein the amino acid substitution alters deamidation as compared to deamidation of VP1 and/or VP3 of the parent AAV particle. In some aspects, the invention provides kits comprising AAV particles or compositions comprising AAV particles wherein the AAV particles comprise one or more amino acid substitutions at amino acid residue A35, N57, G58, N382, G383, N511, G512, N715, or G716 of VP1 or VP3, residue numbering based on VP1 of AAV2; wherein the amino acid substitution alters deamidation as compared to deamidation of VP1 and/or VP3 of the parent AAV particle. In some aspects, the invention provides articles of manufacture comprising AAV particles or compositions comprising AAV particles wherein the AAV particles comprise one or more amino acid substitutions at amino acid residue A35, N57, G58, N382, G383, N511, G512, N715, or G716 of VP1 or VP3, residue numbering based on VP1 of AAV2; wherein the amino acid substitution alters deamidation as compared to deamidation of VP1 and/or VP3 of the parent AAV particle. In some aspects, the invention provides an AAV capsid protein comprising an amino acid substitution of a parent AAV capsid protein; wherein the amino acid substitution alters deamidation of the capsid compared to the parent AAV capsid protein.

In some aspects, the invention provides a method of improving the stability of a rAAV particle comprising substituting one or more amino acid residues, wherein the one or more amino acid residues is A35, N57, G58, N382, G383, N511, G512, N715, or G716, residue numbering based on VP1 of AAV2; wherein the amino acid substitution alters deamidation as compared to deamidation of VP1 and/or VP3 of the parent AAV particle. In some aspects, the invention provides a method of improving the assembly of rAAV particles in a cell comprising substituting one or more amino acid residues, wherein the one or more amino acid residues is A35, N57, G58, N382, G383, N511, G512, N715, or G716, residue numbering based on VP1 of AAV2; wherein the amino acid substitution alters deamidation as compared to deamidation of VP1 and/or VP3 of the parent AAV particle. In some aspects, the invention provides a method of improving the transduction of rAAV particles in a cell comprising substituting one or more amino acid residues, wherein the one or more amino acid residues is A35, N57, G58, N382, G383, N511, G512, N715, or G716, residue numbering based on VP1 of AAV2; wherein the amino acid substitution alters deamidation as compared to deamidation of VP1 and/or VP3 of the parent AAV particle. In some embodiments, the one or more amino acid substitutions is at A35 of VP1, N57 of VP1, G58 of VP1, N382 of VP3, G383 of VP3, N511 of VP3, G512 of VP3, N715 of VP3, or G716 of VP3; wherein the amino acid substitution alters deamidation as compared to deamidation of VP1 and/or VP3 of the parent AAV particle. In some embodiments, the parental Ala residue at position 35 of VP1 is substituted with Asn. In some embodiments, the parental Gly residue at position 58 of VP1 is substituted with Asp. In some embodiments, the rAAV particle is an AAV1 particle or an AAV2 particle.

In some embodiments, the invention provides a method of improving the stability, assembly and/or transduction efficiency of a rAAV particle comprising substituting one or more amino acid residues, wherein the one or more amino acid residues is A35, N57, G58, N382, G383, N511, G512, N715, or G716, residue numbering based on VP1 of AAV2; wherein the amino acid substitution alters deamidation as compared to deamidation of VP1 and/or VP3 of the parent AAV particle as described above, wherein the AAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, an AAV DJ8 capsid, AAV2 N587A, AAV2 E548A, AAV2 N708A, AAV V708K, goat AAV, AAV1/AAV2 chimeric, bovine AAV, mouse AAV, or rAAV2/HBoV1 serotype capsid. In some embodiments, the AAV capsid further comprises a tyrosine mutation or a heparin binding mutation. In some embodiments, the rAAV particle comprises a rAAV vector. In some embodiments, the rAAV vector comprises one or more AAV ITRs. In some embodiments, the rAAV vector comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11 ITR, or an AAV12 ITR. In some embodiments, the AAV capsid and the AAV ITRs are derived from the same serotype. In some embodiments, the AAV capsid and the AAV ITRs are derived from different serotypes. In some embodiments, the AAV particle comprises an AAV vector encoding a heterologous transgene flanked by one or more AAV ITRs.

In some embodiments of the above aspects and embodiments, the rAAV vector is a self-complementary vector. In some embodiments, the rAAV vector comprises first nucleic acid sequence encoding the transgene and a second nucleic acid sequence encoding a complement of the transgene, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the rAAV particle is produced by transfecting a host cell with nucleic acid encoding the rAAV vector and nucleic acid encoding AAV rep and cap functions, and providing nucleic acid encoding AAV helper functions. In some embodiments, the AAV helper functions are provided by transfecting the host cell with nucleic acid encoding the AAV helper functions. In some embodiments, the AAV helper functions are provided by infecting the host cell with an AAV helper virus that provides the AAV helper functions. In some embodiments, the AAV helper virus is an adenovirus, a herpes simplex virus or a baculovirus. In some embodiments, the rAAV particle is produced by an AAV producer cell comprising nucleic acid encoding the rAAV vector and nucleic acid encoding AAV rep and cap functions, and providing nucleic acid encoding AAV helper functions. In some embodiments, the AAV producer cell comprises nucleic acid encoding AAV helper functions. In some embodiments, the AAV helper functions are provided by infecting the AAV producer cells with an AAV helper virus that provides the AAV helper functions. In some embodiments, the AAV helper virus is an adenovirus, a herpes simplex virus, or a baculovirus. In some embodiments, the AAV cap functions provide an amino acid substitution of VP1 and/or VP3, wherein the amino acid substitution modulated deamidation of the capsid compared to the parent AAV particle.

BRIEF DESCRIPTION OF THE DRAWINGS

FIG. 1A: 10 cm long BEH C4 column with 1.7%/min gradient, FIG. 1B: 10 cm long BEH C4 column with 0.5%/min gradient; FIG. 1C: 15 cm long BEH C4 column with 0.5%/min gradient, FIG. 1D: 15 cm long BEH C8 column with 0.5%/min gradient.

FIG. 3 provides the sequence coverage of AAV2 VP1 (SEQ ID NO:3): green, tryptic peptides, blue, Lys-C peptides, pink, Asp-N peptides.

FIG. 4A: VP1 N-terminal tryptic peptide A(Ac)ADGYLPDWLEDTLSEGIR (SEQ ID NO: 4), FIG. 4B VP2 N-terminal Asp-N peptide APGKKRPVEHSPVEP (SEQ ID NO: 15). FIG. 4C: VP-3 N-terminal Asp-N derived peptide A(Ac)TGSGAPM (SEQ ID NO: 5).

FIG. 5A-5C provides the sequence alignment of 13 AAV serotypes black letter/white background: non-similar; blue letter/blue background: conservative; black letter/green background: block of similar; red letter/yellow background: identical; green letter/white background: weakly similar. AAVRh10 (SEQ ID NO: 17); AAV10 (SEQ ID NO: 18); AAV8 (SEQ ID NO: 19); AAV7 (SEQ ID NO: 20); AAV1 (SEQ ID NO: 21); AAV6 (SEQ ID NO: 22); AAV2 (SEQ ID NO: 23); AAV3 (SEQ ID NO: 24); AAV11 (SEQ ID NO: 25); AAV12 (SEQ ID NO: 26); AAV4 (SEQ ID NO: 27); AAV5 (SEQ ID NO: 28); AAV9 (SEQ ID NO: 29); Consensus (SEQ ID NO: 30).

FIG. 9 shows the results of SYPRO protein gel analysis of production and VP1:VP2:VP3 ratio of AAV5 deacetylated mutant variants.

FIG. 15 shows the results of LC/MS analysis of deamidation of the indicated AAV2 mutants, as compared to control AAV2 capsids.

DETAILED DESCRIPTION

Figure 1A:
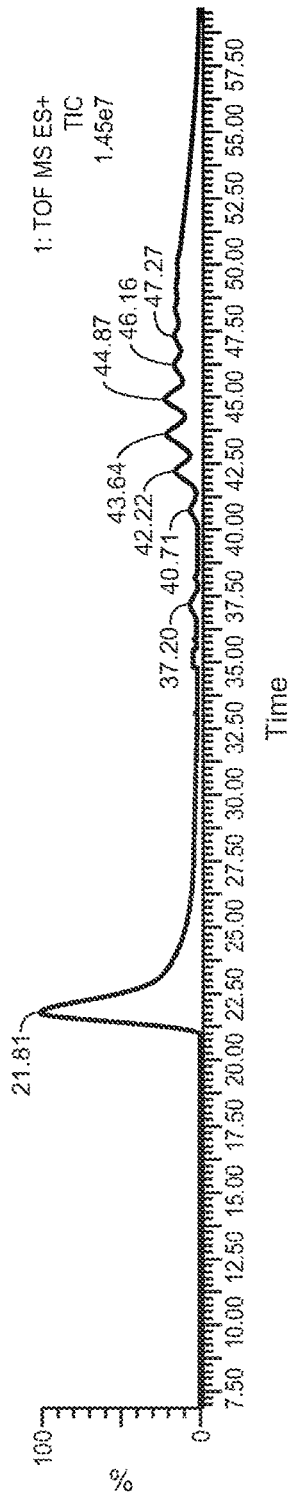
FIGS. 1A-D provide total ion Chromatograms of LC/MS of AAV2 VPs.

In some aspects, the invention provides a method to determine the serotype of an adeno-associated virus (AAV) particle(s) comprising: a) denaturing the AAV particle, b) injecting the denatured AAV particle to liquid chromatography/mass spectrometry (LC/MS), and c) determining the masses of VP1, VP2 and VP3 of the AAV particle; wherein the specific combination of masses of VP1, VP2 and VP3 are indicative of the AAV serotype.

In other aspects, the invention provides a method of determining the heterogeneity of an AAV particle comprising: a) denaturing the AAV particle, b) injecting the denatured AAV particle to liquid chromatography/mass spectrometry (LC/MS), and c) determining the masses of VP1, VP2 and VP3 of the AAV particle, and comparing the masses of step c) with the theoretical masses of VP1, VP2 and VP3 of the AAV serotype; wherein a deviation of one or more of the masses of VP1, VP2 or VP3 are indicative of the AAV capsid heterogeneity.

In other aspects, the invention provides a method to determine the serotype of an adeno-associated virus (AAV) particle comprising a) denaturing the AAV particle, b) subjecting the denatured AAV particle to reduction and/or alkylation, c) injecting the denatured AAV particle to digestion to generate fragments of VP1, VP2 and/or VP3 of the AAV particle, d) subjecting the fragments of VP1, VP2 and/or VP3 to liquid chromatography/mass spectrometry-mass spectrometry (LC/MS/MS), and e) determining the masses of fragments of VP1, VP2 and VP3 of the AAV particle; wherein the specific combination of masses of fragments of VP1, VP2 and VP3 are indicative of the AAV serotype.

In other aspects, the invention provides a method of determining the heterogeneity of an AAV particle of a serotype comprising: a) denaturing the AAV particle, b) subjecting the denatured AAV particle to reduction and/or alkylation, c) injecting the denatured AAV particle to digestion to generate fragments of VP1, VP2 and/or VP3 of the AAV particle, d) subjecting the fragments of VP1, VP2 and/or VP3 to liquid chromatography/mass spectrometry-mass spectrometry (LC/MS/MS), e) determining the masses of fragments of VP1, VP2 and VP3 of the AAV particle, and f) comparing the masses of step e) with the theoretical masses of fragments of VP1, VP2 and VP3 of the AAV serotype; wherein a deviation of one or more of the masses of VP1, VP2 or VP3 are indicative of the AAV capsid heterogeneity.

In some aspects, the invention provides a recombinant AAV (rAAV) particle comprising an amino acid substitution at amino acid residue 2 of VP1 and/or VP3; wherein the amino acid substitution at amino acid residue 2 of VP1 and/or VP3 alters N-terminal acetylation compared to N-terminal acetylation at amino acid residue 2 of VP1 and/or VP3 of the parent AAV particle.

In some aspects, the invention provides a method of improving the assembly of rAAV particles in a cell comprising substituting amino acid residue 2 of VP1 and/or VP3; wherein the substituted amino acid at position 2 is N-acetylated at a higher frequency than amino acid residue 2 of the parent VP1 and/or VP3. In some aspects, the invention provides a method of improving the transduction of rAAV particles in a cell comprising substituting amino acid residue 2 of VP1 and/or VP3; wherein the substituted amino acid at position 2 is N-acetylated at a higher frequency than amino acid residue 2 of the parent VP1 and/or VP3.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6, ed., J. Wiley and Sons, 2010); *Oligonucleotide Synthesis* (M. J. Gait, ed., 1984); *Methods in Molecular Biology, Humana Press; Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups. Alternatively, the backbone of the nucleic acid can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded nucleic acid can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-translational modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, e.g., two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, e.g., two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and, in embodiments, encapsidated in a viral particle, particularly an AAV particle.

A rAAV vector can be packaged into an AAV virus capsid to generate a "recombinant adeno-associated viral particle (rAAV particle)".

An "rAAV virus" or "rAAV viral particle" refers to a viral particle composed of at least one AAV capsid protein and an encapsidated rAAV vector genome.

A "parent AAV particle" and "parent AAV capsid protein" as used herein in the context of comparing N-acetylation and/or deamidation refers to an AAV particle or capsid protein into which amino acid modifications are introduced to modulate N-acetylation and/or deamidation (e.g., an AAV particle/capsid protein that is the same as or similar to the AAV particle/capsid of the subject invention but does not comprise the mutations that modulate/alter N-acetylation and/or deamidation as described herein). In some embodiments, the parent AAV particle is a recombinant AAV particle comprising a recombinant AAV genome. In some embodiments, the parent AAV capsid particle or parent AAV capsid protein comprises amino acid substitutions that affect other aspects of the AAV particle. For example, the parent AAV particle may comprise amino acid substitutions that affect the binding of AAV to its receptor, such as affecting binding of AAV2 to heparin sulfate proteoglycan (e.g. an AAV2 HBKO particle). An AAV2 HBKO particle can be mutated to introduce amino acid substitutions that modulate N-acetylation and/or deamidation. Such a mutated AAV particle may then be compared to the parent AAV2 HBKO particle in aspects of the invention as described herein. A parent AAV capsid protein may include a parent VP1 capsid protein, a parent VP2 capsid protein, or a VP3 capsid protein.

As used herein, the term "modulate" or "alter" in reference to a parent molecule means to change a feature of the parent molecule. For example, an AAV particle with altered N-acetylation may show increased or decreased N-acetylation compared to the parent AAV particle and an AAV particle with altered deamidation may show increased or decreased deamidation compared to the parent AAV particle.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a nucleic acid that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.,* 10:1031-1039; Veldwijk et al. (2002) *Mol. Ther.,* 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.,* 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.,* 144:113-124; or in Fisher et al. (1996) *J. Virol.,* 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins. "AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A number of such helper viruses have been identified, including adenoviruses, herpesviruses, poxviruses such as vaccinia, and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Baculoviruses available from depositories include *Autographa californica* nuclear polyhedrosis virus.

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A potential alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

"Mass spectrometry" refers to the analytical chemistry technique of identifying an amount and/or type of a compound (e.g., a polypeptide) by measuring the mass-to-charge ratio and abundance of gas-phase ions. The term "mass spectrometry" may be used interchangeably herein.

"Heterogeneity" when used in reference to an AAV capsid refers to an AAV capsid characterized by one or more capsid polypeptides observed to deviate from a reference mass of a VP1, VP2, and/or VP3 polypeptide, or fragment thereof. A reference mass may include, without limitation, a theoretical, predicted, or expected mass of a VP1, VP2, and/or VP3 polypeptide, e.g., of a known AAV serotype. For example, an AAV capsid may be said to display heterogeneity if it demonstrates one or more of the following properties (without limitation): a mixed serotype, a variant capsid, a capsid amino acid substitution, a truncated capsid, or a modified capsid.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Methods

Certain aspects of the present disclosure relate to methods of determining the serotype of a viral particle. Other aspects of the present disclosure relate to methods of determining the heterogeneity of a viral particle. As described below, the accurate masses of VP1, VP2 and VP3 of each AAV serotype are unique and can be used to identify or differentiate AAV capsid serotypes. These methods are based in part on the discovery described herein that direct LC/MS of different types of AAVs after denaturation may be used to monitor the protein sequence and post-translational modifications with accurate mass measurement in the intact protein level. Further, acetylations of N-termini of VP1 and VP3 may also be identified and/or monitored in different AAV serotypes. Based on these AAV results and the guidance provided herein, it is contemplated that such methods may readily be applied to profile a variety of viruses, e.g., the viral families, subfamilies, and genera of the present disclosure. The methods of the present disclosure may find use, e.g., in profile VPs to monitor VP expressions, posttranslational modifications, and truncations and to ensure product consistency during VLP production, to confirm site-direct mutagenesis or structural characterization for capsid protein engineering applications, and/or to monitor or detect heterogeneity of a viral particle or preparation.

In some embodiments, the methods include denaturing a viral particle. In some embodiments, a viral particle such as an AAV particle may be denatured using detergent, heat, high salt, or buffering with a low or high pH. In certain embodiments, an AAV particle may be denatured using acetic acid or guanidine hydrochloride. The skilled artisan will recognize that a variety of methods useful for promoting and/or monitoring protein denaturation are available in the art and may suitably select a denaturation method compatible with liquid chromatography/mass spectrometry. For example, if heat denaturation is used, care may be applied to avoid protein precipitation and reverse phase column clogging. Similarly, high salt denaturation may be coupled with a desalting step prior to LC/MS or LC/MS/MS. In other embodiments, high pH denaturation, low pH denaturation, or denaturation using organic solvents is used.

In some embodiments, the methods include subjecting a denatured viral particle of the present disclosure to liquid chromatography/mass spectrometry (LC/MS). As is known in the art, LC/MS utilizes liquid chromatography for physical separation of ions and mass spectrometry for generation of mass spectral data from the ions. Such mass spectral data may be used to determine, e.g., molecular weight or structure, identification of particles by mass, quantity, purity, and so forth. These data may represent properties of the detected ions such as signal strength (e.g., abundance) over time (e.g., retention time), or relative abundance over mass-to-charge ratio.

In some embodiments, liquid chromatography (e.g., used in LC/MS as described herein) is ultra-performance liquid chromatography (UPLC; the term "ultra high performance liquid chromatography" or UHPLC may be used interchangeably herein). UPLC is known in the art as an LC technique that relies upon a column with reduced particle size (e.g., less than 2 μm) and increased flow velocity to improve chromatographic resolution, efficiency, peak capacity, and sensitivity (see, e.g., Plumb, R. et al. (2004) *Rapid Commun. Mass Spectrom.* 18:2331-2337). In some embodiments, UPLC refers to the use of a column with a particle size less than 2 μm in liquid chromatography. In some embodiments, UPLC refers to the use of a high linear solvent velocity (e.g., as observed when operating at 6000 psi or higher) in liquid chromatography. Exemplary UPLC machines are commercially available (e.g., the ACQUITY UPLC® from Waters; Milford, MA).

In some embodiments, mass spectrometry (e.g., used in LC/MS as described herein) may refer to electrospray ionization mass spectrometry (ESI-MS). ESI-MS is known in the art as a technique that uses electrical energy to analyze ions derived from a solution using mass spectrometry (see, e.g., Yamashita, M. and Fenn, J. B. (1984) *J. Phys. Chem.* 88:4451-4459). Ionic species (or neutral species that are ionized in solution or in gaseous phase) are transferred from a solution to a gaseous phase by dispersal in an aerosol of charged droplets, followed by solvent evaporation that reduces the size of the charged droplets and sample ion ejection from the charge droplets as the solution is passed through a small capillary with a voltage relative to ground (e.g., the wall of the surrounding chamber). In some embodiments, the capillary voltage is from about 2 kV to about 10 kV, or about 2.5 kV to about 6.0 kV. In certain embodiments, liquid chromatography (e.g., used in LC/MS as described herein) uses a capillary voltage of about 3.5 kV. In some embodiments the capillary voltage ranges from about 1 kV to about 10 kV. In other embodiments, mass spectrometry (e.g., used in LC/MS as described herein) may refer to matrix-assisted laser desorption/ionization (MALDI).

In some embodiments, mass spectrometry (e.g., used in LC/MS as described herein) uses a sampling cone and/or skimmer, through which ions may pass before entering the analyzer. In some embodiments, e.g., when applying voltage to the capillary as described above, the sample cone is held at a lower voltage than the capillary voltage. In certain embodiments, liquid chromatography (e.g., used in LC/MS as described herein) uses a sampling cone voltage of about 45 V. In some embodiments the sampling cone voltage ranges from about 0 V to about 200 V.

In some embodiments, mass spectrometry (e.g., used in LC/MS as described herein) uses assisted calibration. Calibration, when used in reference to mass spectrometry, may include the introduction of one or more compounds having a known mass (e.g., a standard) for the purpose of calibrating the instrument with respect to mass detection (e.g., m/z measurements). In some embodiments, assisted calibration may refer to using software to correlate a peak and/or position of a known standard (e.g., a calibrant) to a specific mass-to-charge (m/z) ratio. Once calibrated, the user may then perform mass spectrometry on a sample having one or more unknown compounds, or compounds present at an unknown concentration, within a certain degree of accuracy or error, and/or a desired level of reproducibility, e.g., as compared to a previous or known experimental condition. Various calibrants are known in the art, including without limitation sodium iodide, sodium cesium iodide, polyethylene glycol, and perfluorotributylamine. In certain embodiments, sodium iodide is used as a calibrant. In some embodiments the calibrants are Glu-1-fibrinopeptide B and leucine encephalin peptide to lock mass during LC/MS operation.

In some embodiments, the methods include subjecting a denatured viral particle of the present disclosure, or subjecting digested fragments of a denatured viral particle of the present disclosure, to liquid chromatography/mass spectrometry-mass spectrometry (LC/MS/MS). As is known in the art, LC/MS/MS (the term "liquid chromatography-tandem mass spectrometry" may be used interchangeably herein) utilizes liquid chromatography for physical separation of ions and mass spectrometry for generation of mass spectral data from the ions, where the mass spectrometry uses multiple stages of mass (e.g., m/z) separation, typically separated by a fragmentation step. For example, ions of interest within a range of m/z may be separated out in a first round of MS, fragmented, and then further separated based on individual m/z in a second round of MS. Ion fragmentation may include without limitation a technique such as collision-induced dissociation (CID), higher energy collision dissociation (HCD), electron-capture dissociation (ECD), or electron-transfer dissociation (ETD).

In some embodiments, the methods include subjecting a denatured viral particle of the present disclosure to reduction and/or alkylation. Means to reduce the viral particle include but are not limited to treatment with dithiothreitol, β-mercaptoethanol, or tris(2-carboxyethyl)phosphine (TCEP). Means to alkylate the viral particle include but are not limited to treating the AAV particle with iodoacetic acid, iodoacetamide, or 4-vinylpyridine.

In some embodiments, the methods include subjecting a denatured viral particle of the present disclosure to digestion, e.g., to generate fragments of VP1, VP2 and/or VP3 of an AAV particle. For example, a denatured AAV particle may be subjected to digestion to generate peptide fragments that may be analyzed, e.g., using LC for separation and MS/MS for analysis (see below for greater description). In some embodiments, the digestion is an enzymatic digestion. In some embodiments, the digestion uses chemical digestion such as CNBr treatment of instrument fragmentation (e.g., top down). In some embodiments, the digestion uses chemical digestion such as acid digestion.

In some embodiments, the enzymatic digestion is an endopeptidase digestion. An endopeptidase may include any peptidase that catalyzes the proteolysis of peptide bonds of non-terminal amino acids of a polypeptide. Known endopeptidases may include, without limitation, trypsin, chymotrypsin, AspN, Glu-C, LysC, pepsin, thermolysin, glutamyl endopeptidase, elastase, and neprilysin. In certain embodiments, the enzymatic digestion is a trypsin digestion or a LysC digestion.

In some embodiments, the liquid chromatography (e.g., used in LC/MS or LC/MS/MS as described herein) is reverse phase liquid chromatography (the terms "reversed phase liquid chromatography" or RPLC may be used interchangeably herein with reverse phase liquid chromatography). As is known in the art, reverse phase liquid chromatography may refer to a chromatographic separation using a hydrophobic stationary phase (e.g., a support or substrate such as a column) to adsorb hydrophobic molecules in a polar mobile phase. By decreasing the polarity of the mobile phase (e.g., by adding an organic solvent), one may achieve gradient separation of molecules by hydrophobicity, since more hydrophobic molecules will stay on the column in higher concentrations of organic solvent due to stronger hydrophobic interactions with the column. In some embodiment, separation is by capillary electrophoresis (CE), size exclusion chromatography (SEC), ion exchange chromatography (IEC) such as cation exchange chromatography, hydrophobic interaction chromatography (HIC), hydrophilic interaction liquid chromatography (HILIC), but not limited to on-line LC/MS such as offline separation before MS; e.g., tips, columns; plates or cartridges.

Generally, a stationary phase suitable for reverse phase liquid chromatography (e.g., a hydrophobic moiety) may be coupled to a support including without limitation a column or resin packed with particles or beads (e.g., porous silica particles or polystyrene). A variety of hydrophobic stationary phases are known in the art, including without limitation hydrophobic alkyl chains, octyl or octadecyl silyl moieties, cyano moieties, and amino moieties. In some embodiments, the stationary phase may include a hydrophobic alkyl chain of a particular length, such as C4, C8, or C18. In certain embodiments, the reverse phase chromatography is a C4 or C8 reverse chromatography (e.g., reverse phase chromatography utilizing a C4 or C8 stationary phase). One of skill in the art may suitably select a stationary phase based on the molecule of interest (e.g., a denatured AAV particle or fragment thereof).

A variety of mobile phases suitable for reverse phase liquid chromatography are known in the art. As described above, a reverse phase liquid chromatography mobile phase may include a mixture of organic (e.g., hydrophobic) and aqueous (e.g., polar) solvents. Increasing the proportion of organic solvent increases its power to elute hydrophobic compounds from the stationary phase. Compound retention and/or selectivity may be altered, e.g., by changing the type or exposure of the stationary phase, adding polar reagents such as end capping reagents, altering the temperature, and/or altering mobile phase characteristics such as the proportion of organic solvent, pH, buffers, and the type of organic solvent used. In some embodiments, the polar component of the mobile phase may include without limitation water or an aqueous buffer. In some embodiments, the polar component of the mobile phase may include without limitation acetonitrile, methanol, ethanol, isopropyl alcohol, tetrahydrofuran (THF), and formic acid.

In some embodiments, two or more mobile phases may be used (e.g., mobile phase A, mobile phase B, etc.) in a gradient or proportion of interest. In certain embodiments, the chromatography uses a mobile phase A comprising formic acid in water. In certain embodiments, the mobile phase A comprises about 0.1% formic acid. In certain embodiments, the mobile phase A comprises about 0.1% to about 5% formic acid. In certain embodiments, the chromatography uses a mobile phase B comprising formic acid in acetonitrile. In certain embodiments, the mobile phase B comprises about 0.1% formic acid.

In some embodiments, the proportion of mobile phase B in the chromatography increases over time. For example, the proportion of mobile phase B in the chromatography may be increased in a stepwise manner. In certain embodiments, mobile phase B increases from about 10% to about 20%, from about 20% to about 30%, and from about 30% to about 38%. In other embodiments, mobile phase B increases from about 2% to about 60%. In other embodiments, mobile phase B increases from about 2% to about 100% from about 1 min to about 200 min In some embodiments, the remainder of the mobile phase is a second mobile phase of the present disclosure, e.g., mobile phase A. In certain embodiments, mobile phase B increases from about 10% to about 20% in about 6 minutes, from about 20% to about 30% in about 10 minutes, and from about 30% to about 38% in about 40 minutes. In other embodiments, mobile phase B increases from about 2% to about 60% in about 121 minutes. One of skill in the art may suitably adjust the mobile phase of interest and the gradient timing used based on the desired chromatographic separation and/or analyte of interest.

In some embodiments, the liquid chromatography is high-performance liquid chromatography (HPLC). HPLC is known in the art as a form of liquid chromatography in which a liquid solvent containing a sample is pressurized as it passes through a column containing solid phase. While traditional or low pressure LC may use gravity to pass a mobile phase through the solid phase, HPLC uses pumps to apply a pressure to the mobile phase and typically uses a solid phase with smaller particles to increase resolution. In some embodiments, the HPLC uses a pressure of between about 50 bar and about 350 bar. In some embodiments, reversed phase HPLC may be used to concentrate and/or desalt proteins (e.g., AAV capsid proteins) for MS analysis.

In some embodiments, one or more parameters including without limitation source voltage, capillary temperature, ESI voltage (if using ESI-MS), CID energy, and the number of MS/MS events may be adjusted, e.g., in LC/MS/MS as used herein, based on the findings described herein. In some embodiments, mass spectrometry (e.g., used in LC/MS/MS as described herein) uses a source voltage (e.g., capillary voltage) of about 2.5 kV. In some embodiments, mass spectrometry (e.g., used in LC/MS/MS as described herein) uses a capillary temperature of about 275° C. In some embodiments, the capillary temperature ranges from about 20° C. to about 400° C.

A variety of mass analyzers suitable for LC/MS and/or LC/MS/MS are known in the art, including without limitation time-of-flight (TOF) analyzers, quadrupole mass filters, quadrupole TOF (QTOF), and ion traps (e.g., a Fourier transform-based mass spectrometer or an Orbitrap). In Orbitrap, a barrel-like outer electrode at ground potential and a spindle-like central electrode are used to trap ions in trajectories rotating elliptically around the central electrode with oscillations along the central axis, confined by the balance of centrifugal and electrostatic forces. The use of such instruments employs a Fourier transform operation to convert a time domain signal (e.g., frequency) from detection of image current into a high resolution mass measurement (e.g., nano LC/MS/MS). Further descriptions and details may be found, e.g., in Scheltema, R. A. et al. (2014) *Mol. Cell Proteomics* 13:3698-3708; Perry, R. H. et al. (2008) *Mass. Spectrom. Rev.* 27:661-699; and Scigelova, M. et al. (2011) *Mol. Cell Proteomics* 10:M111.009431.

As described above, in some embodiments, the MS includes nano LC/MS/MS, e.g., using an Orbitrap mass analyzer. In some embodiments, the ion source may include a stacked-ring ion guide or S-lens. As is known in the art, an S-lens may be employed to focus the ion beam using radio frequency (RF), thereby increasing transmission of ions into the instrument. This may improve sensitivity (e.g., for low-intensity ions) and/or improve the scan rate. In certain embodiments, the S-lens RF level of the mass spectrometry is about 55%. In certain embodiments, the S-lens RF level of the mass spectrometry is about 20% to about 100%.

In some embodiments, masses of viral capsid proteins may be determined, e.g., based on LC/MS and/or LC/MS/MS data. In some embodiments, masses of VP1, VP2 and VP3 of an AAV particle, or of fragments of VP1, VP2 and VP3 of the AAV particle, may be determined, e.g., based on LC/MS and/or LC/MS/MS data. Various methods to determine protein mass and/or identity from MS data are known in the art. For example, peptide mass fingerprinting may be used to determine protein sequence based on MS data, or proteins may be identified based on MS/MS data related to one or more constituent peptides. When using tandem MS, product ion scanning may be used to analyze m/z data related to one or more peptides of a protein of interest. Software known in the art may then be used, e.g., to match identified peaks to reference or known peaks, to group peaks into isotopomer envelopes, and so forth. Peptide mass values may be compared to a database of known peptide sequences. For example, Mascot may be used to match observed peptides with theoretical database peptides, e.g., resulting from application of a particular digest pattern to an in silico protein database. Other suitable software may include without limitation Proteome Discoverer, ProteinProspector, X!Tandem, Pepfinder, Bonics, or MassLynx™ (Waters). Other software suitable for various steps of MS data analysis may be found, e.g., at www.ms-utils.org/wiki/pmwiki.php/Main/SoftwareList.

In some embodiments, a determined or calculated mass of the present disclosure (e.g., the determined or calculated mass of VP1, VP2 and/or VP3 of the AAV particle) may be compared with a reference, e.g., a theoretical mass of a VP1, VP2, and/or VP3 of one or more AAV serotypes. A reference of the present disclosure may include a theoretical mass of a VP1, VP2, and/or VP3 of one or more of any of the AAV serotypes described herein. For example, in some embodiments, the masses of VP1, VP2, and/or VP3 are compared to the theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV LK03 capsid (see U.S. Pat. No. 9,169,299), an AAV2R471A capsid, an AAV2/2-7m8 capsid, an AAV DJ capsid (see U.S. Pat. No. 7,588,772), an AAV DJ8 capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1), an AAV2HBKO capsid, an AAVPHP.B capsid or an AAVPHP.eB capsid. In some embodiments, a determined or calculated mass of the present disclosure (e.g., the determined or calculated mass of VP1, VP2 and/or VP3 of the AAV particle) may be compared with a theoretical mass of a VP1, VP2, and/or VP3 of the corresponding AAV serotype.

In some embodiments, the methods of the present disclosure may include determining the heterogeneity of an AAV particle. In some embodiments, a deviation of one or more of the masses of VP1, VP2 and/or VP3 (e.g., from a reference mass, such as a theoretical, predicted, or expected mass) is indicative of the AAV capsid heterogeneity. In some embodiments, heterogeneity may include one or more of the following, without limitation: mixed serotypes, variant capsids, capsid amino acid substitutions, truncated capsids, or modified capsids.

In some embodiments, the use of LC/MS and LC/MS/MS as described herein may be combined. In some embodiments, a method of determining the serotype of an AAV particle may include subjecting a denatured AAV particle to LC/MS (e.g., as described herein) and determining the masses of VP1, VP2 and VP3 of the AAV particle; as well as subjecting fragments of VP1, VP2 and/or VP3 to LC/MS/MS and determining the masses of fragments of VP1, VP2 and VP3 of the AAV particle (the specific combination of masses of fragments of VP1, VP2 and VP3 are indicative of the AAV serotype). In some embodiments, a method of determining the heterogeneity of an AAV particle may include subjecting a denatured AAV particle to LC/MS (e.g., as described herein), determining the masses of VP1, VP2 and VP3 of the AAV particle, and comparing these masses with the theoretical masses of VP1, VP2 and VP3 of the AAV serotype; as well as subjecting fragments of VP1, VP2 and/or VP3 to LC/MS/MS, determining the masses of fragments of VP1, VP2 and VP3 of the AAV particle, and comparing these masses with the theoretical masses of VP1, VP2 and VP3 of the AAV serotype (a deviation of one or more of the masses of VP1, VP2 or VP3 are indicative of the AAV capsid heterogeneity).

In some embodiments, an AAV particle of the present disclosure may be acetylated. For example, in some embodiments, the N-terminus of VP1 and/or VP3 is acetylated. As described in greater detail below, the amino acid at the $2^{nd}$ position to the initiating methionine (iMet X) of an AAV capsid protein may be mutated in order to determine its effect on N-terminal (Nt-) acetylation, as well as the functional consequences of affecting Nt-acetylation on AAV particle trafficking, transduction, and/or post-translational modification (e.g., glycosylation, ubiquitination, and so forth). In some embodiments, the N-terminus of an AAV capsid protein (e.g., VP1 or VP3) may refer to the first amino acid after the initiating methionine, which in some cases may be removed by, e.g., a Met-aminopeptidase.

In some embodiments, an AAV particle of the present disclosure (e.g., a recombinant AAV or rAAV particle) comprises an amino acid substitution at amino acid residue 2 of VP1 and/or VP3. In some embodiments, the amino acid substitution at amino acid residue 2 of VP1 and/or VP3 leads to a VP1 and/or VP3 with a different frequency or proportion of N-terminal acetylation as compared to a reference (e.g., the parent AAV particle before the amino acid substitution, or an AAV particle with a different amino acid residue 2 of VP1 and/or VP3). In some embodiments, the amino acid substitution at amino acid residue 2 of VP1 and/or VP3 alters N-terminal acetylation as compared to N-terminal acetylation at amino acid residue 2 of VP1 and/or VP3 of the parent AAV particle. For example, in certain embodiments, the amino acid substitution at amino acid residue 2 of VP1 alters N-terminal acetylation as compared to N-terminal acetylation at amino acid residue 2 of VP1 of the parent AAV particle. In certain embodiments, the amino acid substitution at amino acid residue 2 of VP3 alters N-terminal acetylation as compared to N-terminal acetylation at amino acid residue 2 of VP3 of the parent AAV particle. In some embodiments, an amino acid substitution (e.g., an amino acid substitution at amino acid residue 2 of VP1 or VP3) that "alters" N-terminal acetylation results in a higher frequency of N-terminal acetylation or a lower frequency of N-terminal acetylation, e.g., as compared to a VP1 or VP3 without the substitution, such as the parental VP1 or VP3. The VP1 and/or VP3 may belong to any of the exemplary AAV serotypes described herein, including variants or hybrids thereof (e.g., bearing tyrosine mutation or heparin binding mutations). Exemplary assays for N-terminal acetylation include without limitation mass spectrometry, isotope labeling (e.g., with an isotope-labeled acetyl group or precursor thereof), Western blotting with an acetylation-specific antibody, and so forth. In some embodiments, amino acid residue 2 of the AAV capsid protein (e.g., VP1 or VP3) is substituted with Cys, Ser, Thr, Val, Gly, Asn, Asp, Glu, Ile, Leu, Phe, Gln, Lys, Met, Pro or Tyr. In some embodiments, the amino acid substitution results in less deamidation of the AAV capsid.

In some embodiments, an AAV particle of the present disclosure may be deamidated. For example, in some embodiments, N57 of VP1 and/or N382, N511, and/or N715 VP3 is deamidated. As described in greater detail below, an amino acid selected from A35 of VP1, N57 of VP1, G58 of VP1, N382 of VP3, G383 of VP3, N511 of VP3, G512 of VP3, N715 of VP3, or G716 of VP3 of an AAV capsid protein (e.g., VP1 or VP3) may be mutated in order to determine its effect on deamidation, as well as the functional consequences of affecting deamidation on AAV particle trafficking, transduction, and/or post-translational modification (e.g., glycosylation, ubiquitination, and so forth).

In some embodiments, an AAV particle of the present disclosure (e.g., a recombinant AAV or rAAV particle) comprises an amino acid substitution at one or more amino acid residues selected from A35 of VP1, N57 of VP1, G58 of VP1, N382 of VP3, G383 of VP3, N511 of VP3, G512 of VP3, N715 of VP3, and G716 of VP3. In some embodiments, the amino acid substitution at A35 of VP1, N57 of VP1, G58 of VP1, N382 of VP3, G383 of VP3, N511 of VP3, G512 of VP3, N715 of VP3, and/or G716 of VP3 leads to a VP1 and/or VP3 with a different frequency or proportion of deamidation as compared to a reference (e.g., the parent AAV particle before the amino acid substitution, or an AAV particle with a different corresponding amino acid residue 2). In some embodiments, an amino acid substitution (e.g., an amino acid substitution at A35 of VP1, N57 of VP1, G58 of VP1, N382 of VP3, G383 of VP3, N511 of VP3, G512 of VP3, N715 of VP3, or G716 of VP3) that "alters" deamidation results in a higher frequency of deamidation or a lower frequency of deamidation, e.g., as compared to a VP1 or VP3 without the substitution, such as the parental VP1 or VP3. The VP1 and/or VP3 may belong to any of the exemplary AAV serotypes described herein, including variants or hybrids thereof (e.g., bearing tyrosine mutation or heparin binding mutations). Exemplary assays for deamidation include without limitation mass spectrometry, HPLC (see, e.g., the ISOQUANT® isoaspartate detection kit from Promega), and so forth. In some embodiments, N57 of VP1, N382 of VP3, N511 of VP3, and/or N715 of VP3 is substituted with Asp, and the amino acid substitution results in a higher frequency of deamidation as compared to deamidation of VP1 and/or VP3 of the parent AAV particle. In other embodiments, the amino acid substitution is N57K or N57Q, and the amino acid substitution results in a lower frequency of deamidation as compared to deamidation of VP1 and/or VP3 of the parent AAV particle. In yet other embodiments, G58 of VP1, G383 of VP3, G512 of VP3, and/or G716 of VP3 is substituted with an amino acid that is not Gly (e.g., Ala, Arg, Asn, Asp, Cys, Glu, Gln, His, Ile, Leu, Lys, Met, Phe, Pro, Ser, Thr, Trp, Tyr, or Val), and the amino acid substitution results in a lower frequency of deamidation as compared to deamidation of VP1 and/or VP3 of the parent AAV particle. In yet other embodiments, A35 of VP1 is substituted with Asn and results in a higher frequency of deamidation as compared to deamidation of VP1 of a parent particle.

As used herein "N-acetylation" refers to a process whereby an acetyl group is covalently added to the amino group of the N-terminal amino acid of a protein. Typically, N-terminal acetyltransferases (NATs) transfer an acetyl group from acetyl-coenzyme A (Ac-CoA) to the α-amino group of the first amino acid residue of the protein.

As used here in, "deamidation" refers to a chemical reaction in which an amide functional group in the side chain of asparagine or glutamine is removed or converted to another functional group. For example, asparagine may be converted to aspartic acid or isoaspartic acid. In other examples, glutamine is converted to glutamic acid or pyroglutamic acid (5-oxoproline).

In some embodiments, the AAV particle is N-acetylated to a higher extent compared to a parental AAV capsid protein. In some embodiments, the AAV particle comprises more than about any of 5%, 10%, 15%, 20%, 25%, 30%, 35%, 40%, 45%, 50%, 55%, 60%, 65%, 70%, 75%, 80%, 85%, 90%, 95%, or 100% more N-acetyl groups compared to a parent AAV particle. In some embodiments, the AAV particle comprises between about any of 5%-10%, 10%-15%, 15%-20%, 20%-25%, 25%-30%, 30%-35%, 35%-40%, 40%-55%, 45%-50%, 50%-55%, 55%-60%, 60%-65%, 65%-70%, 70%-75%, 75%-80%, 80%-85%, 85%-90%, 90%-95%, 95%-100%, 5-25%, 25-50%, 50-75%, 75%-100%, 5-50% or 50%-100% more N-acetyl groups compared to a parent AAV particle. In some embodiments, the AAV particle comprises more than about any of 2-fold, 3-fold, 4-fold, 5-fold, 10-fold, 25-fold, 50-fold, 100-fold, 500-fold, or 1000-fold more N-acetyl groups compared to a parent AAV particle. In some embodiments, the AAV particle comprises between about any of 2-fold to 3-fold, 3-fold to 4-fold, 4-fold to 5-fold, 5-fold to 10-fold, 10-fold to 25-fold, 25-fold to 50-fold, 50-fold to 100-fold, 100-fold to 500-fold, 500-fold to 1000-fold, 2-fold to 10-fold, 10-fold to 100-fold, or 100-fold to 1000-fold more N-acetyl groups compared to a parent AAV particle.

In some embodiments, the AAV particle N-acetylated to a lower extent compared to a parental AAV capsid protein. In some embodiments, the AAV particle comprises more than about any of 5%, 10%, 15%, 20%, 25%, 30%, 35%, 40%, 45%, 50%, 55%, 60%, 65%, 70%, 75%, 80%, 85%, 90%, 95%, or 100% less N-acetyl groups compared to a parent AAV particle. In some embodiments, the AAV particle comprises between about any of 5%-10%, 10%-15%, 15%-20%, 20%-25%, 25%-30%, 30%-35%, 35%-40%, 40%-55%, 45%-50%, 50%-55%, 55%-60%, 60%-65%, 65%-70%, 70%-75%, 75%-80%, 80%-85%, 85%-90%, 90%-95%, 95%-100%, 5-25%, 25-50%, 50-75%, 75%-100%, 5-50% or 50%-100% less N-acetyl groups compared to a parent AAV particle. In some embodiments, the AAV particle comprises more than about any of 2-fold, 3-fold, 4-fold, 5-fold, 10-fold, 25-fold, 50-fold, 100-fold, 500-fold, or 1000-fold less N-acetyl groups compared to a parent AAV particle. In some embodiments, the AAV particle comprises between about any of 2-fold to 3-fold, 3-fold to 4-fold, 4-fold to 5-fold, 5-fold to 10-fold, 10-fold to 25-fold, 25-fold to 50-fold, 50-fold to 100-fold, 100-fold to 500-fold, 500-fold to 1000-fold, 2-fold to 10-fold, 10-fold to 100-fold, or 100-fold to 1000-fold less N-acetyl groups compared to a parent AAV particle.

In some embodiments, the AAV particle is deamidated to a higher extent compared to a parental AAV particle. In some embodiments, the AAV particle is more than about any of 5%, 10%, 15%, 20%, 25%, 30%, 35%, 40%, 45%, 50%, 55%, 60%, 65%, 70%, 75%, 80%, 85%, 90%, 95%, or 100% more deamidated compared to a parent AAV particle. In some embodiments, the AAV particle is deamidated between about any of 5%-10%, 10%-15%, 15%-20%, 20%-25%, 25%-30%, 30%-35%, 35%-40%, 40%-55%, 45%-50%, 50%-55%, 55%-60%, 60%-65%, 65%-70%, 70%-75%, 75%-80%, 80%-85%, 85%-90%, 90%-95%, 95%-100%, 5-25%, 25-50%, 50-75%, 75%-100%, 5-50% or 50%-100% more than a parent AAV particle. In some embodiments, the AAV particle is deamidated more than about any of 2-fold, 3-fold, 4-fold, 5-fold, 10-fold, 25-fold, 50-fold, 100-fold, 500-fold, or 1000-fold compared to a parent AAV particle. In some embodiments, the AAV particle is deamidated between about any of 2-fold to 3-fold, 3-fold to 4-fold, 4-fold to 5-fold, 5-fold to 10-fold, 10-fold to 25-fold, 25-fold to 50-fold, 50-fold to 100-fold, 100-fold to 500-fold, 500-fold to 1000-fold, 2-fold to 10-fold, 10-fold to 100-fold, or 100-fold to 1000-fold more than a parent AAV particle.

In some embodiments, a capsid protein of AAV is deamidated to a lower extent compared to a parental AAV capsid protein. In some embodiments, the AAV particle is more than about any of 5%, 10%, 15%, 20%, 25%, 30%, 35%, 40%, 45%, 50%, 55%, 60%, 65%, 70%, 75%, 80%, 85%, 90%, 95%, or 100% less deamidated compared to a parent AAV particle. In some embodiments, the AAV particle is deamidated between about any of 5%-10%, 10%-15%, 15%-20%, 20%-25%, 25%-30%, 30%-35%, 35%-40%, 40%-55%, 45%-50%, 50%-55%, 55%-60%, 60%-65%, 65%-70%, 70%-75%, 75%-80%, 80%-85%, 85%-90%, 90%-95%, 95%-100%, 5-25%, 25-50%, 50-75%, 75%-100%, 5-50% or 50%-100% less than a parent AAV particle. In some embodiments, the AAV particle is deamidated more than about any of 2-fold, 3-fold, 4-fold, 5-fold, 10-fold, 25-fold, 50-fold, 100-fold, 500-fold, or 1000-fold less than a parent AAV particle. In some embodiments, the AAV particle is deamidated between about any of 2-fold to 3-fold, 3-fold to 4-fold, 4-fold to 5-fold, 5-fold to 10-fold, 10-fold to 25-fold, 25-fold to 50-fold, 50-fold to 100-fold, 100-fold to 500-fold, 500-fold to 1000-fold, 2-fold to 10-fold, 10-fold to 100-fold, or 100-fold to 1000-fold less than a parent AAV particle.

The invention provides any combination of N-acetylation and deamidation. For example, the AAV capsid protein may be N-acetylated to a higher extent than a parent AAV capsid protein and deamidated to a higher extent than a parent AAV capsid protein, the AAV capsid protein may be N-acetylated to a higher extent than a parent AAV capsid protein and deamidated to the same extent than a parent AAV capsid protein, the AAV capsid protein may be N-acetylated to a higher extent than a parent AAV capsid protein and deamidated to a lower extent than a parent AAV capsid protein, the AAV capsid protein may be N-acetylated to the same extent than a parent AAV capsid protein and deamidated to a higher extent than a parent AAV capsid protein, the AAV capsid protein may be N-acetylated to the same extent than a parent AAV capsid protein and deamidated to the same extent than a parent AAV capsid protein, the AAV capsid protein may be N-acetylated to the same extent than a parent AAV capsid protein and deamidated to a lower extent than a parent AAV capsid protein, the AAV capsid protein may be N-acetylated to a lower extent than a parent AAV capsid protein and deamidated to a higher extent than a parent AAV capsid protein, the AAV capsid protein may be N-acetylated to a lower extent than a parent AAV capsid protein and deamidated to the same extent than a parent AAV capsid protein, or the AAV capsid protein may be N-acetylated to a lower extent than a parent AAV capsid protein and deamidated to a lower extent than a parent AAV capsid protein.

IV. Vectors

In certain aspects, the invention relates to viral particles, suitable for use in any of the methods described herein, which may comprise AAV vectors (e.g., rAAV vectors) or vectors derived from another virus. In some embodiments, the viral particle comprises a vector encoding a heterologous nucleic acid, e.g., a heterologous transgene. In some embodiments, the AAV particle comprises an AAV vector genome encoding a heterologous nucleic acid, e.g., a heterologous transgene.

The present invention contemplates the use of a recombinant viral genome for introduction of one or more nucleic acid sequences encoding a therapeutic polypeptide and/or nucleic acid for packaging into a rAAV viral particle. The recombinant viral genome may include any element to establish the expression of the therapeutic polypeptide and/or nucleic acid, for example, a promoter, an ITR of the present disclosure, a ribosome binding element, terminator, enhancer, selection marker, intron, polyA signal, and/or origin of replication.

In some embodiments, the heterologous nucleic acid encodes a therapeutic polypeptide. A therapeutic polypeptide may, e.g., supply a polypeptide and/or enzymatic activity that is absent or present at a reduced level in a cell or organism. Alternatively, a therapeutic polypeptide may supply a polypeptide and/or enzymatic activity that indirectly counteracts an imbalance in a cell or organism. For example, a therapeutic polypeptide for a disorder related to buildup of a metabolite caused by a deficiency in a metabolic enzyme or activity may supply a missing metabolic enzyme or activity, or it may supply an alternate metabolic enzyme or activity that leads to reduction of the metabolite. A therapeutic polypeptide may also be used to reduce the activity of a polypeptide (e.g., one that is overexpressed, activated by a gain-of-function mutation, or whose activity is otherwise misregulated) by acting, e.g., as a dominant-negative polypeptide.

The nucleic acids of the invention may encode polypeptides that are intracellular proteins, anchored in the cell membrane, remain within the cell, or are secreted by the cell transduced with the vectors of the invention. For polypeptides secreted by the cell that receives the vector; the polypeptide can be soluble (i.e., not attached to the cell). For example, soluble polypeptides are devoid of a transmembrane region and are secreted from the cell. Techniques to identify and remove nucleic acid sequences which encode transmembrane domains are known in the art.

The nucleic acids if the invention (e.g. the AAV vector genome) may comprise as a transgene, a nucleic acid encoding a protein or functional RNA that modulates or treats a CNS-associated disorder. The following is a non-limiting list of genes associated with CNS-associated disorders: neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TM, GTP-cyclohydrolase (GTPCH), aspartoacylase (ASPA), superoxide dismutase (SOD1), an anti-oxidant, an anti-angiogenic polypeptide, an anti-inflammatory polypeptide, and amino acid decorboxylase (AADC). For example, a useful transgene in the treatment of Parkinson's disease encodes TH, which is a rate limiting enzyme in the synthesis of dopamine. A transgene encoding GTPCII, which generates the TII cofactor tetrahydrobiopterin, may also be used in the treatment of Parkinson's disease. A transgene encoding GDNF or BDNF, or AADC, which facilitates conversion of L-Dopa to DA, may also be used for the treatment of Parkinson's disease. For the treatment of ALS, a useful transgene may encode: GDNF, BDNF or CNTF. Also for the treatment of ALS, a useful transgene may encode a functional RNA, e.g., shRNA, miRNA, that inhibits the expression of SOD1. For the treatment of ischemia a useful transgene may encode NAIP or NGF. A transgene encoding Beta-glucuronidase (GUS) may be useful for the treatment of certain lysosomal storage diseases (e.g., Mucopolysacharidosis type VII (MPS VII)). A transgene encoding a prodrug activation gene, e.g., HSV-Thymidine kinase which converts ganciclovir to a toxic nucleotide which disrupts DNA synthesis and leads to cell death, may be useful for treating certain cancers, e.g., when administered in combination with the prodrug. A transgene encoding an endogenous opioid, such a β-endorphin may be useful for treating pain. Examples of antioxidants include without limitation SOD1; SOD2; Catalase; Sirtuins 1, 3, 4, or 5; NRF2; PGC1a; GCL (catalytic subunit); GCL (modifier subunit); adiponectin; glutathione peroxidase 1; and neuroglobin. Examples of anti-angiogenic polypeptides include without limitation angiostatin, endostatin, PEDF, a soluble VEGF receptor, and a soluble PDGF receptor. Examples of anti-inflammatory polypeptides include without limitation IL-10, soluble IL17R, soluble TNF-R, TNF-R-Ig, an IL-1 inhibitor, and an IL18 inhibitor. Other examples of transgenes that may be used in the rAAV vectors of the invention will be apparent to the skilled artisan (See, e.g., Costantini L C, et al., *Gene Therapy* (2000) 7, 93-109).

In some embodiments, the heterologous nucleic acid encodes a therapeutic nucleic acid. In some embodiments, a therapeutic nucleic acid may include without limitation an siRNA, an shRNA, an RNAi, a miRNA, an antisense RNA, a ribozyme or a DNAzyme. As such, a therapeutic nucleic acid may encode an RNA that when transcribed from the nucleic acids of the vector can treat a disorder by interfering with translation or transcription of an abnormal or excess protein associated with a disorder of the invention. For example, the nucleic acids of the invention may encode for an RNA which treats a disorder by highly specific elimination or reduction of mRNA encoding the abnormal and/or excess proteins. Therapeutic RNA sequences include RNAi, small inhibitory RNA (siRNA), micro RNA (miRNA), and/or ribozymes (such as hammerhead and hairpin ribozymes) that can treat disorders by highly specific elimination or reduction of mRNA encoding the abnormal and/or excess proteins.

In some embodiments, the therapeutic polypeptide or therapeutic nucleic acid is used to treat a disorder of the CNS. Without wishing to be bound by theory, it is thought that a therapeutic polypeptide or therapeutic nucleic acid may be used to reduce or eliminate the expression and/or activity of a polypeptide whose gain-of-function has been associated with a disorder, or to enhance the expression and/or activity of a polypeptide to complement a deficiency that has been associated with a disorder (e.g., a mutation in a gene whose expression shows similar or related activity). Non-limiting examples of disorders of the invention that may be treated by a therapeutic polypeptide or therapeutic nucleic acid of the invention (exemplary genes that may be targeted or supplied are provided in parenthesis for each disorder) include stroke (e.g., caspase-3, Beclin1, Ask1, PAR1, HIF1α, PUMA, and/or any of the genes described in Fukuda, A. M. and Badaut, J. (2013) *Genes (Basel)* 4:435-456), Huntington's disease (mutant HTT), epilepsy (e.g., SCN1A, NMDAR, ADK, and/or any of the genes described in Boison, D. (2010) *Epilepsia* 51:1659-1668), Parkinson's disease (alpha-synuclein), Lou Gehrig's disease (also known as amyotrophic lateral sclerosis; SOD1), Alzheimer's disease (tau, amyloid precursor protein), corticobasal degeneration or CBD (tau), corticogasal ganglionic degeneration or CBGD (tau), frontotemporal dementia or FTD (tau), progressive supranuclear palsy or PSP (tau), multiple system atrophy or MSA (alpha-synuclein), cancer of the brain (e.g., a mutant or overexpressed oncogene implicated in brain cancer), and lysosomal storage diseases (LSD). Disorders of the invention may include those that involve large areas of the cortex, e.g., more than one functional area of the cortex, more than one lobe of the cortex, and/or the entire cortex. Other non-limiting examples of disorders of the invention that may be treated by a therapeutic polypeptide or therapeutic nucleic acid of the invention include traumatic brain injury, enzymatic dysfunction disorders, psychiatric disorders (including post-traumatic stress syndrome), neurodegenerative diseases, and cognitive disorders (including dementias, autism, and depression). Enzymatic dysfunction disorders include without limitation leukodystrophies (including Canavan's disease) and any of the lysosomal storage diseases described below.

In some embodiments, the therapeutic polypeptide or therapeutic nucleic acid is used to treat a lysosomal storage disease. As is commonly known in the art, lysosomal storage disease are rare, inherited metabolic disorders characterized by defects in lysosomal function. Such disorders are often caused by a deficiency in an enzyme required for proper mucopolysaccharide, glycoprotein, and/or lipid metabolism, leading to a pathological accumulation of lysosomally stored cellular materials. Non-limiting examples of lysosomal storage diseases of the invention that may be treated by a therapeutic polypeptide or therapeutic nucleic acid of the invention (exemplary genes that may be targeted or supplied are provided in parenthesis for each disorder) include Gaucher disease type 2 or type 3 (acid beta-glucosidase, GBA), GM1 gangliosidosis (beta-galactosidase-1, GLB1), Hunter disease (iduronate 2-sulfatase, IDS), Krabbe disease (galactosylceramidase, GALC), a mannosidosis disease (a mannosidase, such as alpha-D-mannosidase, MAN2B1), β mannosidosis disease (beta-mannosidase, MANBA), metachromatic leukodystrophy disease (pseudoarylsulfatase A, ARSA), mucolipidosisII/III disease (N-acetylglucosamine-1-phosphotransferase, GNPTAB), Niemann-Pick A disease (acid sphingomyelinase, ASM), Niemann-Pick C disease (Niemann-Pick C protein, NPC1), Pompe disease (acid alpha-1,4-glucosidase, GAA), Sandhoff disease (hexosaminidase beta subunit, HEXB), Sanfilippo A disease (N-sulfoglucosamine sulfohydrolase, MPS3A), Sanfilippo B disease (N-alpha-acetylglucosaminidase, NAGLU), Sanfilippo C disease (heparin acetyl-CoA:alpha-glucosaminidase N-acetyltransferase, MPS3C), Sanfilippo D disease (N-acetylglucosamine-6-sulfatase, GNS), Schindler disease (alpha-N-acetylgalactosaminidase, NAGA), Sly disease (beta-glucuronidase, GUSB), Tay-Sachs disease (hexosaminidase alpha subunit, HEXA), and Wolman disease (lysosomal acid lipase, LIPA).

Additional lysosomal storage diseases, as well as the defective enzyme associated with each disease, are listed in Table 1 below. In some embodiments, a disease listed in the table below is treated by a therapeutic polypeptide or therapeutic nucleic acid of the invention that complements or otherwise compensates for the corresponding enzymatic defect.

TABLE 1

Lysosomal storage disorders and associated defective enzymes.

| Lysosomal storage disease | Defective enzyme |
|---|---|
| Aspartylglusoaminuria | Aspartylglucosaminidase |
| Fabry | Alpha-galactosidase A |
| Infantile Batten Disease (CNL1) | Palmitoyl protein thioesterase |
| Classic Late Infantile Batten Disease (CNL2) | Tripeptidyl peptidase |
| Juvenile Batten Disease (CNL3) | Lysosomal transmembrane protein |
| Batten, other forms (CNL4-CNL8) | multiple gene products |
| Cystinosis | Cysteine transporter |
| Farber | Acid ceramidase |
| Fucosidosis | Acid alpha-L-fucosidase |
| Galactosidosialidosis | Protective protein/cathepsin A |

TABLE 1-continued

Lysosomal storage disorders and associated defective enzymes.

| Lysosomal storage disease | Defective enzyme |
| --- | --- |
| Gaucher types 1, 2, and 3 | Acid beta-glucosidase |
| GM1 gangliosidosis | Acid beta-galactosidase |
| Hunter | Iduronate-2-sulfatase |
| Hurler-Scheie | Alpha-L-iduronidase |
| Krabbe | Galactocerebrosidase |
| alpha-mannosidosis | Acid alpha-mannosidase |
| beta-mannosidosis | Acid beta-mannosidase |
| Maroteaux-Lamy | Arylsulfatase B |
| Metachromatic leukodystrophy | Arylsulfatase A |
| Morquio A | N-acetylgalactosamine-6-sulfate |
| Morquio B | Acid beta-galactosidase |
| Mucolipidosis II/III | N-acetylglucosamine-1-phosphotransferase |
| Niemann-Pick A, B | Acid sphingomyelinase |
| Niemann-Pick C | NPC-1 |
| Pompe acid | alpha-glucosidase |
| Sandhoff | beta-hexosaminidase B |
| Sanfilippo A | Heparan N-sulfatase |
| Sanfilippo B | alpha-N-acetylglucosaminidase |
| Sanfilippo C | Acetyl-CoA:alpha-glucoasaminide N-acetyltransferase |
| Sanfilippo D | N-acetylglucosamine-6-sulfate |
| Schindler disease | alpha-N-acetylgalactosaminidase |
| Schindler-Kanzaki | alpha-N-acetylgalactosaminidase |
| Sialidosis | alpha-neuramidase |
| Sly | beta-glucuronidase |
| Tay-Sachs | beta-hexosaminidase A |
| Wolman | Acid lipase |

In some embodiments, the heterologous nucleic acid is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., Gene, 1991, 108(2):193-9) and the elongation factor 1-alpha promoter (EF1-alpha) promoter (Kim et al., Gene, 1990, 91(2):217-23 and Guo et al., Gene Ther., 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides a recombinant vector comprising nucleic acid encoding a heterologous transgene of the present disclosure operably linked to a CBA promoter. Exemplary promoters and descriptions may be found, e.g., in U.S. PG Pub. 20140335054.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the 13-actin promoter, the phosphoglycerol kinase (PGK) promoter, and the EF1a promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art.

In some embodiments, the vector comprises an intron. For example, in some embodiments, the intron is a chimeric intron derived from chicken beta-actin and rabbit beta-globin. In some embodiments, the intron is a minute virus of mice (MVM) intron.

In some embodiments, the vector comprises a polyadenylation (polyA) sequence. Numerous examples of polyadenylation sequences are known in the art, such as a bovine growth hormone (BGH) Poly(A) sequence (see, e.g., accession number EF592533), an SV40 polyadenylation sequence, and an HSV TK pA polyadenylation sequence.

V. Viral Particles and Methods of Producing Viral Particles

Certain aspects of the present disclosure relate to recombinant viral particles (e.g., rAAV particles).

Based on the guidance provided herein, the techniques of the present disclosure may suitably be adapted by one of skill in the art for use with a variety of different viruses.

In some embodiments, the virus is of the family Adenoviridae, which includes non-enveloped viruses typically known as Adenoviruses. In some embodiments, the virus is of the genus *Atadenovirus, Aviadenovirus, Ichtadenovirus, Mastadenovirus*, or *Siadenovirus*.

In some embodiments, the virus is of the family Parvoviridae, which includes non-enveloped viruses such as AAV and Bocaparvovirus. In some embodiments, the virus is of the subfamily Densovirinae. In some embodiments, the virus is of the genus *Ambidensovirus, Brevidensovirus, Hepandensovirus, Iteradensovirus,* or *Penstyldensovirus.* In some embodiments, the virus is of the subfamily Parvovirinae. In some embodiments, the virus is of the genus *Amdoparvovirus, Aveparvovirus, Bocaparvovirus, Copiparvovirus, Dependoparvovirus, Erythroparvovirus, Protoparvovirus,* or *Tetraparvovirus.*

In some embodiments, the virus is of the family Retroviridae, which includes enveloped viruses including lentivirus. In some embodiments, the virus is of the subfamily Orthoretrovirinae. In some embodiments, the virus is of the genus *Alpharetrovirus, Betaretrovirus, Deltaretrovirus, Epsilonretrovirus, Gammaretrovirus,* or *Lentivirus.* In some embodiments, the virus is of the subfamily Spumaretrovirinae. In some embodiments, the virus is of the genus *Spumavirus.*

In some embodiments, the virus is of the family Baculoviridae, which includes enveloped viruses including alphabaculovirus. In some embodiments, the virus is of the genus *Alphabaculovirus, Betabaculovirus, Deltabaculovirus,* or *Gammabaculovirus.*

In some embodiments, the virus is of the family Herpesviridae, which includes enveloped viruses such as the simplex viruses HSV-1 and HSV-2. In some embodiments, the virus is of the subfamily Alphaherpesvirinae. In some embodiments, the virus is of the genus *Iltovirus, Mardivirus, Simplexvirus,* or *Varicellovirus.* In some embodiments, the virus is of the subfamily Betaherpesvirinae. In some embodiments, the virus is of the genus *Cytomegalovirus, Muromegalovirus, Proboscivirus,* or *Roseolovirus.* In some embodiments, the virus is of the subfamily Gammaherpesvirinae. In some embodiments, the virus is of the genus *Lymphocryptovirus, Macavirus, Percavirus,* or *Rhadinovirus.*

In some embodiments, the virus is an AAV virus. In an AAV particle, a nucleic acid is encapsidated in the AAV particle. The AAV particle also comprises capsid proteins. In some embodiments, the nucleic acid comprises a heterologous nucleic acid and/or one or more of the following components, operatively linked in the direction of transcription, control sequences including transcription initiation and termination sequences, thereby forming an expression cassette.

In some embodiments, the viral particle comprises an AAV ITR sequence. For example, an expression cassette may be flanked on the 5' and 3' end by at least one functional AAV ITR sequence. By "functional AAV ITR sequences" it is meant that the ITR sequences function as intended for the rescue, replication and packaging of the AAV virion. See Davidson et al., *PNAS,* 2000, 97(7) 3428-32; Passini et al., *J. Virol.,* 2003, 77(12):7034-40; and Pechan et al., *Gene Ther.,* 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.,* 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS,* 2002, 99(18): 11854-6; Gao et al., *PNAS,* 2003, 100(10):6081-6; and Bossis et al., *J. Virol.,* 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV DJ, AAV DJ8, a goat AAV, bovine AAV, or mouse AAV ITRs or the like. In some embodiments, the nucleic acid in the AAV (e.g., an rAAV vector) comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV DJ, AAV DJ8, a goat AAV, bovine AAV, or mouse AAV ITRs or the like. In some embodiments, the AAV particle comprises an AAV vector encoding a heterologous transgene flanked by one or more AAV ITRs.

In some embodiments, a rAAV particle comprises an encapsulation protein selected from AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV LK03 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, an AAV2HBKO capsid, an AAVPHP.B capsid or an AAVPHP.eB capsid, or an AAV capsid described in U.S. Pat. No. 8,283,151 or International Publication No. WO/2003/042397. In further embodiments, a rAAV particle comprises capsid proteins of an AAV serotype from Clades A-F.

Certain aspects of the present disclosure relate to an AAV (e.g., a rAAV) capsid protein comprising an amino acid substitution at amino acid residue 2. In some embodiments, the amino acid substitution at amino acid residue 2 alters N-terminal acetylation compared to N-terminal acetylation at amino acid residue 2 of the parent AAV capsid protein. As described herein, the amino acid at the $2^{nd}$ position to the initiating methionine (iMet X) of an AAV capsid protein may be examined for effects on N-terminal acetylation, trafficking, transduction, and/or other post-translational modification(s) (e.g., glycosylation, ubiquitination, and so forth). Any assay described herein for examining acetylation, or a functional consequence thereof related to AAV particles, may be used to assess N-terminal acetylation. In some embodiments, amino acid residue 2 of the AAV capsid protein (e.g., VP1 or VP3) is substituted with Cys, Ser, Thr, Val, Gly, Asn, Asp, Glu, Ile, Leu, Phe, Gln, Lys, Met, Pro or Tyr. In some embodiments, the amino acid substitution results in less deamidation of the AAV capsid.

Other aspects of the present disclosure relate to an AAV (e.g., a rAAV) capsid protein comprising an amino acid substitution that alters deamidation. In some embodiments, an amino acid substitution (e.g., an amino acid substitution at A35 of VP1, N57 of VP1, G58 of VP1, N382 of VP3, G383 of VP3, N511 of VP3, G512 of VP3, N715 of VP3, or G716 of VP3) that "alters" deamidation results in a higher frequency of deamidation or a lower frequency of deamidation, e.g., as compared to a VP1 or VP3 without the substitution, such as the parental VP1 or VP3. As described herein, a potential deamidation site of an AAV capsid protein (e.g., VP1 or VP3) may be examined for effects on deamidation, trafficking, transduction, and/or other post-translational modification(s) (e.g., glycosylation, ubiquitination, and so forth). Any assay described herein for examining deamidation, or a functional consequence thereof related to AAV particles, may be used to assess deamidation.

Several potential deamidation sites are described herein. In some embodiments, an amino acid substitution that alters deamidation is selected from A35 of VP1, N57 of VP1, G58 of VP1, N382 of VP3, G383 of VP3, N511 of VP3, G512 of VP3, N715 of VP3, or G716 of VP3. For example, in some embodiments, N57 of VP1, N382 of VP3, N511 of VP3, and/or N715 of VP3 is substituted with Asp, and the amino acid substitution results in a higher frequency of deamidation as compared to deamidation of VP1 and/or VP3 of the parent AAV particle. In other embodiments, the amino acid substitution is N57K or N57Q, and the amino acid substitution results in a lower frequency of deamidation as compared to deamidation of VP1 and/or VP3 of the parent AAV particle. In yet other embodiments, G58 of VP1, G383 of VP3, G512 of VP3, and/or G716 of VP3 is substituted with an amino acid that is not Gly (e.g., Ala, Arg, Asn, Asp, Cys, Glu, Gln, His, Ile, Leu, Lys, Met, Phe, Pro, Ser, Thr, Trp, Tyr, or Val), and the amino acid substitution results in a lower frequency of deamidation as compared to deamidation of VP1 and/or VP3 of the parent AAV particle.

In some embodiments, the AAV capsid protein is VP1, VP2, or VP3. The AAV particle may comprise any of the exemplary AAV capsid serotypes described herein, such as AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, AAV DJ8, AAV2 N587A, AAV2 E548A, AAV2 N708A, AAV V708K, goat AAV, AAV1/AAV2 chimeric, bovine AAV, mouse AAV, or rAAV2/HBoV1. The AAV capsid protein may further comprise any of the capsid protein mutations described herein, such as tyrosine and/or heparin binding mutations.

Other aspects of the present disclosure relate to methods of improving the stability of a rAAV particle. In some embodiments, the methods include substituting amino acid residue 2 of VP1 and/or VP3, e.g., as described herein. For example, in some embodiments, amino acid residue 2 of VP1 is substituted. In other embodiments, amino acid residue 2 of VP3 is substituted. In some embodiments, the substituted amino acid at position 2 is N-acetylated at a higher frequency than amino acid residue 2 of the parent VP1 and/or VP3, e.g., as described herein. In some embodiments, substituting amino acid residue 2 of VP1 and/or VP3 improves the stability of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the stability of a rAAV particle with a substituted amino acid at position 2 may be compared to a wild-type or parental AAV capsid, e.g., of the same serotype. For example, in some embodiments, substituting amino acid residue 2 of VP1 and/or VP3 improves the stability of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to stability of a rAAV particle comprising a wild-type capsid. AAV particle stability may be measured using various assays known in the art, including without limitation differential scanning fluorescence (DSF), differential scanning calorimetry (DSC), other thermal denaturation assays, susceptibility to proteolysis, imaging or structural analysis to observe denaturation (e.g., using electron microscopy), transduction efficiency or another functional assay on AAV particle compositions kept for a designated time interval at a particular temperature (e.g., room temperature, or 4° C., for thermal stability) or treated at a particular pH (e.g., pH stability), and the like.

Other aspects of the present disclosure relate to methods of improving the assembly of a rAAV particle. In some embodiments, the methods include substituting amino acid residue 2 of VP1 and/or VP3, e.g., as described herein. For example, in some embodiments, amino acid residue 2 of VP1 is substituted. In other embodiments, amino acid residue 2 of VP3 is substituted. In some embodiments, the substituted amino acid at position 2 is N-acetylated at a higher frequency than amino acid residue 2 of the parent VP1 and/or VP3, e.g., as described herein. In some embodiments, substituting amino acid residue 2 of VP1 and/or VP3 improves the assembly of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the assembly of a rAAV particle with a substituted amino acid at position 2 may be compared to a wild-type or parental AAV capsid, e.g., of the same serotype. For example, in some embodiments, substituting amino acid residue 2 of VP1 and/or VP3 improves the assembly of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to assembly of a rAAV particle comprising a wild-type capsid. AAV particle assembly may be measured using various assays known in the art, including without limitation, measuring particle production amount and/or rate, quantifying capsid production (e.g., after purification using any of the methods described herein), assaying production of complete vectors vs. empty capsids, measuring transduction efficiency, imaging or structural analysis to observe particle formation (e.g., using electron microscopy), production of AAV capsid proteins (e.g., as assayed by Western blotting), and the like.

Other aspects of the present disclosure relate to methods of improving the transduction of a rAAV particle. In some embodiments, the methods include substituting amino acid residue 2 of VP1 and/or VP3, e.g., as described herein. For example, in some embodiments, amino acid residue 2 of VP1 is substituted. In other embodiments, amino acid residue 2 of VP3 is substituted. In some embodiments, the substituted amino acid at position 2 is N-acetylated at a higher frequency than amino acid residue 2 of the parent VP1 and/or VP3, e.g., as described herein. In some embodiments, substituting amino acid residue 2 of VP1 and/or VP3 improves the transduction of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the transduction of a rAAV particle with a substituted amino acid at position 2 may be compared to a wild-type or parental AAV capsid, e.g., of the same serotype. For example, in some embodiments, substituting amino acid residue 2 of VP1 and/or VP3 improves the transduction of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to transduction of a rAAV particle comprising a wild-type capsid. AAV particle transduction may be measured using various assays known in the art, including without limitation, the transduction efficiency assays described herein. In some embodiments, the invention provide methods of reducing the transduction of a rAAV particle; for example, by substituting amino acid residue 2 of VP1 and/or VP3.

Other aspects of the present disclosure relate to methods of improving the stability of a rAAV particle. In some embodiments, the methods include substituting an amino acid of VP1 and/or VP3 that alters deamidation, e.g., as described herein. For example, in some embodiments, A35 of VP1, N57 of VP1, G58 of VP1, N382 of VP3, G383 of VP3, N511 of VP3, G512 of VP3, N715 of VP3, or G716 of VP3 is substituted. In some embodiments, the substituted amino acid is deamidated at a higher frequency than the amino acid residue of the parent VP1 and/or VP3, e.g., as described herein. In some embodiments, substituting A35 of VP1, N57 of VP1, G58 of VP1, N382 of VP3, G383 of VP3, N511 of VP3, G512 of VP3, N715 of VP3, and/or G716 of VP3 improves the stability of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the stability of a rAAV particle with a substituted A35 of VP1, N57 of VP1, G58 of VP1, N382 of VP3, G383 of VP3, N511 of VP3, G512 of VP3, N715 of VP3, or G716 of VP3 may be compared to a wild-type or parental AAV capsid, e.g., of the same serotype. For example, in some embodiments, substituting A35 of VP1, N57 of VP1, G58 of VP1, N382 of VP3, G383 of VP3, N511 of VP3, G512 of VP3, N715 of VP3, and/or G716 of VP3 improves the stability of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to stability of a rAAV particle comprising a wild-type capsid. AAV particle stability may be measured using various assays known in the art, including without limitation differential scanning fluorescence (DSF), differential scanning calorimetry (DSC), other thermal denaturation assays, susceptibility to proteolysis, imaging or structural analysis to observe denaturation (e.g., using electron microscopy), transduction efficiency or another functional assay on AAV particle compositions kept for a designated time interval at a particular temperature (e.g., room temperature, or 4° C., for thermal stability) or treated at a particular pH (e.g., pH stability), and the like.

Other aspects of the present disclosure relate to methods of improving the assembly of a rAAV particle. In some embodiments, the methods include substituting an amino acid of VP1 and/or VP3 that alters deamidation, e.g., as described herein. For example, in some embodiments, A35 of VP1, N57 of VP1, G58 of VP1, N382 of VP3, G383 of VP3, N511 of VP3, G512 of VP3, N715 of VP3, or G716 of VP3 is substituted. In some embodiments, the substituted amino acid is deamidated at a higher frequency than the amino acid residue of the parent VP1 and/or VP3, e.g., as described herein. In some embodiments, substituting A35 of VP1, N57 of VP1, G58 of VP1, N382 of VP3, G383 of VP3, N511 of VP3, G512 of VP3, N715 of VP3, and/or G716 of VP3 improves the assembly of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the stability of a rAAV particle with a substituted A35 of VP1, N57 of VP1, G58 of VP1, N382 of VP3, G383 of VP3, N511 of VP3, G512 of VP3, N715 of VP3, or G716 of VP3 may be compared to a wild-type or parental AAV capsid, e.g., of the same serotype. For example, in some embodiments, substituting A35 of VP1, N57 of VP1, G58 of VP1, N382 of VP3, G383 of VP3, N511 of VP3, G512 of VP3, N715 of VP3, and/or G716 of VP3 improves the assembly of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to assembly of a rAAV particle comprising a wild-type capsid. AAV particle assembly may be measured using various assays known in the art, including without limitation, measuring particle production amount and/or rate, quantifying capsid production (e.g., after purification using any of the methods described herein), assaying production of complete vectors vs. empty capsids, measuring transduction efficiency, imaging or structural analysis to observe particle formation (e.g., using electron microscopy), production of AAV capsid proteins (e.g., as assayed by Western blotting), and the like.

Other aspects of the present disclosure relate to methods of improving the transduction of a rAAV particle. In some embodiments, the methods include substituting an amino acid of VP1 and/or VP3 that alters deamidation, e.g., as described herein. For example, in some embodiments, A35 of VP1, N57 of VP1, G58 of VP1, N382 of VP3, G383 of VP3, N511 of VP3, G512 of VP3, N715 of VP3, or G716 of VP3 is substituted. In some embodiments, the substituted amino acid is deamidated at a higher frequency than the amino acid residue of the parent VP1 and/or VP3, e.g., as described herein. In some embodiments, substituting A35 of VP1, N57 of VP1, G58 of VP1, N382 of VP3, G383 of VP3, N511 of VP3, G512 of VP3, N715 of VP3, and/or G716 of VP3 improves the transduction of a rAAV particle by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the stability of a rAAV particle with a substituted A35 of VP1, N57 of VP1, G58 of VP1, N382 of VP3, G383 of VP3, N511 of VP3, G512 of VP3, N715 of VP3, or G716 of VP3 may be compared to a wild-type or parental AAV capsid, e.g., of the same serotype. For example, in some embodiments, substituting A35 of VP1, N57 of VP1, G58 of VP1, N382 of VP3, G383 of VP3, N511 of VP3, G512 of VP3, N715 of VP3, and/or G716 of VP3 improves the transduction of a rAAV particle by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, e.g., as compared to transduction of a rAAV particle comprising a wild-type capsid. AAV particle transduction may be measured using various assays known in the art, including without limitation, the transduction efficiency assays described herein.

In some aspects, the invention provides viral particles comprising a recombinant self-complementing genome (e.g., a self-complementary or self-complimenting rAAV vector). AAV viral particles with self-complementing vector genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a heterologous nucleic acid). In some embodiments, the vector comprises a first nucleic acid sequence encoding a heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence and a second heterologous nucleic acid sequence are linked by a mutated ITR (e.g., the right ITR). In some embodiments, the ITR comprises the polynucleotide sequence 5'-CACTCCCTCTCTGCGCGCTCGCTCGCT-CACTGAGGCC GGGCGACCAAAGGTCGCC-CACGCCCGGGCTTTGCCCGGGCG-3' (SEQ ID NO:8). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, a rAAV particle may contain one or more ITRs and capsid derived from the same AAV serotype, or a rAAV particle may contain one or more ITRs derived from a different AAV serotype than capsid of the rAAV particle.

In some embodiments, the AAV capsid comprises a mutation, e.g., the capsid comprises a mutant capsid protein. In some embodiments, the mutation is a tyrosine mutation or a heparin binding mutation. In some embodiments, a mutant capsid protein maintains the ability to form an AAV capsid. In some embodiments, the rAAV particle comprises an AAV2 or AAV5 tyrosine mutant capsid (see, e.g., Zhong L. et al., (2008) *Proc Natl Acad Sci USA* 105(22):7827-7832), such as a mutation in Y444 or Y730 (numbering according to AAV2). In further embodiments, the rAAV particle comprises capsid proteins of an AAV serotype from Clades A-F (Gao, et al., *J. Virol.* 2004, 78(12):6381).

In some embodiments, a capsid protein comprises one or more amino acid substitutions at one or more positions that interact with a heparin sulfate proteoglycan or at one or more positions corresponding to amino acids 484, 487, 527, 532, 585 or 588, numbering based on VP1 numbering of AAV2. Heparan sulfate proteoglycan (HSPG) is known in the art to act as the cellular receptor for AAV2 particles (Summerford, C. and Samulski, R. J. (1998) *J. Virol.* 72(2):1438-45). Binding between an AAV2 particle and HSPG at the cell membrane serves to attach the particle to the cell. Other cell surface proteins such as fibroblast growth factor receptor and αvβ5 integrin may also facilitate cellular infection. After binding, an AAV2 particle may enter the cell through mechanisms including receptor mediated endocytosis via clathrin-coated pits. An AAV2 particle may be released from an endocytic vesicle upon endosomal acidification. This allows the AAV2 particle to travel to the perinuclear region and then the cell nucleus. AAV3 particles are also known to bind heparin (Rabinowitz, J. E., et al. (2002) *J. Virol.* 76(2):791-801).

The binding between AAV2 capsid proteins and HSPG is known to occur via electrostatic interactions between basic AAV2 capsid protein residues and negatively charged glycosaminoglycan residues (Opie, S R et al., (2003) *J. Virol.* 77:6995-7006; Kern, A et al., (2003) *J. Virol.* 77:11072-11081). Specific capsid residues implicated in these interactions include R484, R487, K527, K532, R585, and R588. Mutations in these residues have been shown to reduce AAV2 binding to Hela cells and heparin itself (Opie, S R et al., (2003) *J. Virol.* 77:6995-7006; Kern, A et al., (2003) *J. Virol.* 77:11072-11081; WO 2004/027019 A2, U.S. Pat. No. 7,629,322). Further, without wishing to be bound to theory, it is thought that amino acid substitution(s) at one or more of the residues corresponding to amino acids 484, 487, 527, 532, 585 or 588, numbering based on VP1 numbering of AAV2 may modulate the transduction properties of AAV capsid types that do not bind to HSPG, or may modulate the transduction properties of AAV capsid types independent from their ability to bind HSPG. In some embodiments, the one or more amino acid substitutions comprises a substitution at position R484, R487, K527, K532, R585 and/or R588 of VP1, VP2 and/or VP3, numbering based on VP1 of AAV2.

In some embodiments, the one or more amino acid substitutions reduce binding of the rAAV particle to the heparin sulfate proteoglycan by about at least 10%, about at least 25%, about at least 50%, about at least 75%, or about at least 100%. In some embodiments, the one or more amino acid substitutions reduce binding of the rAAV particle to the heparin sulfate proteoglycan by about at least 10%, about at least 15%, about at least 20%, about at least 25%, about at least 30%, about at least 35%, about at least 40%, about at least 45%, about at least 50%, about at least 55%, about at least 60%, about at least 65%, about at least 70%, about at least 75%, about at least 80%, about at least 85%, about at least 90%, about at least 95%, or about at least 100% (as compared to binding of a rAAV particle comprising a wild-type capsid). In some embodiments, the one or more amino acid substitutions reduce binding of the rAAV particle to the heparin sulfate proteoglycan by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, (as compared to binding of a rAAV particle comprising a wild-type capsid). In some embodiments, the one or more amino acid substitutions results in no detectable binding of the rAAV particle to the heparin sulfate proteoglycan compared to binding of a wild-type rAAV particle. Means to measure binding of AAV particles to HSPG are known in the art; e.g., binding to a heparin sulfate chromatography media or binding to a cell known to express HSPG on its surface. For example, see Opie, S R et al., (2003) *J. Virol.* 77:6995-7006 and Kern, A et al., (2003) *J. Virol.* 77:11072-11081. In some embodiments, the one or more amino acid substitutions improve the transduction efficiency of the rAAV particle to a cell (e.g., a cell in the eye or CNS) by about at least 10%, about at least 15%, about at least 20%, about at least 25%, about at least 30%, about at least 35%, about at least 40%, about at least 45%, about at least 50%, about at least 55%, about at least 60%, about at least 65%, about at least 70%, about at least 75%, about at least 80%, about at least 85%, about at least 90%, about at least 95%, or about at least 100% (as compared to transduction efficiency of a rAAV particle comprising a wild-type capsid). In some embodiments, the one or more amino acid substitutions improve the transduction efficiency of the rAAV particle to a cell (e.g., a cell in the eye or CNS) by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, (as compared to transduction efficiency of a rAAV particle comprising a wild-type capsid). Means to measure transduction efficiency of AAV particles to a cell (e.g., a cell in culture or part of a tissue) are known in the art. For example, a population of cells (e.g., in culture or part of a tissue) may be infected with a concentration of rAAV particles containing a vector that, when expressed in the cells, produces an assayable reporter (e.g., GFP fluorescence, sFLT production, etc.).

AAV Capsid Proteins

In some aspects, the invention provides an AAV capsid protein comprising an amino acid substitution at amino acid residue 2; wherein the amino acid substitution at amino acid residue 2 alters N-terminal acetylation compared to N-terminal acetylation at amino acid residue 2 of the parent AAV capsid protein. In some embodiments, the AAV capsid protein is VP1 or VP3. In some embodiments, amino acid residue 2 of the AAV capsid protein (e.g., VP1 or VP3) is substituted with Cys, Ser, Thr, Val, Gly, Asn, Asp, Glu, Ile, Leu, Phe, Gln, Lys, Met, Pro or Tyr. In some embodiments, the amino acid substitution results in less deamidation of the AAV capsid protein. Non-limiting examples of AAV capsid proteins of the invention include VP1 and/or VP3 of any of the following AAV serotypes: AAV1, AAV2, AAV3, AAV4, AAV5, AAV6, AAV7, AAV8, AAVrh8, AAVrh8R, AAV9, AAV10, AAVrh10, AAV11, AAV12, AAV LK03, AAV2R471A, AAV2/2-7m8, AAV DJ, AAV DJ8, AAV2 N587A, AAV2 E548A, AAV2 N708A, AAV V708K, goat AAV, AAV1/AAV2 chimeric, bovine AAV, mouse AAV, or rAAV2/HBoV1 serotype capsid. In some embodiments, the AAV capsid further comprises a tyrosine mutation or a heparin binding mutation.

Production of AAV Particles

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids (Urabe, M. et al., (2002) *Human Gene Therapy* 13(16):1935-1943; Kotin, R. (2011) *Hum Mol Genet.* 20(R1): R2-R6). rAAV production cultures for the production of rAAV viral particles all require; 1) suitable host cells, 2) suitable helper virus function, 3) AAV rep and cap genes and gene products; 4) a nucleic acid (such as a therapeutic nucleic acid) flanked by at least one AAV ITR sequences (e.g., an AAV genome encoding GNPTAB); and 5) suitable media and media components to support rAAV production. In some embodiments, the suitable host cell is a primate host cell. In some embodiments, the suitable host cell is a human-derived cell lines such as HeLa, A549, 293, or Perc.6 cells. In some embodiments, the suitable helper virus function is provided by wild-type or mutant adenovirus (such as temperature sensitive adenovirus), herpes virus (HSV), baculovirus, or a plasmid construct providing helper functions. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells). In some embodiments, the AAV cap functions provide an amino acid substitution at amino acid residue 2 of VP1 and/or VP3, wherein the amino acid substitution at amino acid residue 2 of VP1 and/or VP3 alters N-terminal acetylation compared to N-terminal acetylation at amino acid residue 2 of VP1 and/or VP3 of the parent AAV particle. In some embodiments, amino acid residue 2 of the AAV capsid protein (e.g., VP1 or VP3) is substituted with Cys, Ser, Thr, Val, Gly, Asn, Asp, Glu, Ile, Leu, Phe, Gln, Lys, Met, Pro or Tyr. In some embodiments, the amino acid substitution results in less deamidation of the AAV capsid.

One method for producing rAAV particles is the triple transfection method. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method (see Martin et al., (2013) *Human Gene Therapy Methods* 24:253-269; U.S. PG Pub. No. US2004/0224411; and Liu, X. L. et al. (1999) *Gene Ther.* 6:293-299). Briefly, a cell line (e.g., a HeLa, 293, A549, or Perc.6 cell line) may be stably transfected with a plasmid containing a rep gene, a capsid gene, and a vector genome comprising a promoter-heterologous nucleic acid sequence (e.g., GNPTAB). Cell lines may be screened to select a lead clone for rAAV production, which may then be expanded to a production bioreactor and infected with a helper virus (e.g., an adenovirus or HSV) to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions. As described herein, the producer cell line method may be advantageous for the production of rAAV particles with an oversized genome, as compared to the triple transfection method.

In some embodiments, the nucleic acid encoding AAV rep and cap genes and/or the rAAV genome are stably maintained in the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell on the same plasmid. In other embodiments, the AAV rep, AAV cap, and rAAV genome are introduced into a cell on different plasmids. In some embodiments, a cell line stably transfected with a plasmid maintains the plasmid for multiple passages of the cell line (e.g., 5, 10, 20, 30, 40, 50 or more than 50 passages of the cell). For example, the plasmid(s) may replicate as the cell replicates, or the plasmid(s) may integrate into the cell genome. A variety of sequences that enable a plasmid to replicate autonomously in a cell (e.g., a human cell) have been identified (see, e.g., Krysan, P. J. et al. (1989) *Mol. Cell Biol.* 9:1026-1033). In some embodiments, the plasmid(s) may contain a selectable marker (e.g., an antibiotic resistance marker) that allows for selection of cells maintaining the plasmid. Selectable markers commonly used in mammalian cells include without limitation blasticidin, G418, hygromycin B, zeocin, puromycin, and derivatives thereof. Methods for introducing nucleic acids into a cell are known in the art and include without limitation viral transduction, cationic transfection (e.g., using a cationic polymer such as DEAE-dextran or a cationic lipid such as lipofectamine), calcium phosphate transfection, microinjection, particle bombardment, electroporation, and nanoparticle transfection (for more details, see e.g., Kim, T. K. and Eberwine, J. H. (2010) *Anal. Bioanal. Chem.* 397:3173-3178).

In some embodiments, the nucleic acid encoding AAV rep and cap genes and/or the rAAV genome are stably integrated into the genome of the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell on the same plasmid. In other embodiments, the AAV rep, AAV cap, and rAAV genome are introduced into a cell on different plasmids. In some embodiments, the plasmid(s) may contain a selectable marker (e.g., an antibiotic resistance marker) that allows for selection of cells maintaining the plasmid. Methods for stable integration of nucleic acids into a variety of host cell lines are known in the art. For example, repeated selection (e.g., through use of a selectable marker) may be used to select for cells that have integrated a nucleic acid containing a selectable marker (and AAV cap and rep genes and/or a rAAV genome). In other embodiments, nucleic acids may be integrated in a site-specific manner into a cell line to generate a producer cell line. Several site-specific recombination systems are known in the art, such as FLP/FRT (see, e.g., O'Gorman, S. et al. (1991) *Science* 251:1351-1355), Cre/loxP (see, e.g., Sauer, B. and Henderson, N. (1988) *Proc. Natl. Acad. Sci.* 85:5166-5170), and phi C31-att (see, e.g., Groth, A. C. et al. (2000) *Proc. Natl. Acad. Sci.* 97:5995-6000).

In some embodiments, the producer cell line is derived from a primate cell line (e.g., a non-human primate cell line, such as a Vero or FRhL-2 cell line). In some embodiments, the cell line is derived from a human cell line. In some embodiments, the producer cell line is derived from HeLa, 293, A549, or PERC.6® (Crucell) cells. For example, prior to introduction and/or stable maintenance/integration of nucleic acid encoding AAV rep and cap genes and/or the oversized rAAV genome into a cell line to generate a producer cell line, the cell line is a HeLa, 293, A549, or PERC.6® (Crucell) cell line, or a derivative thereof.

In some embodiments, the producer cell line is adapted for growth in suspension. As is known in the art, anchorage-dependent cells are typically not able to grow in suspension without a substrate, such as microcarrier beads. Adapting a cell line to grow in suspension may include, for example, growing the cell line in a spinner culture with a stirring paddle, using a culture medium that lacks calcium and magnesium ions to prevent clumping (and optionally an antifoaming agent), using a culture vessel coated with a siliconizing compound, and selecting cells in the culture (rather than in large clumps or on the sides of the vessel) at each passage. For further description, see, e.g., ATCC frequently asked questions document (available on the world wide web at atcc.org/Global/FAQs/9/1/Adapting%20a%20monolayer%20cell%20line%20to%20suspension-40.aspx) and references cited therein.

Suitable AAV production culture media of the present invention may be supplemented with serum or serum-derived recombinant proteins at a level of 0.5%-20% (v/v or w/v). Alternatively, as is known in the art, AAV vectors may be produced in serum-free conditions which may also be referred to as media with no animal-derived products. One of ordinary skill in the art may appreciate that commercial or custom media designed to support production of AAV vectors may also be supplemented with one or more cell culture components know in the art, including without limitation glucose, vitamins, amino acids, and or growth factors, in order to increase the titer of AAV in production cultures.

AAV production cultures can be grown under a variety of conditions (over a wide temperature range, for varying lengths of time, and the like) suitable to the particular host cell being utilized. As is known in the art, AAV production cultures include attachment-dependent cultures which can be cultured in suitable attachment-dependent vessels such as, for example, roller bottles, hollow fiber filters, microcarriers, and packed-bed or fluidized-bed bioreactors. AAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

AAV vector particles of the invention may be harvested from AAV production cultures by lysis of the host cells of the production culture or by harvest of the spent media from the production culture, provided the cells are cultured under conditions known in the art to cause release of AAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In a further embodiment, the AAV particles are purified. The term "purified" as used herein includes a preparation of AAV particles devoid of at least some of the other components that may also be present where the AAV particles naturally occur or are initially prepared from. Thus, for example, isolated AAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the AAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 m Filter Opticap XL1O Millipore Express SHC Hydrophilic Membrane filter. Clarification can also be achieved by a variety of other standard techniques known in the art, such as, centrifugation or filtration through any cellulose acetate filter of 0.2 m or greater pore size known in the art.

In some embodiments, the AAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

AAV particles may be isolated or purified using one or more of the following purification steps: equilibrium centrifugation; flow-through anionic exchange filtration; tangential flow filtration (TFF) for concentrating the AAV particles; AAV capture by apatite chromatography; heat inactivation of helper virus; AAV capture by hydrophobic interaction chromatography; buffer exchange by size exclusion chromatography (SEC); nanofiltration; and AAV capture by anionic exchange chromatography, cationic exchange chromatography, or affinity chromatography. These steps may be used alone, in various combinations, or in different orders. In some embodiments, the method comprises all the steps in the order as described below. Methods to purify AAV particles are found, for example, in Xiao et al., (1998) *Journal of Virology* 72:2224-2232; U.S. Pat. Nos. 6,989,264 and 8,137,948; and WO 2010/148143.

Pharmaceutical Compositions

In some embodiments, an AAV particle of the present disclosure (e.g., a rAAV particle) is in a pharmaceutical composition. The pharmaceutical compositions may be suitable for any mode of administration described herein or known in the art. In some embodiments, the pharmaceutical composition comprises rAAV particles modified to improve the stability and/or improve the transduction efficiency of rAAV particles; for example, for use in substituting the amino acid residue at position 2 of VP1 and/or VP3 to improve acetylation of rAAV capsid proteins. In some embodiments, the pharmaceutical composition comprises rAAV particles modified to modulate the stability and/or the transduction efficiency of rAAV particles (e.g., increase stability and/or transduction efficiency or decrease stability and/or transduction efficiency); for example, for use in substituting the amino acid residues that modulate deamidation (e.g., increase deamidation or decrease deamidation).

In some embodiments, the rAAV particle is in a pharmaceutical composition comprising a pharmaceutically acceptable excipient. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). In some embodiments, the pharmaceutical composition comprising a rAAV particle described herein and a pharmaceutically acceptable carrier is suitable for administration to human. Such carriers are well known in the art (see, e.g., Remington's Pharmaceutical Sciences, 15th Edition, pp. 1035-1038 and 1570-1580).

Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

Kits and Articles of Manufacture

The present invention also provides kits or articles of manufacture comprising any of the rAAV particles and/or pharmaceutical compositions of the present disclosure. The kits or articles of manufacture may comprise any of the rAAV particles or rAAV particle compositions of the invention. In some embodiments the kits are used to improve the stability and/or improve the transduction efficiency of rAAV particles; for example, for use in substituting the amino acid residue at position 2 of VP1 and/or VP3 to improve acetylation of rAAV capsid proteins. In some embodiments the kits are used to modulate the stability and/or the transduction efficiency of rAAV particles (e.g., increase stability and/or transduction efficiency or decrease stability and/or transduction efficiency); for example, for use in substituting the amino acid residues that modulate deamidation (e.g., increase deamidation or decrease deamidation).

In some embodiments, the kits or articles of manufacture further include instructions for administration of a composition of rAAV particles. The kits or articles of manufacture described herein may further include other materials desirable from a commercial and user standpoint, including other buffers, diluents, filters, needles, syringes, and package inserts with instructions for performing any methods described herein. Suitable packaging materials may also be included and may be any packaging materials known in the art, including, for example, vials (such as sealed vials), vessels, ampules, bottles, jars, flexible packaging (e.g., sealed Mylar or plastic bags), and the like. These articles of manufacture may further be sterilized and/or sealed.

In some embodiments, the kits or articles of manufacture further contain one or more of the buffers and/or pharmaceutically acceptable excipients described herein (e.g., as described in REMINGTON'S PHARMACEUTICAL SCIENCES (Mack Pub. Co., N.J. 1991). In some embodiments, the kits or articles of manufacture include one or more pharmaceutically acceptable excipients, carriers, solutions, and/or additional ingredients described herein. The kits or articles of manufacture described herein can be packaged in single unit dosages or in multidosage forms. The contents of the kits or articles of manufacture are generally formulated as sterile and can be lyophilized or provided as a substantially isotonic solution.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Direct LC/MS and LC/MS/MS for Complete Characterization of Recombinant AAV Viral Capsid Protein Recombinant adeno-associated viruses (rAAVs) have become popular gene therapy vectors due to their nonpathogenic nature, ability to infect both dividing and non-dividing cells and long term gene expression. Currently, AAV-based gene therapies are used in clinical trials for numerous disease targets, such as muscular dystrophy, hemophilia, Parkinson's disease, Leber's congenital amaurosis and macular degeneration.

AAV is a small and nonenveloped parvovirus with a single stranded DNA genome encapsulated in an icosahedra shell. Each capsid includes sixty copies of three viral capsid proteins VP1 (87 kDa), VP2 (73 kDa) and VP3 (62 kDa) in an approximately 1:1:10 ratio. The three viral capsid proteins are expressed from the same open reading frame by using alternative splicing and an atypical start codon and thus have overlapping sequences. VP1 has ~137 additional N-terminal amino acid residues compared to VP3 while VP2 has ~65 additional N-terminal amino acid residues compared to VP3. At least 13 AAV serotypes and ~150 gene sequences have been isolated from human and non-human primate tissues; AAV serotypes differ in the amino acid sequence of viral capsid proteins and their corresponding cellular receptors and co-receptors for targeting.

The AAV capsid, in addition to protecting the genome inside, plays an important role in mediating receptor binding, escape of virus from endosome, and transport of viral DNA into nucleus in the viral infection cycle, thus directly impacting viral infectivity. It has been shown that the VP1 N-terminus contains a phospholipase PLA2 domain (a.a. 52-97) which is critical in endosomal escaping of virus [1-3]. N-termini of VP1 and VP2 also contain three basic amino acid clusters as nuclear localization signals. These sequences are highly conserved among different AAV serotypes. Mutations of these amino acids have been shown to reduce or abolish infectivity completely [4]. In addition, each AAV serotype has corresponding sequence-specific receptors and co-receptors. For example, heparin sulfate proteoglycan was identified as a major receptor of AAV2 and several other co-receptors, including αVβ5 integrin, fibroblast growth factor receptor 1, and hepatocyte growth receptor have been identified [5-8]. Mutation analysis of AAV2 capsid proteins has identified a group of basic amino acids (Arginine484, 487, 585, and Lysine532) as a heparin-binding motif which contributes to the heparin and HeLa cell binding [9]. NGR domain in AAV2 was identified as an integrin α5β1 binding domain which is essential for viral cell entry [10]. In summary, viral capsid protein sequences are important in cellular targeting and trafficking in the viral infection cycle. Since different production conditions may cause different expression levels of viral capsid proteins, post-translational modifications, and truncations, the viral capsid proteins need to be characterized and monitored to ensure the product consistency in gene therapy development programs.

Traditionally, SDS-PAGE has been used to characterize the AAV viral capsid proteins, providing rough molecular weight information such as 87 kDa, 73 kDa and 62 kDa. No sequence information was obtained from Edman sequencing, possibly due to the blocked N-termini of viral capsid proteins, except VP2. Although X-ray structures of multiple AAVs have been solved, only the VP3 region sequence was observed in the crystal structures. Fifteen N-terminal amino acid residues of VP3 were still missing in the X-ray structure, possibly due to its intrinsic disorder [11-13]. It is possible that the lack of information of VP1 and VP2 N-terminal regions in the atomic structure might be due to low stoichiometry of VP1 and VP2 in the capsid. In addition, N-termini of VP1 and VP2 are buried inside the capsid and are not accessible to antibodies in the native state as reported in the some literature [3, 14, 15]. Conventionally, a Gel-LC/MS method (SDS-PAGE, in-gel tryptic digestion and LC/MS/MS) was used in characterization of VPs [16-18]. However, N-termini of VP1, VP2 and VP3 have not been confirmed using this approach, since this method failed to obtain 100% sequence coverage of VPs due to the limited recovery of peptide from gel.

Direct analysis using MALDI-TOF MS was reported for several virus capsid proteins including tobacco mosaic virus U2 after dissociation with organic acid [19]. Direct peptide mapping after amide hydrogen exchange and mass spectrometry have been used to study the pH-induced structural changes in the capsid of brome mosaic virus (BMV) [20]. Since AAVs are nonenveloped viruses containing only capsid proteins and genome, AAVs capsids could be directly analyzed by RP-LC/MS of proteins and LC/MS/MS of peptide mapping to achieve 100% sequence coverage after capsid dissociation without SDS-PAGE separation. The DNA fragments could elute in the void volume and thus have no interference on protein/peptide detection by LC/MS. In order to investigate these methods, direct LC/MS of different types of AAVs after denaturation was used to monitor the protein sequence and post-translational modifications of AAV capsid proteins. As described herein, N-termini of VP1, VP2 and VP3 of AAVs have been confirmed by mass spectrometry. Acetylations of N-termini of VP1 and VP3 were also identified in the different serotype of AAVs. Direct LC/MS/MS peptide mapping of AAVs has also been developed to provide sequence coverage of VP1, VP2 and VP3 and confirm the N-termini acetylation of VP1 and VP3.

Methods

Materials and Reagents

Dithiothreitol (DTT), 4-vinylpyridine, ultra-pure formic acid, acetic acid, guanidine-HCl, Tris-HCl and Tris base were purchased from Sigma Chemicals (St. Louis, MO). Amicon ultra-4 filters were purchased from Millipore (Billerica, MA). The porcine sequencing grade trypsin was purchased from Promega (Milwaukee, WI). Endoproteinase Lys-C and Asp-N were purchased from Roche (Germany). Slide-A-Lyzer cassettes with 10,000 MWCO were purchased from Pierce (Rockford, IL).

Vector Production and Purification

AAV vectors were produced using the transient triple transfection method as previously described (Xiao, 1998 #123). Briefly, HEK293 cells were transfected using polyethyleneimine, PEI, and a 1:1:1 ratio of three plasmids (ITR vector, AAV rep/cap and Ad helper plasmid). The vector plasmid contains the vector genome CBA-EGFP and ITR sequences from AAV2. EGFP expression is driven by the CMV enhancer chicken beta actin hybrid promoter (CBA) as described (Miyazaki, 1989 #124) (Niwa, 1991 #125). The AAV rep/cap helpers contained rep sequences from AAV2 and serotype specific capsid sequences with the nomenclature, rep2/cap2, rep2/cap5, rep2/cap7 etc. The pAd helper used was pHelper (Stratagene/Agilent Technologies, Santa Clara, CA). Purification of AAV was performed as described by Qu et al. (2007, *J. Virol. Methods* 140:183-192).

LC/MS Intact Protein Analysis

The AAV virions were concentrated with an Amicon ultra-4 filter (10 kDa MWCO) and denatured with 10% acetic acid followed by direct analysis in an Acquity UPLC-Xevo® QTOF MS instrument (Waters, Milford, MA). The separations were performed with a UPLC BEH C4 or C8 column (1.7 μm, 2.1 mm i.d.) at a 0.25 ml/min flow rate. Mobile phase A was 0.1% formic acid in water while mobile phase B was 0.1% formic acid in acetonitrile. The final gradient was as follows: from 10% B to 20% B for 6 minutes, from 20% B to 30% B in 10 min, then from 30% to 38% B for 40 minutes. For MS the capillary voltage and sampling cone voltage were set at 3.5 kV and 45 V respectively. The mass spectra were acquired in the sensitivity mode with m/z range of 500-4000. Assisted calibration with sodium iodide as calibrant was performed for mass calibration. MaxEnt1 in Masslynx software was used for protein deconvolution.

Enzymatic Digestions of AAV2 VPs

The concentrated AAV2 virions were denatured with 6 M Guanidine-HCl, 0.1 M Tris at pH 8.5. The proteins were reduced with 30 mM DTT at 55° C. for 1 hour in darkness and alkylated with 0.07% 4-vinylpyridine at room temperature for 2 hours. The reactions were quenched by the addition of 1M DTT. The samples were dialyzed with Slide-A-Lyzer cassettes (10,000 MWCO) against 25 mM Tris buffer at pH 8.5 for ~18 hours. After dialysis, the samples were split into three aliquots. Each aliquot was digested with trypsin at 1:25 or Lys-C at 1:50 or Asp-N at 1:100 enzyme:protein ratio (wt/wt) for 18 hours at 37° C., respectively.

LC/MS/MS Peptide Mapping

Nano LC/MS/MS was performed in using a NanoAcquity HPLC system (Waters, Milford, MA) in conjunction with an Orbitrap Velos mass spectrometer (Thermo-Fisher Scientific, Waltham, MA) using home packed nanoLC column (75 μm×10 mm) with Magic C18 with packing material (5 μm, Bruker, Billerica, MA) at a 300 nl/min flow rate. The mobile phases A and B were 0.1% formic acid in water and acetonitrile, respectively. The gradient was from 2% B to 60% B in 121 min.

The source parameters for velos were as follows: source voltage: 2.5 kv, capillary temperature 275° C.; S-lens RF level: 55%. Data were acquired using the top-ten data dependent method with accurate ms at 60,000 resolution and 10 MS/MS in ion trap. Mascot was used for database searching against AAV2 viral capsid protein sequences. MS tolerance of 10 ppm and ms/ms tolerance of 0.8 Da were used for the database search.

UPLC/MS/MS Peptide Mapping

The protein digests were also analyzed by UPLC/MS/MS in Acquity UPLC-Xevo qTOF MS. A BEH300 C18 column (2.1×150 mm) was used for separation in the mobile phases with 0.1% formic acid in water/acetontitrile gradient at a flow rate 0.25 ml/min. The mass spectra were acquired in the positive MSe mode in the mass range of 200-2000.

Results

AAV Denaturation Method

AAVs can be denatured through a number of methods using detergent, heat, high salt, or buffer with low or high pHs. Heat denaturation can lead to protein precipitation and as a result reverse phase columns are easily clogged and over pressurized. Denaturation with high salt requires an additional desalting step before LC/MS analysis. Denaturing with 10% acetic acid was used for the LC/MS intact protein analysis, as it allowed for clean mass spectrum. For peptide mapping, either 0.1% RapiGest or 6 M Guanidine HCl can be used as a denaturing reagent.

Intact Protein Analysis Method Development

Figure 1B:
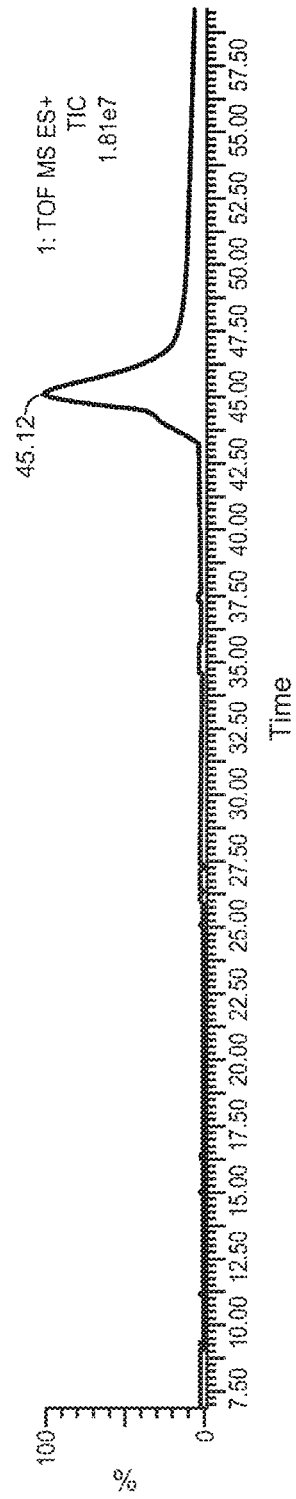
Figure 1C:
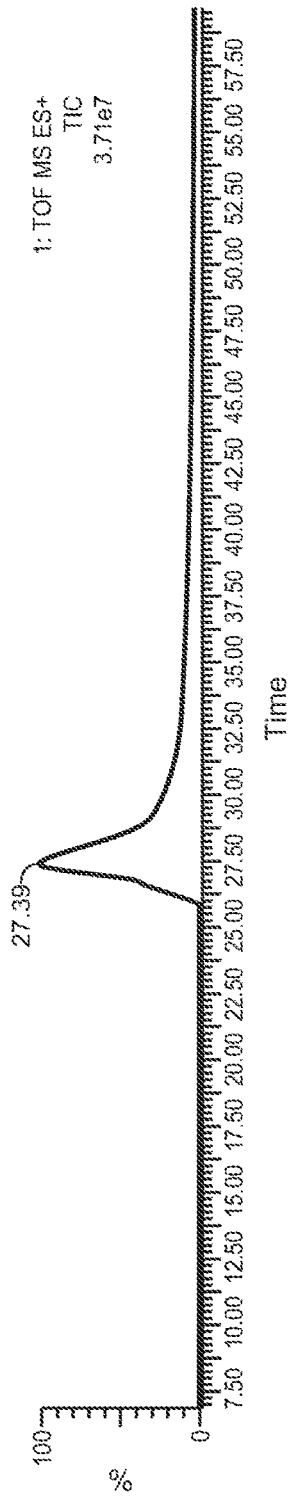
Figure 1D:
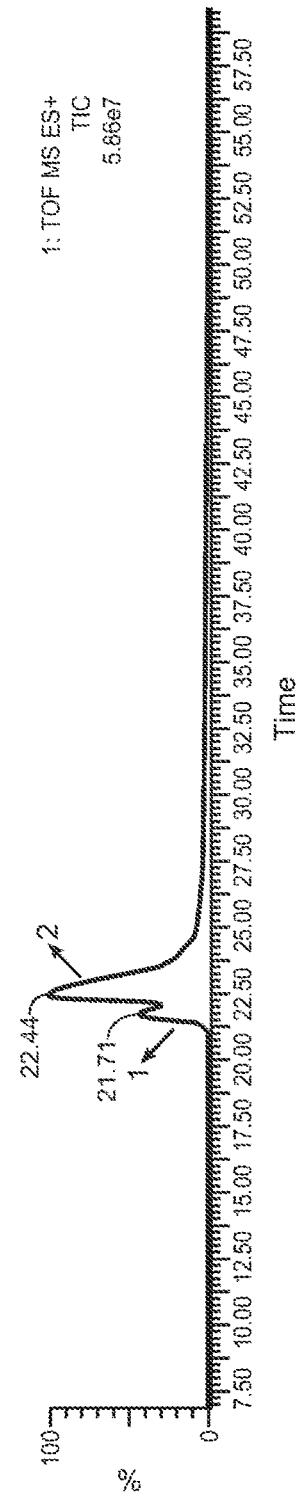

Initial intact protein analysis of AAV2 was performed using an UPLC BEH C4 column at fast gradient. Under this condition, only one single peak in the total ion chromatogram was observed, with a mass corresponding to VP3 (FIG. 1A). Without wishing to be bound by theory, it is thought that the absence of VP1 and VP2 is possibly due to low stoichiometry of VP1 and VP2 or suppression of VP1 and VP2 signals by VP3 if all VPs co-elute. Increasing injection or column length, using a shallower gradient, and using alternative columns have been attempted in order to detect VP1 and VP2. Higher loading (1.7 μg) with a shallower gradient at 0.5% B/min resulted in a shoulder peak on the left (FIG. 1B). The increase in column length from 10 cm to 15 cm did not enhance the separation of the shoulder peak (FIG. 1C). However, the shoulder peak was further separated from the main peak using a BEH C8 column, with improved signal intensities observed (FIG. 1D).

Figure 2A:
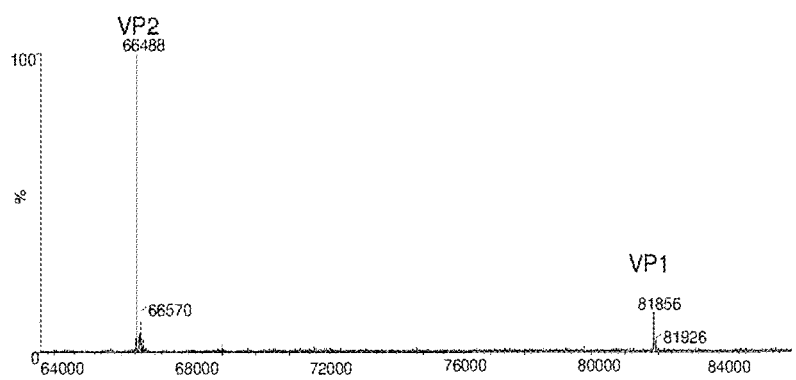
FIGS. 2A&B provide deconvoluted mass spectra from FIG. 1D peak 1 (FIG. 2A) and FIG. 1D peak 2 (FIG. 2B).
Figure 2B:
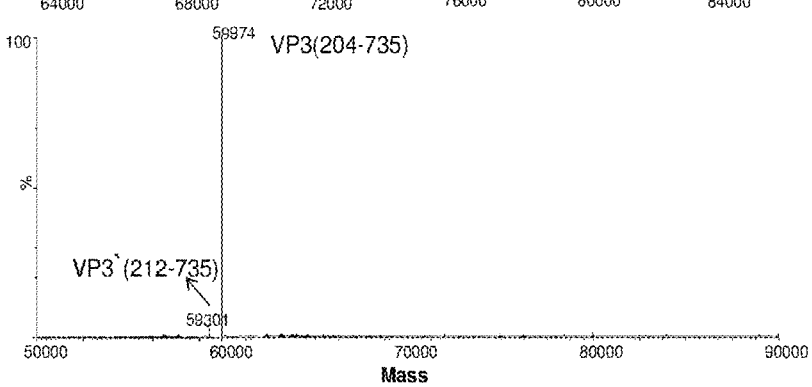

As a result, the VP1 and VP2 masses were obtained in this shoulder peak at the signal intensities shown in FIG. 2A. The masses of VP1 and VP3 correspond to a.a. 2-735(acetylation) and a.a. 204-735(acetylation), respectively (FIGS. 2A&2B). No acetylation was observed in VP2 (a.a.139-735). In addition, a minor peak with a smaller mass than VP3 was observed, with a mass corresponding to amino acid sequence 212-735 with one acetylation (FIG. 2B). These data are consistent with DNA sequences since VP3 contains two ATG initiation codons in AAV2: <u>ATG</u>GCTACAGG CAGTGGCGCA CC<u>AATG</u>GCAGAC (SEQ ID NO:1), resulting in two possible N termini (underlined): <u>M</u>ATGSGAP<u>M</u>AD (SEQ ID NO:2). The N-terminal methionine residues were not present in both VP1 and VP3 as measured by intact protein analysis. The acetylation of VP1 and VP3 is not a method-induced artifact (denaturation of AAV by 10% acetic acid) since acetylation of VP1 and VP3 is also observed in an AAV preparation using an alternative denature method without acetic acid. The intact protein data also confirmed that no glycosylation was present in the viral capsid proteins, even though several N-linked consensus sequences are present [16].

LC/MS/MS Peptide Mapping

To further confirm the N-termini and acetylation observed in the intact protein analysis, peptide mapping was performed using multiple enzymes and analyzed using multiple instruments. Various sample preparation methods, including denaturation methods and desalting steps, have been evaluated. The final digestion method, including denaturation with 6M guanidine HCl, reduction and alkylation with 4-vinylpyridine, and dialysis using slide-A-lyzer followed by enzymatic digestion, created clean peptide mapping with low artificial modifications during the digestion process. As low as 5 μg starting material was tested, yielding complete sequence coverage using nano LC/MS/MS and UPLC/MS/MS.

Mascot search of tryptic digests from nano LC/MS/MS alone yielded 78% sequence coverage with an ion score 13 cut off as shown in FIG. 3. The two large missing tryptic peptides, T27 and T38 (boxed) from nano LC/MS/MS were found in the LC/MS in Xevo TOF MS with BEH C18 column (FIG. 3). In addition, most of the T27 and T38 peptide sequences were further confirmed by nano LC/MS/MS of Asp-N digests as shown in Italics in FIG. 3. The complete N-terminal and C-terminal peptides were covered by Lys-C digests as underlined in FIG. 3. Therefore, 100% sequence coverage of VP1 was achieved through multiple enzyme digestions and two LC/MS/MS methods.

Figure 4A:
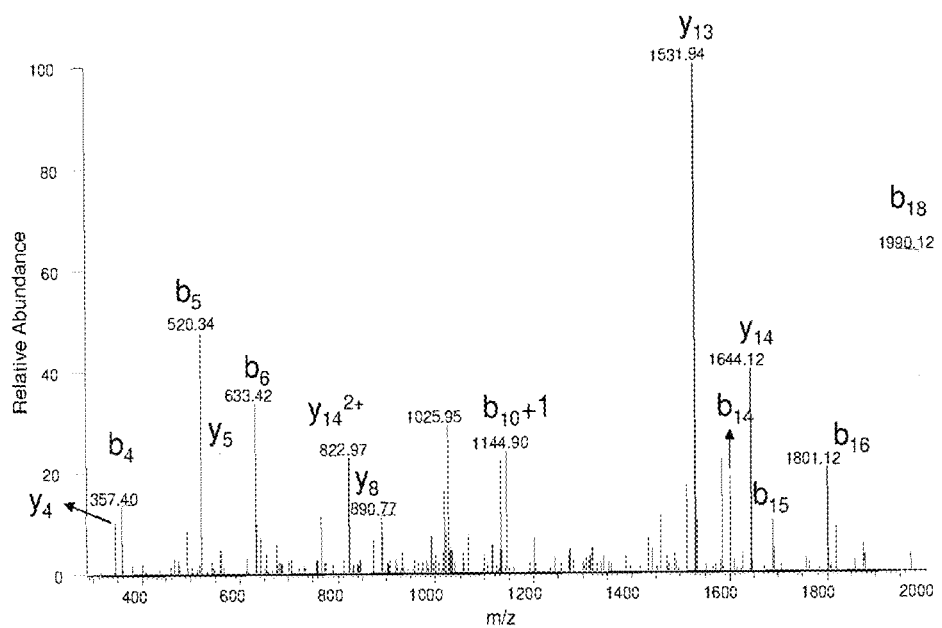
FIGS. 4A-4C provide MS/MS spectra of AAV2 VP N-terminal peptides.
Figure 4B:
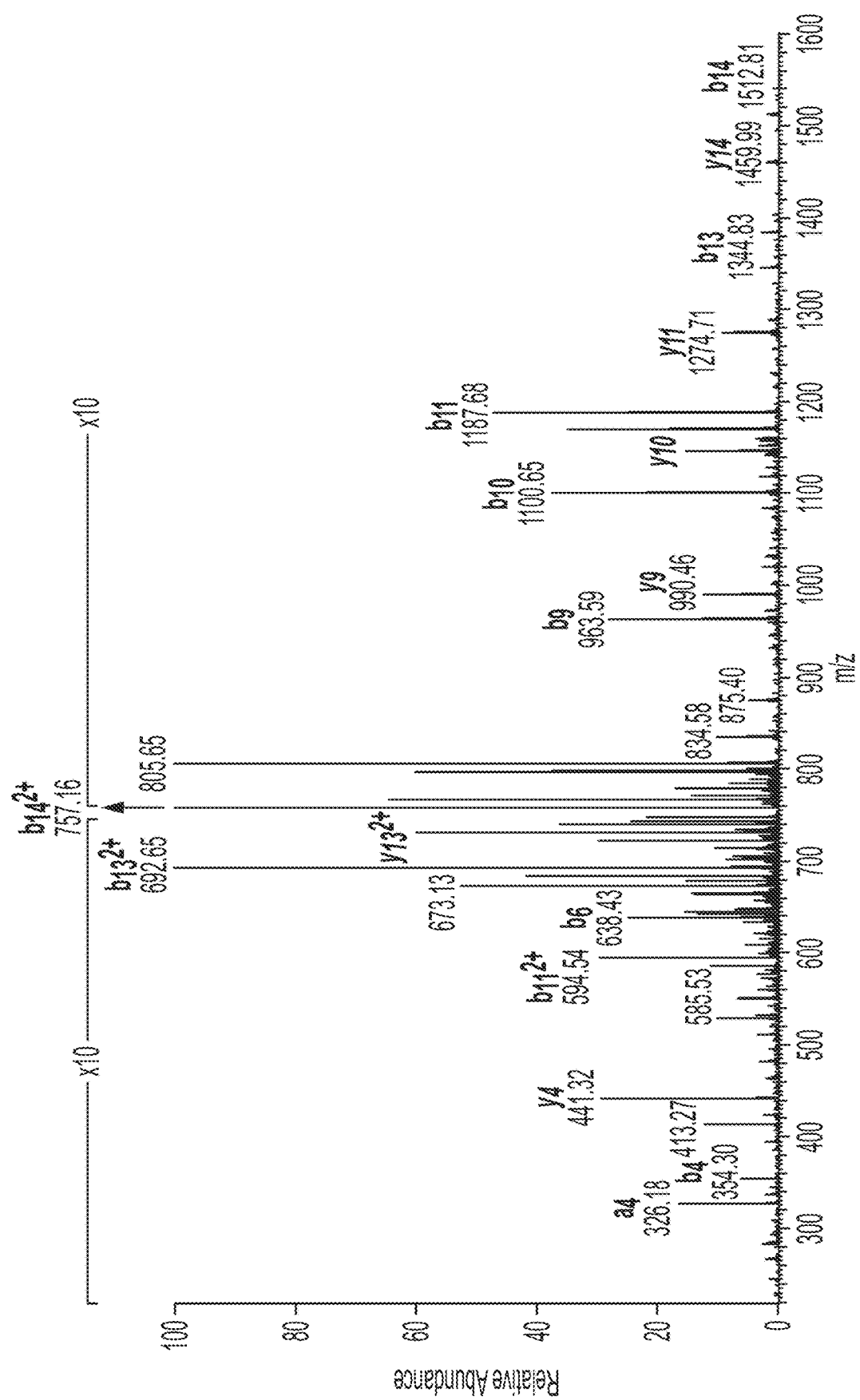
Figure 4C:
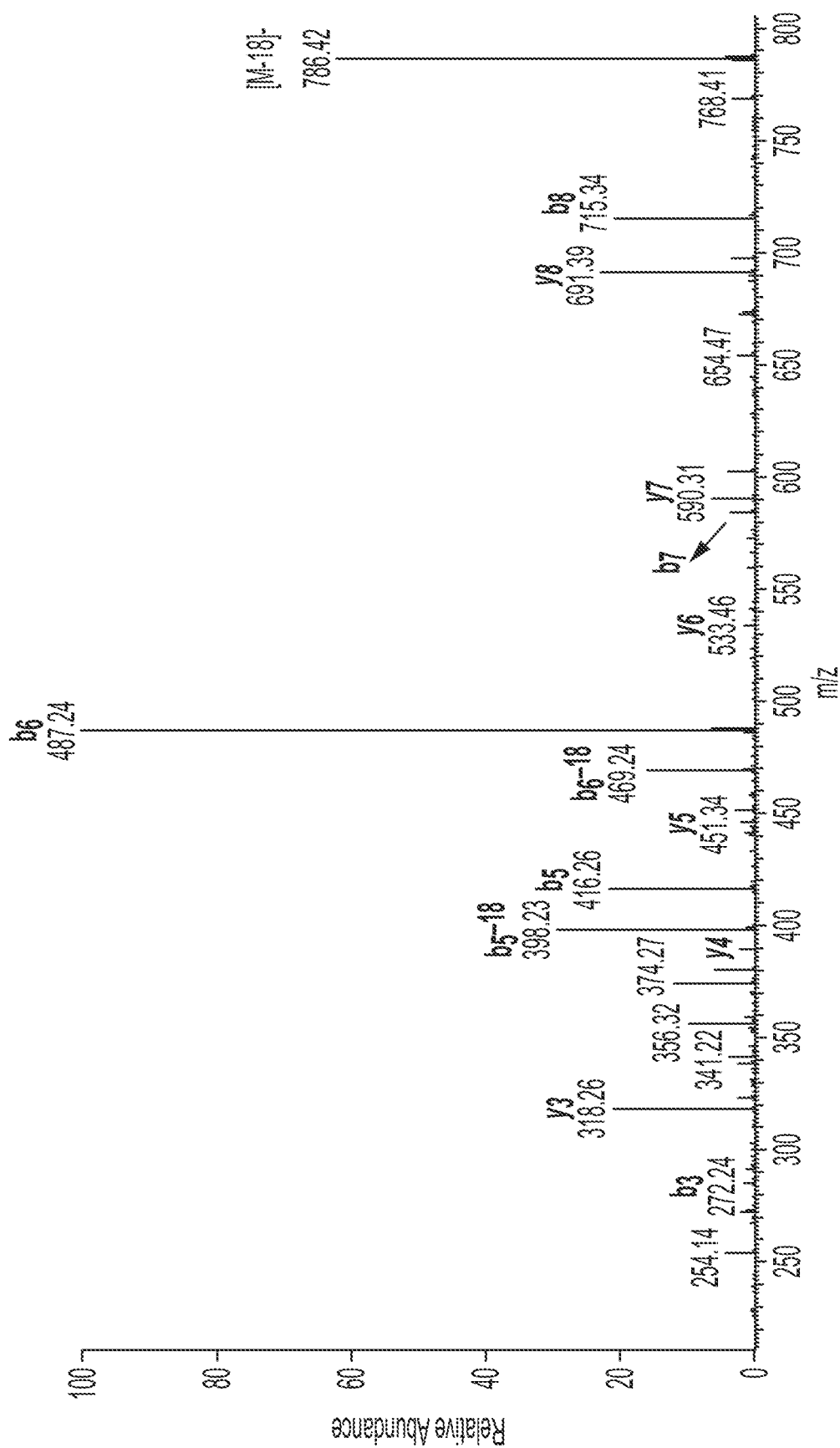

LC/MS/MS confirmed the N- and C-termini of VP1, VP2 and VP3 and N-terminal acetylation of VP1 and VP3 observed in the intact protein analysis. FIGS. 4A-4C show the MS/MS spectra of the VP1 N-terminal tryptic peptide A(Ac)ADGYLPDWLEDTLSEGIR (SEQ ID NO:4) (FIG. 4A), VP2 N-terminal Asp-N derived peptide (APGKKRPVEHSPVEP) (SEQ ID NO:15) (FIG. 4B), and VP3 N-terminal Asp-N peptide A(Ac)TGSGAPM (SEQ ID NO:5) (FIG. 4C). MS/MS has confirmed the location of acetylation at the N-terminal alanine residues in both VP1 and VP3 peptides. The presence of unmodified y18 and y17 ions, and all detected b ions with 42 Da mass shift in FIG. 4A indicates the 42 da-modification is located in N-terminal of VP1. Similarly, the presence of unmodified y3 to y8 ions in FIG. 4C confirmed the location of acetylation at the N-terminal alanine residue.

Comparison of AAV VP N-Termini

In addition to AAV2, AAV1, AAV5, AAV7, AAV9 and AAV Rh10 have also been analyzed by intact protein analysis. The theoretical and predicted masses of VPs in AAVs are shown in Table 2.

TABLE 2

Theoretical Mass vs Experimental Mass for AAV VPs

| Serotype | Isoform | Predicted amino acid sequence | Actual amino acid sequence | Theoretical Ms.(Da) | Experimental Ms.(Da) |
|---|---|---|---|---|---|
| AAV1 | VP1 | 1-736 | 2(ac)-736 | 81286 | 81291 |
|  | VP2 | 138-736 | 139-736 | 66093 | 66098 |
|  | VP3 | 203-736 | 204(ac)-736 | 59517 | 59520 |
| AAV2 | VP1 | 1-735 | 2(ac)-735 | 81856 | 81856 |
|  | VP2 | 138-735 | 139-735 | 66488 | 66488 |
|  | VP3 | 203-735 | 204(ac)-735 | 59974 | 59974 |
| AAV5 | VP1 | 1-724 | 2(ac)-724 | 80336 | 80336 |
|  | VP2 | 137-724 | 138-724 | 65283 | 65284 |
|  | VP3 | 193-724 | 194(ac)-724 | 59463 | 59463 |
| AAV7 | VP1 | 1-737 | 2(ac)-737 | 81564 | 81567 |
|  | VP2 | 138-737 | 139-737 | 66372 | 66374 |
|  | VP3 | 204-737 | 213(ac)-737 | 59101 | 59103 |
| AAV9 | VP1 | 1-736 | 2(ac)-736 | 81291 | 81288 |
|  | VP2 | 138-736 | 139-736 | 66210 | 66209 |
|  | VP3 | 203-736 | 204(ac)-736 | 59733 | 59733 |
| AAVRh10 | VP1 | 1-738 | 2(ac)-738 | 81455 | 81455 |
|  | VP2 | 138-738 | 139-738 | 66253 | 66252 |
|  | VP3 | 204-738 | 205(ac)-738 | 59634 | 59634 |

Figure 5A:
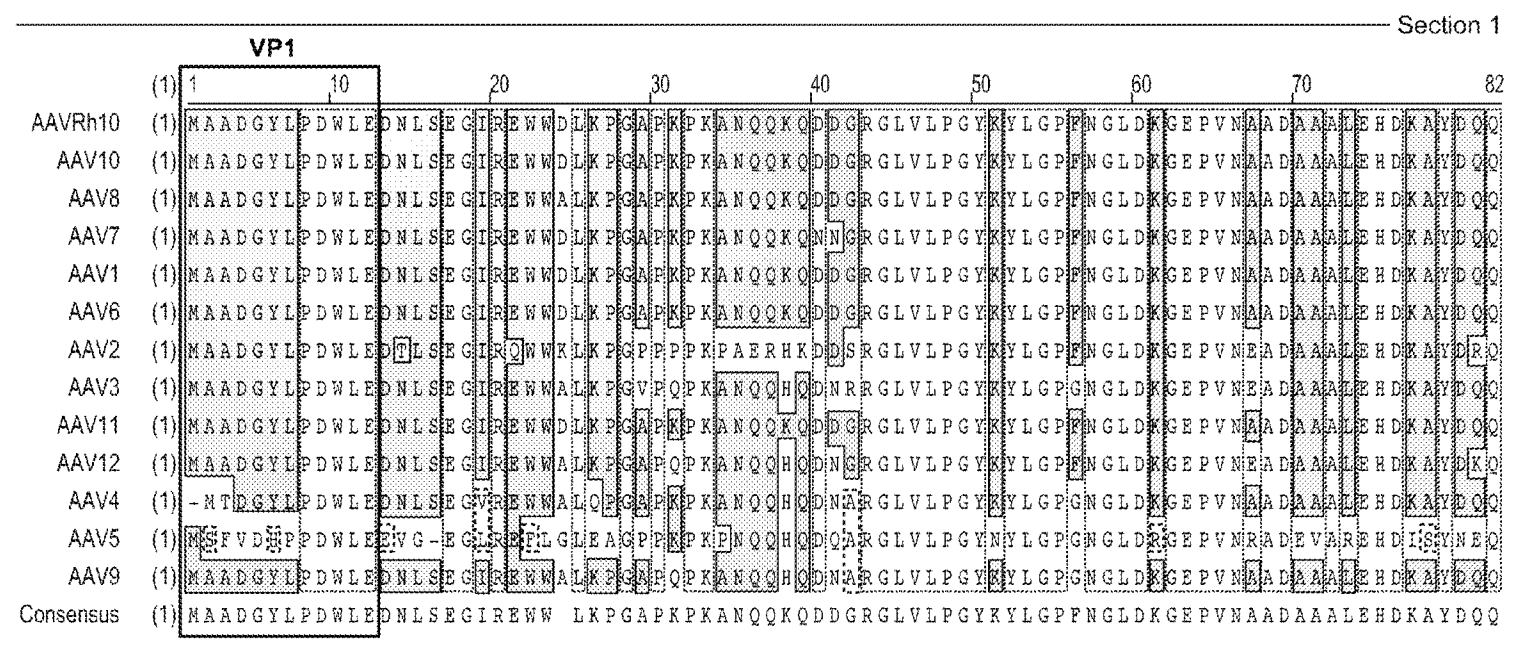
Figure 5B:
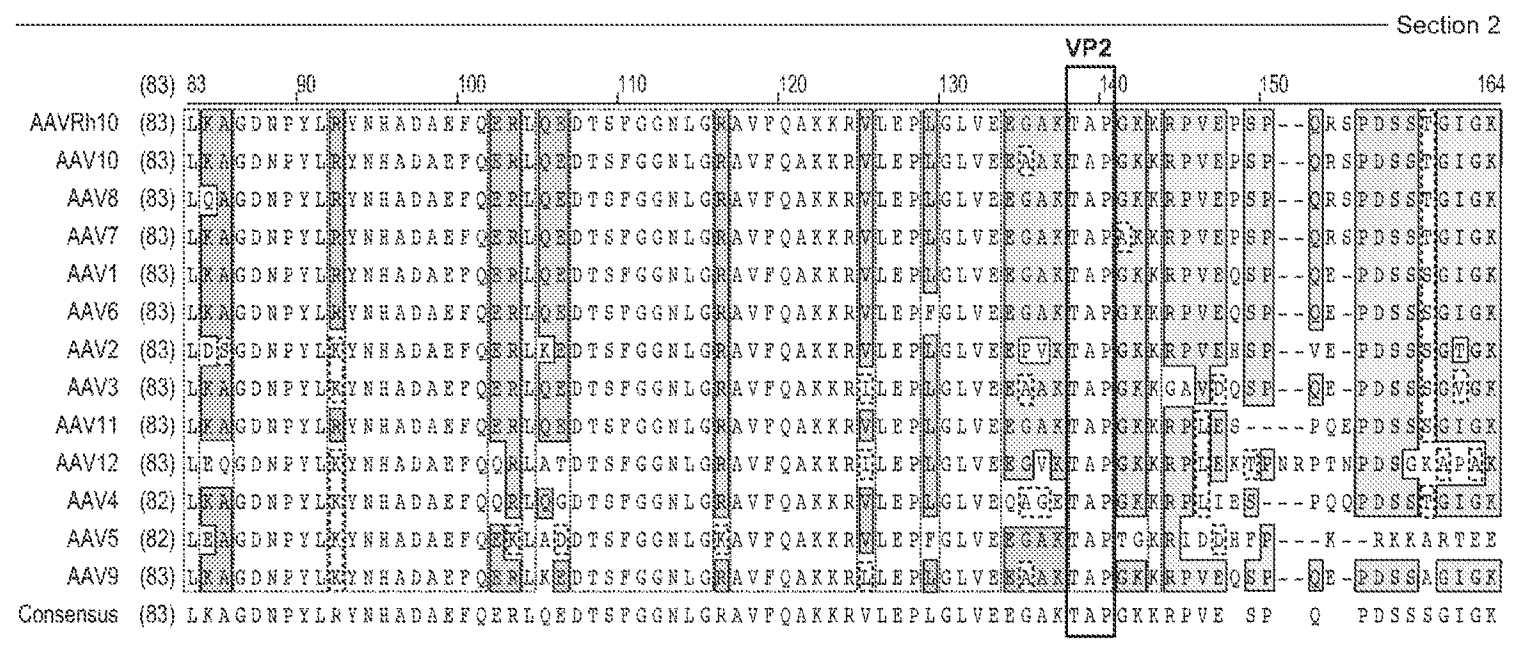
Figure 5C:
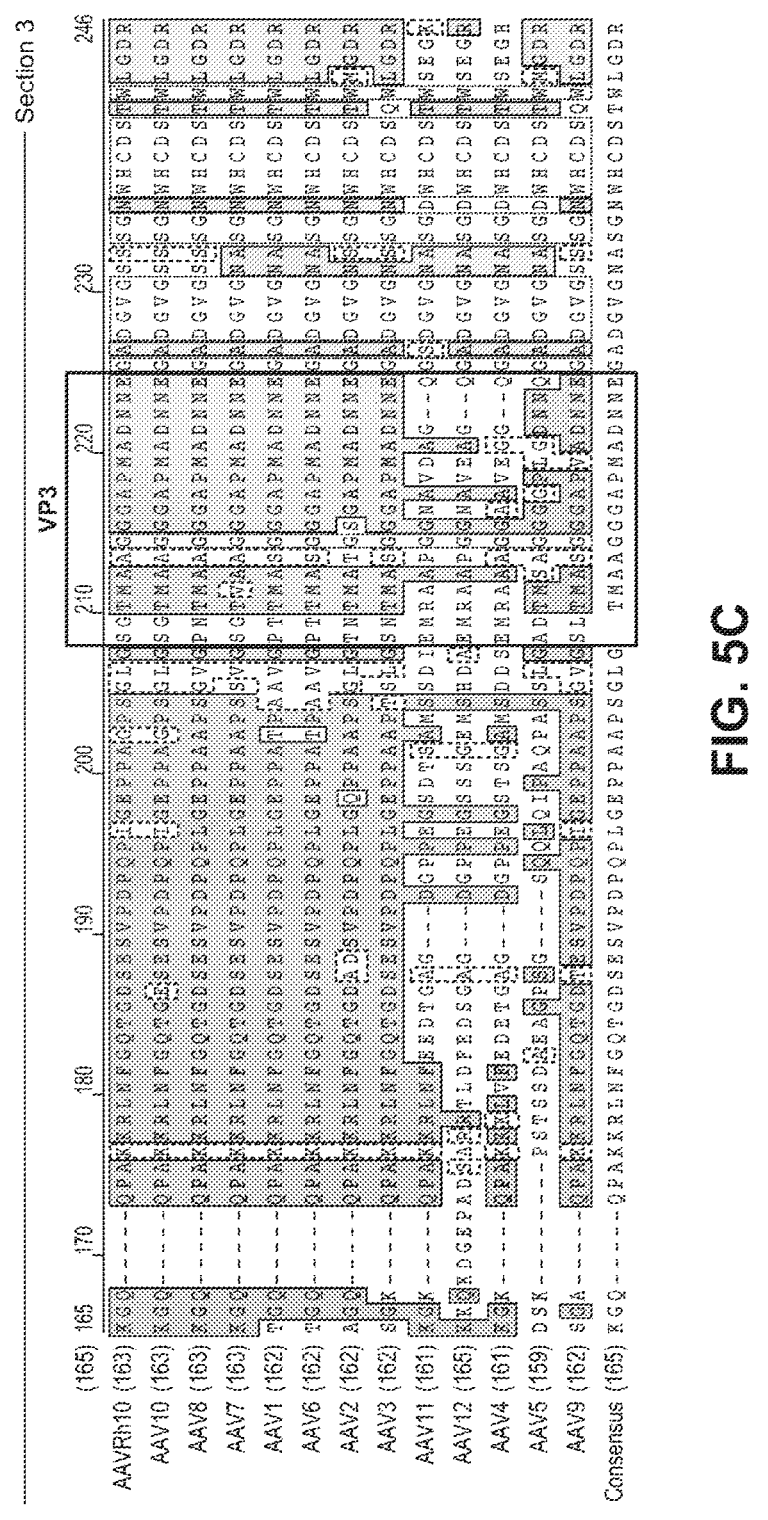

N-termini, as well as their posttranslational modifications, are highly conserved among the AAV serotypes analyzed, even though AAV5 is reported as the most diverse AAV serotype sequence, as shown in the sequence alignments in FIG. 5. In 11 out of 13 AAV serotypes, the N-termini of VP1 share an identical 13 amino acid residue sequence (MAADGYLPDWLED) (SEQ ID NO:6) while all 13 AAV serotypes have identical TAP . . . N-terminal sequences in VP2 (FIG. 5). LC/MS of AAV2 indicated that T is missing in VP2 at protein level. The N-termini of VP3 are the most diverse among the three viral capsid proteins, with 8 out of 13 AAV serotypes sharing a MA . . . N-terminal sequence. Similar to AAV2, AAV1 and AAV Rh10 also have two ATG initiation codons with the first one as predominant N-terminal based on LC/MS intact protein analysis. Interestingly, though AAV7 has two potential initiation codons (GTG G CTGCAGGCGGTGGCGCACCAATG GCAGACAAT AAC . . . ) (SEQ ID NO:7), the second initiation codon (ATG) was favorable based on the intact protein analysis: the VP3' with 213(ac)-737 was a predominant peak while VP3 with 203(ac)-737 was a minor peak.

Conclusions

Applications of LC/MS Intact Protein Analysis and LC/MS/MS Peptide Mapping of AAV VPs in Gene Therapy Research and Development These results demonstrate that direct LC/MS of different types of AAVs after denaturation was proved to be a simple and effective way to monitor the protein sequence and post-translational modifications with accurate mass measurement in the intact protein level. N-termini of VP1, VP2 and VP3 of AAVs were confirmed by mass spectrometry. Acetylations of N-termini of VP1 and VP3 were also identified in different serotypes of AAVs. Direct LC/MS/MS peptide mapping of AAVs was developed, provided 100% sequence coverage of VP1, VP2 and VP3, and confirmed the N-termini acetylation of VPs. The theoretical masses of predicted sequences of 13 AAV serotypes based on sequence alignment and intact protein analysis of several AAV serotypes are shown in Table 3.

TABLE 3

| | Predicted VP1 sequence | Mass(Da) | Predicted VP2 sequence | Mass(Da) | Predicted VP3 sequence | Mass(Da) |
|---|---|---|---|---|---|---|
| AAV1 | 2(ac)-736 | 81286 | 139-736 | 66093 | 204(ac)-736 | 59517 |
| AAV2 | 2(ac)-735 | 81856 | 139-735 | 66488 | 204(ac)-735 | 59974 |
| AAV3 | 2(ac)-736 | 81571 | 139-736 | 66319 | 204(ac)-736 | 59849 |
| AAV4 | 2(ac)-734 | 80550 | 138-734 | 65626 | 198(ac)-734 | 59529 |
| AAV5 | 2(ac)-724 | 80336 | 138-724 | 65283 | 194(ac)-724 | 59463 |
| AAV6 | 2(ac)-736 | 81322 | 139-736 | 66096 | 204(ac)-736 | 59519 |
| AAV7 | 2(ac)-737 | 81564 | 139-737 | 66372 | 213(ac)-737 | 59101 |
| AAV8 | 2(ac)-738 | 81667 | 139-738 | 66519 | 205(ac)-738 | 59805 |
| AAV9 | 2(ac)-736 | 81291 | 139-736 | 66210 | 204(ac)-736 | 59733 |
| AAV10 | 2(ac)-738 | 81477 | 139-738 | 66271 | 205(ac)-738 | 59638 |
| AAV11 | 2(ac)-733 | 80987 | 139-733 | 65794 | 198(ac)-733 | 59696 |
| AAV12 | 2(ac)-742 | 82106 | 139-742 | 66905 | 207(ac)-742 | 59846 |
| AAVRh10 | 2(ac)-738 | 81455 | 139-738 | 66253 | 205(ac)-738 | 59634 |

The accurate masses of VP1, VP2 and VP3 of each serotype are unique and therefore intact protein analysis can be used as an identity test to differentiate AAV capsid serotypes. Tables 4-6 show the mass differences of VPs among 13 common AAV serotypes. Shown in regular font are delta masses larger than 10, with delta masses less than 10 bolded.

TABLE 4

Mass Differences of VP1 Among 13 AAV Isotypes

| | AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|---|
| AAV2 | 570 | | | | | | | | | | | |
| AAV3 | 285 | 285 | | | | | | | | | | |
| AAV4 | 736 | 1306 | 1021 | | | | | | | | | |
| AAV5 | 950 | 1520 | 1235 | 215 | | | | | | | | |
| AAV6 | 36 | 534 | 249 | 772 | 987 | | | | | | | |
| AAV7 | 277 | 292 | 8 | 1013 | 1228 | 241 | | | | | | |
| AAV8 | 381 | 189 | 96 | 1117 | 1332 | 345 | 104 | | | | | |
| AAV9 | 5 | 585 | 280 | 741 | 955 | 31 | 272 | 376 | | | | |
| AAV10 | 191 | 379 | 94 | 927 | 1142 | 155 | 86 | 190 | 186 | | | |
| AAV11 | 299 | 869 | 584 | 436 | 651 | 335 | 577 | 681 | 304 | 490 | | |
| AAV12 | 820 | 250 | 535 | 1555 | 1770 | 784 | 542 | 439 | 815 | 629 | 1119 | |
| AAVRh10 | 169 | 401 | 116 | 905 | 1119 | 133 | 109 | 212 | 164 | 22 | 468 | 651 |

TABLE 5

Mass Differences of VP2 among 13 AAV Isotypes

| | AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|---|
| AAV2 | 395 | | | | | | | | | | | |
| AAV3 | 226 | 169 | | | | | | | | | | |
| AAV4 | 467 | 862 | 693 | | | | | | | | | |
| AAV5 | 810 | 1205 | 1036 | 343 | | | | | | | | |
| AAV6 | 2 | 392 | 224 | 470 | 812 | | | | | | | |
| AAV7 | 278 | 116 | 52 | 746 | 1088 | 276 | | | | | | |
| AAV8 | 425 | 31 | 199 | 893 | 1235 | 423 | 147 | | | | | |
| AAV9 | 117 | 278 | 109 | 584 | 927 | 115 | 161 | 308 | | | | |
| AAV10 | 177 | 217 | 49 | 645 | 987 | 175 | 101 | 248 | 60 | | | |
| AAV11 | 299 | 694 | 525 | 168 | 511 | 301 | 578 | 725 | 416 | 476 | | |
| AAV12 | 812 | 417 | 586 | 1279 | 1622 | 810 | 533 | 386 | 695 | 635 | 1111 | |
| AAVRh10 | 160 | 235 | 66 | 627 | 970 | 157 | 119 | 266 | 43 | 18 | 459 | 652 |

TABLE 6

Mass Differences of VP3 among 13 AAV Isotypes

|  | AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|---|
| AAV2 | 457 | | | | | | | | | | | |
| AAV3 | 332 | 125 | | | | | | | | | | |
| AAV4 | 12 | 445 | 320 | | | | | | | | | |
| AAV5 | 54 | 511 | 386 | 66 | | | | | | | | |
| AAV6 | 2 | 455 | 330 | 10 | 56 | | | | | | | |
| AAV7 | 416 | 673 | 748 | 428 | 362 | 418 | | | | | | |
| AAV8 | 288 | 169 | 44 | 276 | 342 | 286 | 704 | | | | | |
| AAV9 | 216 | 241 | 116 | 204 | 270 | 214 | 632 | 72 | | | | |
| AAV10 | 121 | 336 | 211 | 109 | 175 | 119 | 537 | 167 | 95 | | | |
| AAV11 | 179 | 278 | 153 | 167 | 233 | 177 | 595 | 109 | 37 | 58 | | |
| AAV12 | 329 | 128 | 3 | 317 | 383 | 327 | 745 | 41 | 113 | 208 | 150 | |
| AAVRh10 | 117 | 340 | 215 | 105 | 171 | 115 | 533 | 171 | 99 | 4 | 62 | 212 |

No masses within 10 Da of all three VPs between two isotypes are observed. Even though both VP2 and VP3 have only a 2 Da difference between AAV1 and AAV6, the mass difference of VP1 between AAV1 and AAV6 is 36, significant enough to be distinguished by an accurate mass measurement. Therefore, intact protein measurement of VP1, VP2 and VP3 is highly specific as an identity test.

These results demonstrate that intact protein analysis and LC/MS/MS can be used to profile VPs to monitor VP expressions, posttranslational modifications, and truncations and to ensure product consistency during VLP production. These two analyses can also be used to confirm site-direct mutagenesis or structural characterization for capsid protein engineering applications.

Example 2: The Role of N Terminal Acetylation of AAV Capsid Proteins

Chemical modifications of cellular proteins are a common means of controlling their functions (Arnesen, T. (2006) *Virology* 353(2): 283-293). N-terminal acetylation (Nt-acetylation), which involves the transfer of an acetyl group from acetyl coenzyme A to the α-amino group of the first amino acid residue of a protein (Brown, J. L. and Roberts, W. K. (1976) *J Biol Chem* 251: 1009-1014; Arnesen, T. et al. (2009) *Proc Natl Acad Sci USA* 106: 8157-8162), is among the most abundant of protein modifications. Unlike most other protein modifications, Nt-acetylation is irreversible; it occurs mainly during the synthesis of the protein, catalyzed by N-terminal acetyltransferases (NATs) associated with ribosomes (Gautschi, M. et al. (2003) *Mol Cell Biol* 23: 7403-7414; Pestana, A. and Pitot, H. C. (1975) *Biochemistry* 14: 1404-1412; Polevoda, B. et al. (2003) *J Biol Chem* 278: 30686-97). There are several distinct NATs in eukaryotes—NatA-NatF—each composed of one or more subunits and each acetylating a specific subgroup of N-termini depending on the amino acid sequence of the first few amino acids (Jornvall, H. (1975) *J Theor Biol* 55: 1-12; Persson, B. et al. (1985) *Eur J Biochem* 152: 523-527).

Experimental data indicate that proteins with acetylated N-termini are more stable in vivo than non-acetylated proteins; i.e., Nt-acetylation protects proteins from degradation (Hershko, A. et al. (1984) *Proc Natl Acad Sci USA* 81: 7021-7025). One explanation for this might be the discovery in 2004 that another N-terminal modification, ubiquitination, which involves direct attachment of the small protein ubiquitin to the N-terminal amino acid residue, promotes the subsequent degradation of the protein (Ben Saadon, R. et al. (2004) *J Biol Chem* 279: 41414-41421). Conversely, the Nt-acetylation signals can also be part of a quality control mechanism to degrade unfolded or misfolded proteins and to regulate in vivo protein stoichiometries (Hwang, C. S. et al. (2010) *Science* 327: 973-977).

A systematic analysis of the predicted N-terminal processing of cytosolic proteins, versus those destined to be sorted to the secretory pathway, revealed that the cytosolic proteins were profoundly biased in favor of processing, but there is an equal and opposite bias against such modification for secretory proteins (Forte, G. M. A. et al. (2011) *PLoS Biology*, 4 May 2011 Volume 9). Mutations in secretory signal sequences that lead to their acetylation result in mis-sorting to the cytosol in a manner that is dependent upon the N-terminal processing machinery. Hence N-terminal acetylation represents an early determining step in the cellular sorting of nascent polypeptides that represent an extra layer of stringency in order to ensure that proteins destined to remain in the cytosol actually reside in the cytosol. The eukaryotic cell comprises several distinct compartments, called organelles, required to perform specific functions. The proteins in these compartments are synthesized in the cytoplasm and so require complex sorting mechanisms to ensure their delivery to the appropriate organelle. Proteins are modified by acetylation of their amino terminus at a very early stage in their synthesis. There is a profound difference between the likelihood of such a modification on cytoplasmic proteins and on those destined for one of the major organelles, the endoplasmic reticulum (ER): whereas cytoplasmic proteins are typically acetylated, those bound for the ER are largely unmodified. Moreover, when specific ER proteins are engineered to induce their acetylation their targeting to the ER was inhibited (Forte, G. M. A. et al. (2011) *PLoS Biology*, 4 May 2011 Volume 9).

The contractile proteins actin and tropomyosin have been shown to require NatB-mediated Nt-acetylation for proper function, specifically involving actin-tropomyosin binding and actomyosin regulation (Coulton, A. T. et al. (2010) *J Cell Sci* 123: 3235-3243; Polevoda, B. et al. (2003) *J Biol Chem* 278: 30686-97). Thus Nt acetylation of AAV capsid proteins may have importance in the transduction potential of rAAV vectors. If AAV vectors fail to gain entry into the nucleus, they consequently fail to transduce cells. The role of actin filaments and FKBP52 (FK506-binding protein p52) in the translocation of AAV capsids from the endosome (o the nucleus is well defined (Zhao, W. et al. (2006) *Virology* 353(2): 283-293). Importantly, Nt-acetylation is essential for the functioning of actin filaments by modulating protein-protein interactions (Coulton, A. T. et al. (2010) *J Cell Sci* 123: 3235-3243; Polevoda, B. et al. (2003) *J Biol Chem* 278: 30686-97).

Though N-terminal acetylation of proteins is a widely known phenomenon, the biological significance of Nt-acetylation on AAV capsid proteins is not well understood. The predicted N-termini of VP1 and VP3 based on DNA sequencing are both methionine followed by alanine. It has been reported that removal of N-terminal methionine by Met-aminopeptidases frequently leads to Nt-acetylation of the resulting N-terminal alanine, valine, serine, threonine, and cysteine residues and that the acetylation of the N-terminus acts as a potential degradation signal [21]. Ubiquitination of viral capsid proteins was suggested as a potential signal for processing of the capsid at the time of virion disassembly [22]. The link between N-acetylation of VP1 and VP3 and viral capsid degradation and uncoating before the nuclear entry is further investigated.

To understand the functional implications of N-terminal acetylation with regard to AAV capsid proteins, site-directed mutagenesis of VP3 N-terminal initiation codons is used to generate AAV mutants.

Methods

AAV capsid proteins are generated with differing amino acids at the $2^{nd}$ position to the initiating methionine (iMet X) to determine if Nt-acetylation is inhibited or reduced, and the functional consequences are then measured. The ability of the capsid proteins to be trafficked intra-cellularly and/or to acquire post translational modifications such as glycosylation is assessed, and whether this ability affects the infectivity of the assembled AAV particle is subsequently determined. In addition, the impact of acetylation on ubiquitination/degradation and targeting to the lysosome, ER, Golgi, or inner nuclear membrane is determined.

For example, to assay trafficking or targeting, AAV particles with capsid proteins having a mutated $2^{nd}$ position (e.g., iMet X) are fluorescently labeled and used to infect cells (e.g., HeLa cells). These AAV particles are assayed for one or more of: time of viral particle uptake, colocalization of AAV particles with specific compartmental markers (e.g., Golgi, ER, or lysosomal proteins or other markers), nuclear accumulation (e.g., as assayed by colocalization with a nuclear marker or stain), and/or sensitivity of trafficking to specific inhibitors of early endosomal escape (such as bafilomycin A or ammonium chloride), as compared to fluorescently labeled wild-type AAV particles used to infect the same cell line (see, e.g., Bartlett, J. S. et al. (2000) *J. Virol.* 74:2777-2785 for a description of such assays).

To assay infectivity, AAV particles with capsid proteins having a mutated $2^{nd}$ position (e.g., iMet X) are used to infect cells (e.g., HeLa cells), and their transduction efficiency is compared to wild-type AAV particles (e.g., having the same AAV serotype and infecting the same type of cells).

To assay glycosylation, AAV particles with capsid proteins having a mutated $2^{nd}$ position (e.g., iMet X) are used to infect cells (e.g., HeLa cells). AAV particles from infected cells are subjected to one or more assays including without limitation chemical detection of glycosylation (e.g., applying a commercially available digoxigenin (DIG) glycan detection and/or fluorescent glycoprotein detection kit on denatured and electrophoretically separated capsid proteins) and mass spectrometry (e.g., FT-ICR MS), as compared to wild-type AAV particles used to infect the same cell line (see, e.g., Murray, S. et al. (2006) *J. Virol.* 80:6171-6176 for a description of such assays).

To assay ubiquitination, AAV particles with capsid proteins having a mutated $2^{nd}$ position are used to infect cells (e.g., HeLa cells). AAV particles are immunoprecipitated from infected cells with an anti-capsid antibody, then subjected to Western blotting with an anti-ubiquitin antibody and compared to wild-type AAV particles used to infect cells in the same manner. Mutant AAV particles may also be used in in vitro ubiquitination assays, as compared to wild-type AAV particles (see, e.g., Yan, Z. et al. (2002) *J. Virol.* 76:2043-2053).

Example 3: The Role of Deamidation of AAV2 Capsid Proteins

Sequence analysis of the AAV2 capsid protein revealed potential deamidation sites, as underlined in the following amino acid sequence:

(SEQ ID NO: 3)
MAADGYLPDWLEDTLSEGIRQWWKLKPGPPPPKPAERHKDDSRGLVLPG

YKLGPFNGLDKGEPVNEADAAALEHDKAYDRQLDSGDN

PYLKYNHADA EFQERLKEDTSFGGNLGRAVFQAKKRVLEPLGLVEEPV

KTAPGKKRPVEHSPVEPDSSSGTGKAGQQPARKRLNFGQTGDADSVPDP

QPLGQPPAAPSGLGTNTMATGSGAPMADNNEGADGVGNSSGNWHCDSTW

MGDRVITTSTRTWALPTYNNHLYKQISSQSGASNDNHYFGYSTPWGYFD

FNRFHCHFSPRDWQRLINNNWGFRPKRLNFKLFNIQVKEVTQNDGTTTI

ANNLTSTVQVFTDSEYQLPYVLGSAHQGCLPPFPADVFMVPQYGYLTLN

NGSQAVGRSSFYCLEYFPSQMLRTGNNFTFSYTFEDVPFHSSYAHSQSL

DRLMNPLIDQYLYYLSRTNTPSGTTTQSRLQFSQAGASDIRDQSRNWLP

GPCYRQQRVSKTSADNNNSEYSWTGATKYHLNGRDSLVNPGPAMASHKD

DEEKFFPQSGVLIFGKQGSEKTNVDIEKVMITDEEEIRTTNPVATEQYG

SVSTNLQRGNRQAATADVNTQGVLPGMVWQDRDVYLQGPIWAKIPHTDG

HFHPSPLMGGFGLKHPPPQILIKNTPVPANPSTTFSAAKFASFITQYST

GQVSVEIEWELQKENSKRWNPEIQYTSNYNKSVNVDFTVDTNGVYSEPR

PIGTRYLTRNL

In particular, a potential deamidation site is found at N57/G58 in the phospholipase A2 domain (Ca++ binding site), as bolded and italicized in the above sequence. The following experiments were aimed at exploring whether deamidation at N57 can lead to reduced potency and/or truncation of AAV2, as well as whether different AAV production methods may have different effects on deamidation. For example, the producer cell line method (see Martin et al., (2013) *Human Gene Therapy Methods* 24:253-269; U.S. PG Pub. No. US2004/0224411; and Liu, X. L. et al. (1999) *Gene Ther.* 6:293-299) may induce a higher level of deamidation at N57, as compared to the triple transfection method. According to the crystal structure of AAV2, N57 is not shown; however, N382 and N511 are partially exposed, and N715 is fully exposed.

Methods

Enzymatic Digestions of AAV1 and AAV2 VPs

10 μg of each AAV1-EGFP or AAV2-EGFP material (generated from triple transfection as well as producer cell line process) were concentrated using Amicon filters (10 kDa MWCO), denatured with 6 M Guanidine-HCl, 50 mM Tris at pH 8.5. The proteins were reduced with 5 mM DTT at 60° C. for 30 minutes in darkness, alkylated with 15 mM iodoacetamide at room temperature for 30 minutes, and then buffer exchanged into 25 mM Tris pH 7.1 for digestion using Bio-Spin® 6 Tris micro-columns. After buffer exchange, the samples were split into two aliquots. Each aliquot was digested with trypsin at 1:25 or Asp-N at 1:50 enzyme:protein ratio (wt/wt) for 2 hours at 37° C., respectively.

UPLC/MS/MS Peptide Mapping

The protein digests were also analyzed by UPLC/MS/MS in Acquity UPLC-Xevo qTOF MS. BEH300 C18 column (2.1×150 mm) was used for separation in the mobile phases with 0.1% formic acid in water/acetonitrile gradient at a flow rate 0.25 ml/min. The mass spectra were acquired in the positive MSe resolution mode in the mass range of 50-2000.

Determination of Deamidation Levels in AAV VPs

The extracted ion chromatograms (XIC) of peptides containing NG sites (T9, T49, and T67 in AA1 and AAV2 VP) and their corresponding deamidated species were used for calculation of deamidation levels.

In order to compare AAV vectors produced by the triple transfection (TTx) and producer cell line (PCL) methods, AAV1 or AAV2 tagged with EGFP was produced using the TTx or PCL method. Truncated VP1 (tVP1) was found to be present in AAV2-EGFP produced by PCL, but not in the AAV2-EGFP produced by TTx. AAV1-EGFP was not found to have tVP1, regardless of the production method. The in vitro potency of AAV2 produced by the PCL method was also found to be reduced, as compared to AAV2 produced by TTx. Mutant N57K and N57Q AAV2 particles were also found to have reduced potency and disrupted Ca++ binding.

The following table provides the tryptic peptides that were analyzed to examine each potential deamidation site, as well as the corresponding residue.

TABLE 7

| Tryptic peptides containing NG sites | |
|---|---|
| Peptide (NG sequence underlined) | Residue |
| YLGPFNGLDK (SEQ ID NO: 9) | N57 |
| EVTQNDGTTTIANNLTSTVQVFTDSEYQLPYVLGSAHQGCLPPFPADVFMVPQYGYLTLNGSQAVGRSSFYCLEYFPSQMLR (SEQ ID NO: 10) | N382 |
| YNLNGR (AAV1) (SEQ ID NO: 11) | N511 |
| YHLNGR (AAV2) (SEQ ID NO: 12) | N511 |
| SANVDFTVDNNGLYTEPR (AAV1) (SEQ ID NO: 13) | N715 |
| SVNVDFTVDTNGVYSEPR (AAV2) (SEQ ID NO: 14) | N715 |

As shown in Table 7, the T9 peptide YLGPF NG LDK (SEQ ID NO: 9) was used to monitor N57, the T38 peptide EVTQNDGTTTIANNLTSTVQVFTDSEYQLPYVLGSA-HQGCLPPFPADVFMVPQYGYLTL N NG SQAVGRSS-FYCLEYFPSQMLR (SEQ ID NO: 10) was used to monitor N382, the T49 peptides YNL NG R (SEQ ID NO: 11) and YHL NG R (SEQ ID NO: 12) were used to monitor N511 in AAV1 or AAV2 (respectively), and the T67 peptides SANVDFTVDN NG LYTEPR (SEQ ID NO: 13) and SVNVDFTVDT NG VYSEPR (SEQ ID NO: 14) were used to monitor N715 in AAV1 or AAV2 (respectively).

Figure 6A:
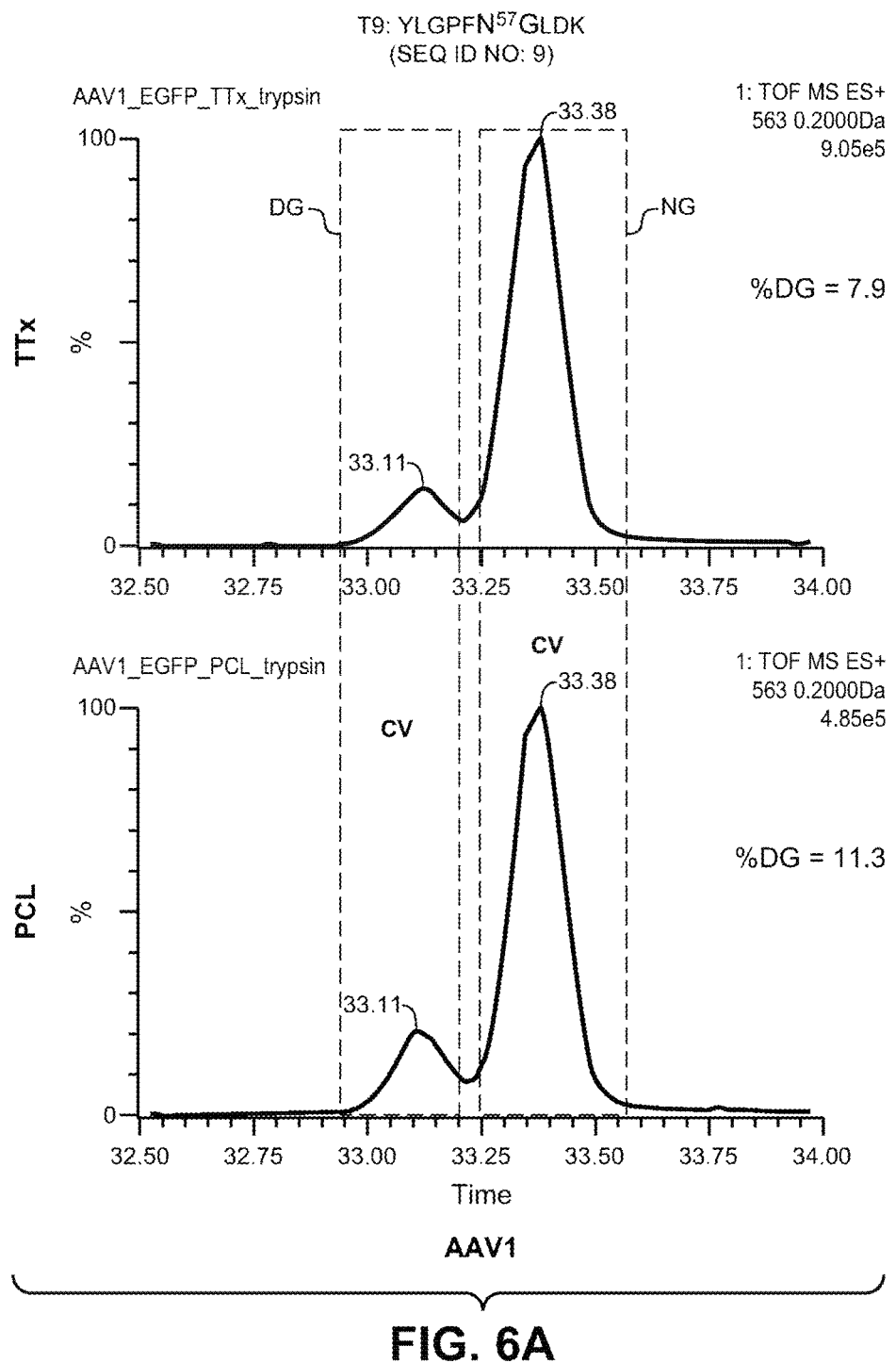
FIGS. 6A & 6B show the results of LC/MS/MS analysis comparing the percentage of deamidation in AAV1 and AAV2 particles produced by the TTx and PCL methods. The T9 peptide YLGPFNG LDK (SEQ ID NO: 9) was used to monitor potential deamidation site N57 in both AAV1 and AAV2.
Figure 6B:
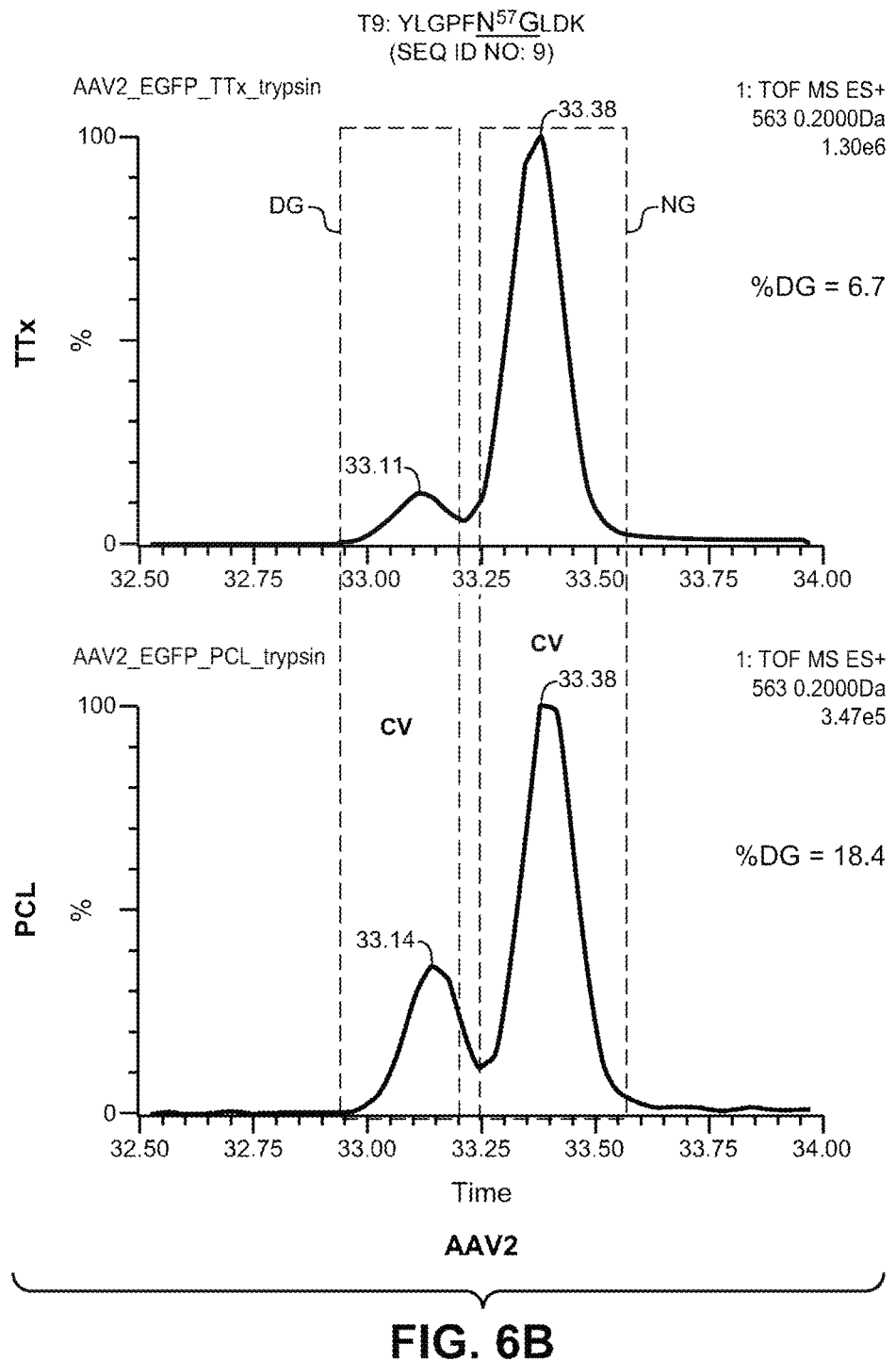
Figure 7A:
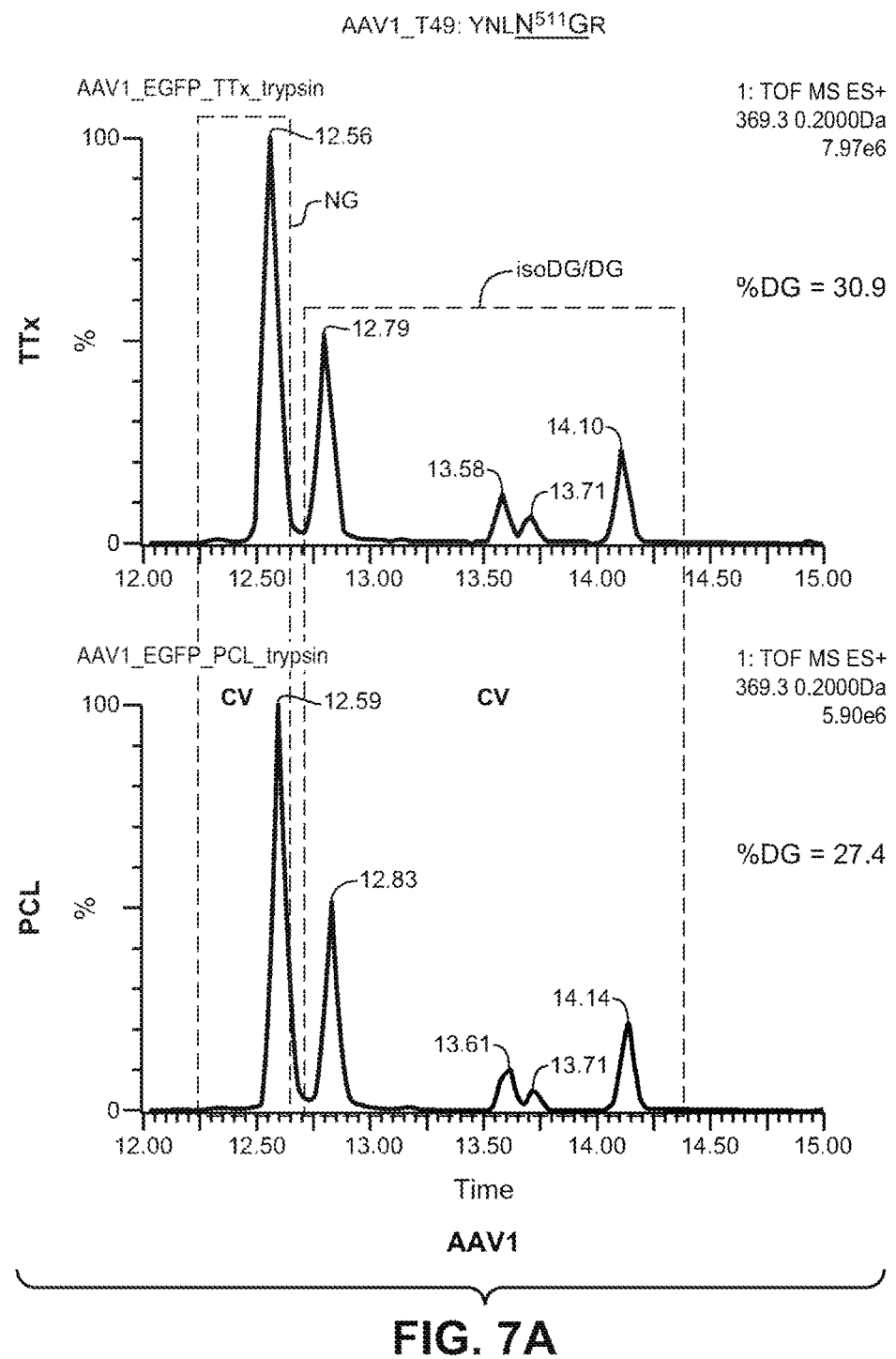
FIGS. 7A & 7B show the results of LC/MS/MS analysis comparing the percentage of deamidation in AAV1 and AAV2 particles produced by the TTx and PCL methods. The T49 peptides YNLNG R (SEQ ID NO: 11) and YHLNG GR (SEQ ID NO: 12) were used to monitor potential deamidation site N511 in AAV1 and AAV2, respectively.
Figure 7B:
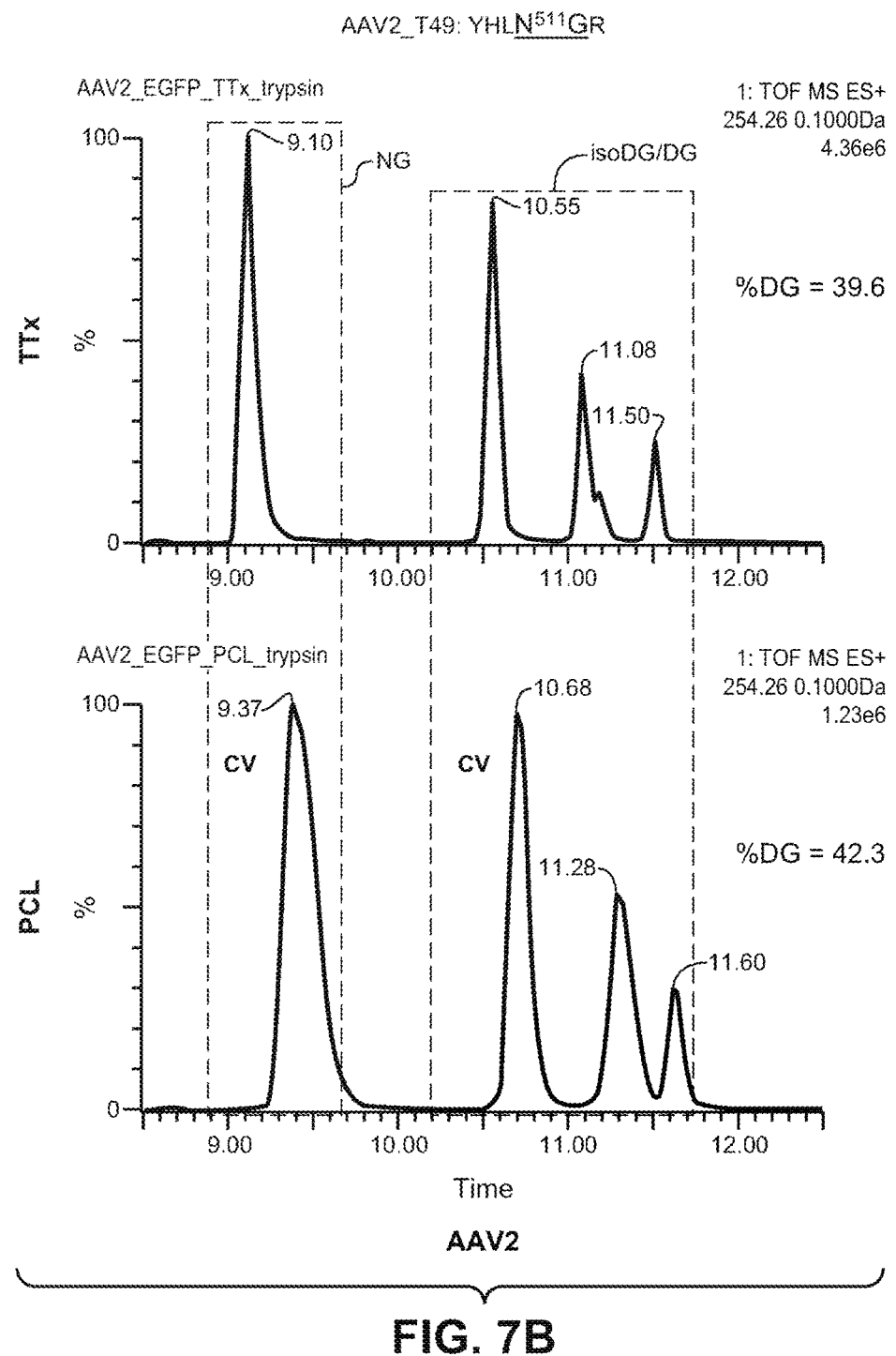
Figure 8A:
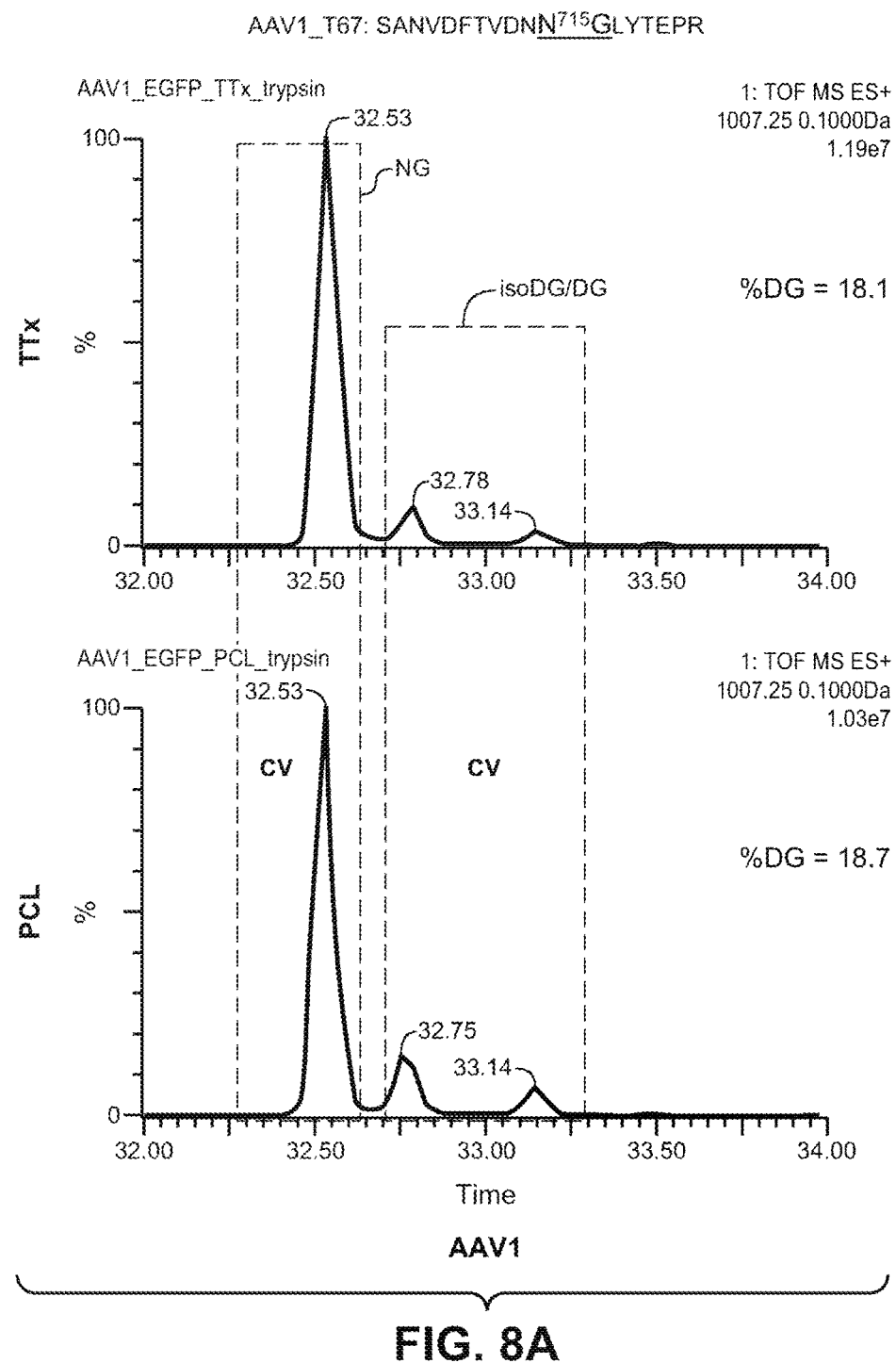
FIGS. 8A & 8B show the results of LC/MS/MS analysis comparing the percentage of deamidation in AAV1 and AAV2 particles produced by the TTx and PCL methods. The T67 peptides SANVDFTVDNNG LYTEPR (SEQ ID NO: 13) and SVNVDFTVDTNG VYSEPR (SEQ ID NO: 14) were used to monitor potential deamidation site N715 in AAV1 and AAV2, respectively.
Figure 8B:
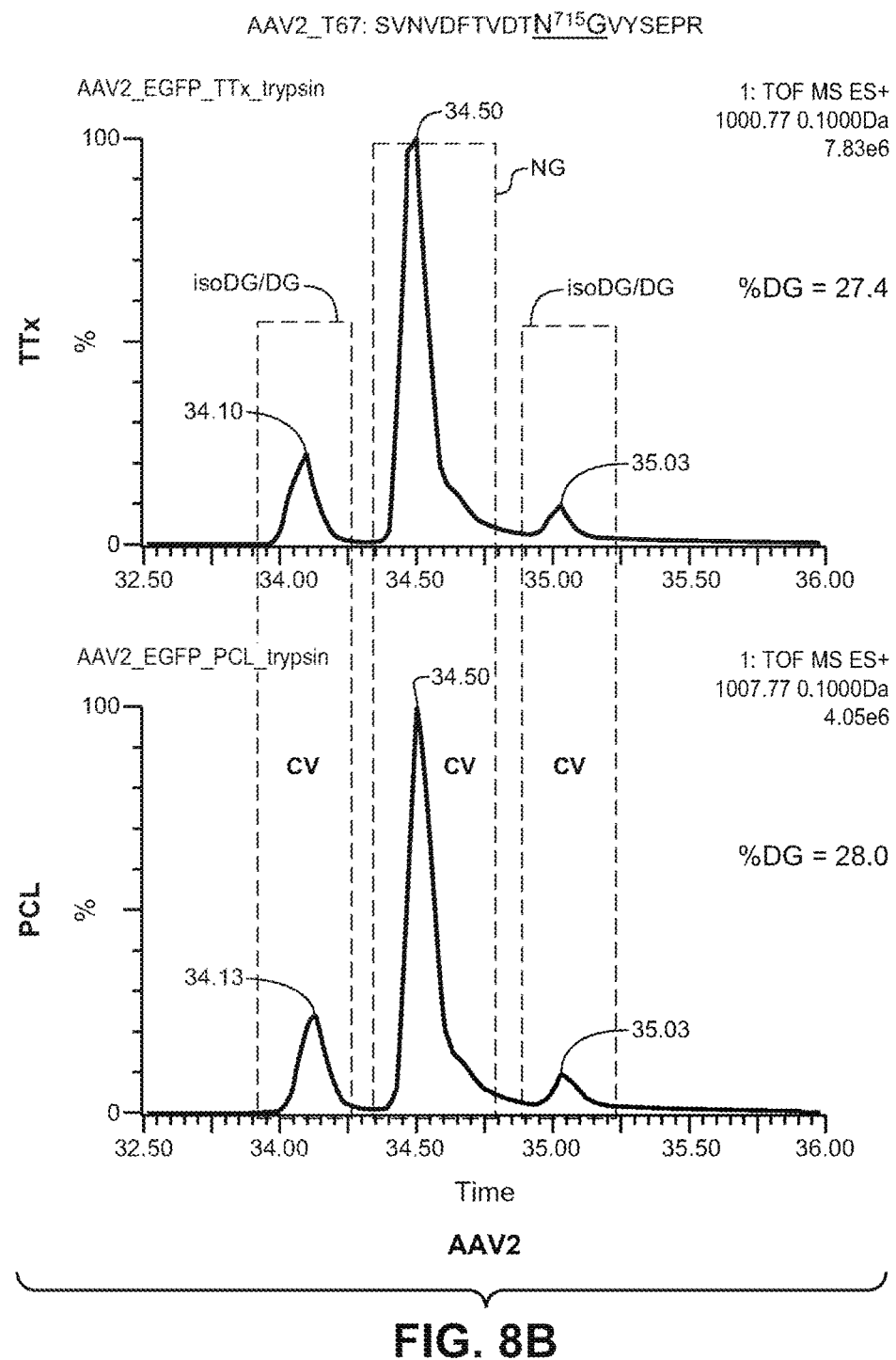

LC/MS/MS analysis was used to compare the percentage of deamidation in AAV1 and AAV2 particles produced by the TTx and PCL methods. The results from the T9 peptide are shown in FIGS. 6A & 6B. The results from the T49 peptide are shown in FIGS. 7A & 7B. The results from the T67 peptide are shown in FIGS. 8A & 8B. These results are summarized in Table 8. The T38 peptide was not detected due to its size.

TABLE 8

| Summary of LC/MS/MS results | | | | |
|---|---|---|---|---|
| | | % Deamidation | | |
| | | N57 | N511 | N715 |
| AAV1 | TTx | 7.9 | 30.9 | 18.1 |
| | PCL | 11.3 | 27.4 | 18.7 |
| AAV2 | TTx | 6.7 | 39.6 | 27.4 |
| | PCL | 18.4 | 42.3 | 28.0 |

In particular, AAV2 produced by PCL showed nearly a 3-fold increase in deamidation as compared to AAV2 produced by TTx. These results suggest that deamidation decreases AAV potency, as the in vitro potency of AAV2 produced by PCL is reduced.

Conclusions

Taken together, Examples 1-3 demonstrate methods for analyzing intact proteins of viral particles (e.g., AAV capsid proteins) using LC/MS. Molecular weights were measured accurately, and these techniques may be also used to assess N-termini and/or modifications of viral capsid proteins. Moreover, these methods are adaptable as capsid serotype identity assays useful in gene therapy, e.g., as an analytical platform. These results further establish a correlation between capsid protein structure (e.g., truncations, deamidation, etc.) and potency, suggesting that point mutations at key sites may be used to engineer more effective vectors.

Example 4: Elucidating the Role of N Terminal Acetylation of AAV Capsid Proteins As discussed above, the N-termini of AAV capsid proteins are highly conserved across serotypes (FIG. 5). The techniques described in Example 1 allow for interrogation of VP expression and posttranslational modifications. The role and biological significance of N-terminal acetylation of AAV capsid proteins was next examined.

Results

To elucidate the potential role of deacetylation of AAV capsid proteins, AAV5 deacetylation variants were tested. An AAV5 particle expressing eGFP under the CBA promoter (AAV5-CBA-Egfp) was compared to AAV5 variants with the amino acid adjacent to the initiating methionine (iMET) mutated for VP1 and VP3 (deAC-AAV5-CBA-eGFPs). Three amino acids predicted to have a low likelihood of acetylation by NatA, NatC, or NatD were chosen for generating variants: Gly, Leu, and Pro, as illustrated in Table 9 below.

TABLE 9

N-terminal acetylation frequency

| N-term aa | Transferase | NT-AC FREQUENCY |
|---|---|---|
| MET-ALA Normally found in VP1 & VP3 | NatA | High |
| MET-SER Normally found in | NatA | High |

S2LVP1/VP3—Ser changed to Leu at position 2 in both AAV5 VP1 and VP3

These variants were generated using the TTX method as described above. All AAV5 variants showed good productivity, with yields greater than $10^{13}$ total VG. All AAV5 variants also showed the expected VP1:VP2:VP3 protein ratio by SYPRO protein gel analysis (FIG. 9). Next, LC/MS was used to confirm that all AAV5 variants had decreased acetylation, as shown in Table 10.

TABLE 10

LC/MS analysis of AAV5 variant acetylation

| | mutants | VP1 Theo. | VP1 Exp. | Δmass (VP1) | VP2 Theo. | VP2 Exp. | Δmass (VP2) | VP3 Theo. | VP3 Exp. | Δmass (VP3) | note |
|---|---|---|---|---|---|---|---|---|---|---|---|
| 1 | deAC-AAV5 (S2GVP1)/ CBA-eGFP | 80234 | nd | | 65283 | 65293 | 10 | 59463 | 59472 | 9 | VP1 not detectable |
| 2 | deAC-AAV5 (S2LVP1)/ CBA-eGFP | 80346 | 80501 | 181 | 65283 | 65292 | 9 | 59463 | 59471 | 8 | VP1 incorrect |
| 3 | deAC-AAV5 (S2GVP3)/ CBA-eGFP | 80234 | nd | | 65253 | 65261 | 8 | 59391 | 59398 | 7 | confirmed |
| 4 | deAC-AAV5 (S2LVP3)/ CBA-eGFP | 80336 | 80363 | 27 | 65309 | 65309 | 0 | 59447 | 59620 | 173 | VP3 incorrect |
| 5 | deAC-AAV5 (S2PVP1VP3)/ CBA-eGFP | 80314 | 80324 | 10 | 65293 | 65300 | 7 | 59431 | 59438 | 7 | confirmed |
| 6 | deAC-AAV5 (S2GVP1VP3)/ CBA-eGFP | 80234 | 80243 | 9 | 65253 | 65261 | 8 | 59391 | 59398 | 7 | confirmed |
| 7 | deAC-AAV5 (S2PVP3)/ CBA-eGFP | 80336 | 80346 | 10 | 65293 | 65292 | 1 | 59431 | 59430 | 1 | confirmed |
| 8 | deAC-AAV5 (S2PVP1)/ CBA-eGFP | 80314 | 80313 | 1 | 65283 | 65291 | 8 | 59463 | 59470 | 7 | confirmed |
| 9 | deAC-AAV5 (S2L VP1VP3)/ CBA-eGFP | 80346 | nd | | 65309 | 65318 | 9 | 59447 | 59629 | 182 | VP3 incorrect | nd = not determined

TABLE 9-continued

N-terminal acetylation frequency

| N-term aa | Transferase | NT-AC FREQUENCY |
|---|---|---|
| VP1 & VP3 for AAV5 AAV variants | | |
| MET-GLY | NatA | Low |
| MET-LEU | NatC | Low |
| MET-PRO | NatD/other | Low |

The following AAV5 deacetylated (deAC) mutants were generated:
S2GVP1—Ser changed to Gly at position 2 in AAV5VP1
S2LVP1—Ser changed to Leu at position 2 in AAV5VP1
S2PVP1—Ser changed to Pro at position 2 in AAV5VP1
S2GVP3—Ser changed to Gly at position 2 in AAV5VP3
S2LVP3—Ser changed to Leu at position 2 in AAV5VP3
S2PVP3—Ser changed to Pro at position 2 in AAV5VP3
S2PVP1/VP3—Ser changed to Pro at position 2 in both AAV5 VP1 and VP3
S2GVP1/VP3—Ser changed to Gly at position 2 in both AAV5 VP1 and VP3

These LC/MS analyses confirmed that AAV5 variants were deacetylated. The variants S2LVP1, S2LVP3, and S2LVP1/VP3 all showed increased mass (increased from 173 to 182) in VP1 and VP3 proteins, suggesting that changing the second N-terminal amino acid to a leucine in VP1 or VP3 alters the protein, resulting in an increase in mass.

Figure 10:
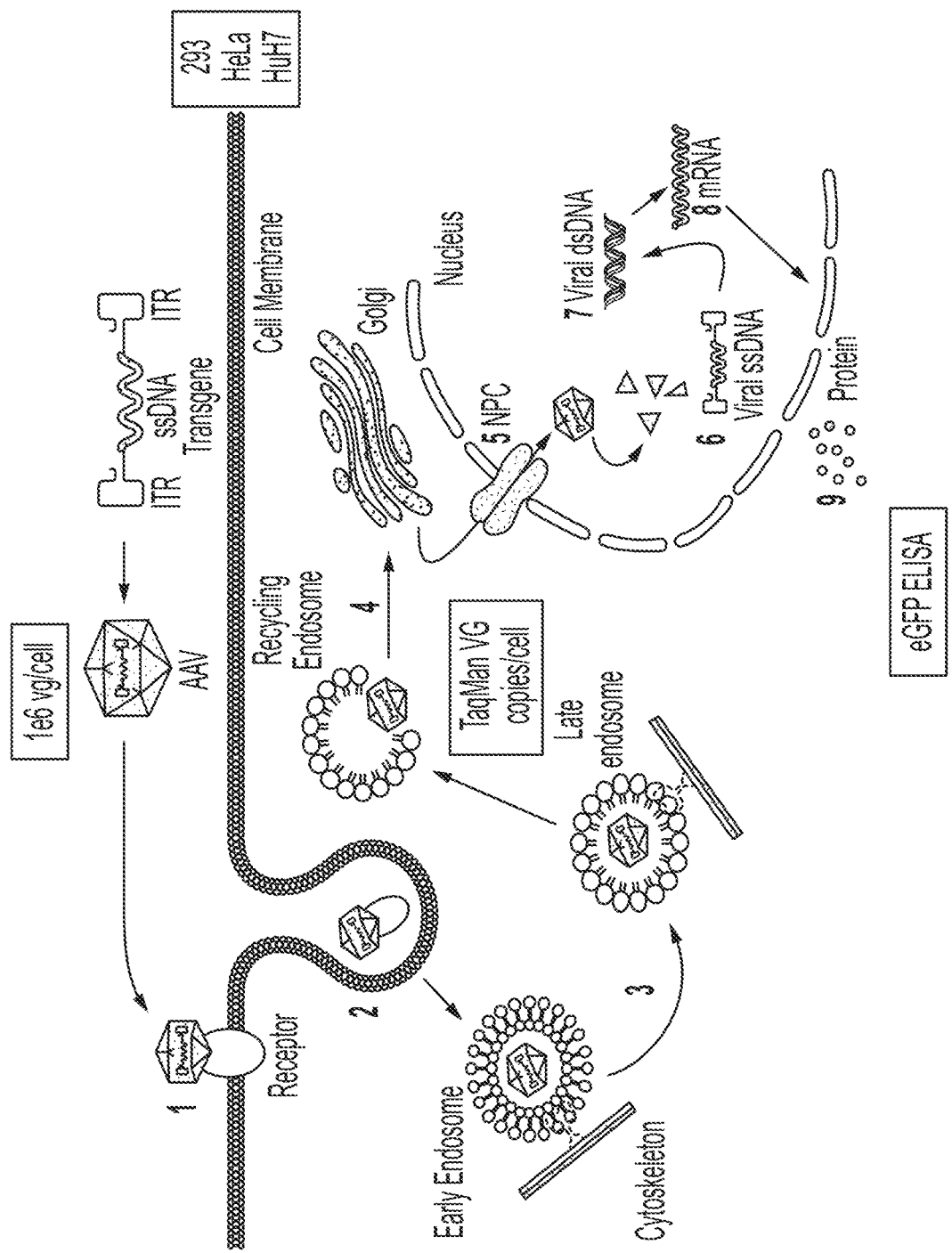
FIG. 10 illustrates an in vitro transduction assay for testing transduction efficiency of AAV5 deacetylated variants.

Next, AAV5 variants were assayed in an in vitro transduction assay using eGFP as a reporter gene (FIG. 10). The assay was designed to evaluate transduction by AAV5 deacetylated mutant variants at $10^6$ multiplicity of infection (MOI), comparing each variant to the parental, unmodified AAV5 particle. Three cell lines were used: 293, HuH7, and HeLa cells. Following infection, cells were assayed to determine vector genome copy number (vg/μg cellular protein) and eGFP expression (by ELISA). Vector genome copy number (vg/μg protein) represents the efficiency at which the AAV5 variant enters the cell, and eGFP represents the efficiency of capsid intracellular trafficking, since transgene expression requires the capsid/vector DNA to efficiently traffic to the nucleus (FIG. 10). Vector genomes were quantified by TaqMan analysis.

Figure 11:
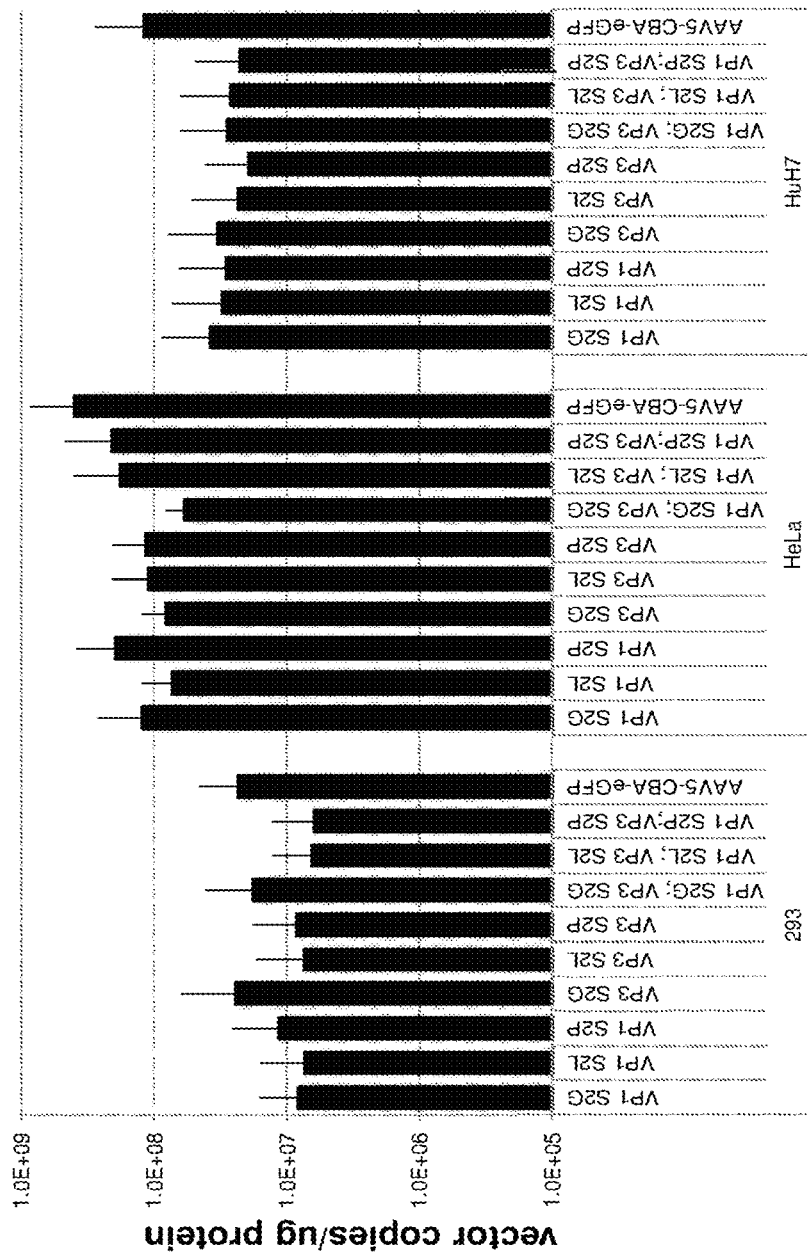
FIG. 11 shows the efficiency of cell entry by the indicated AAV5 deacetylated variants or parental unmodified AAV5, as measured by vector genome copies/µg protein. Three cell lines were used: 293, HeLa, and HuH7.
Figure 12:
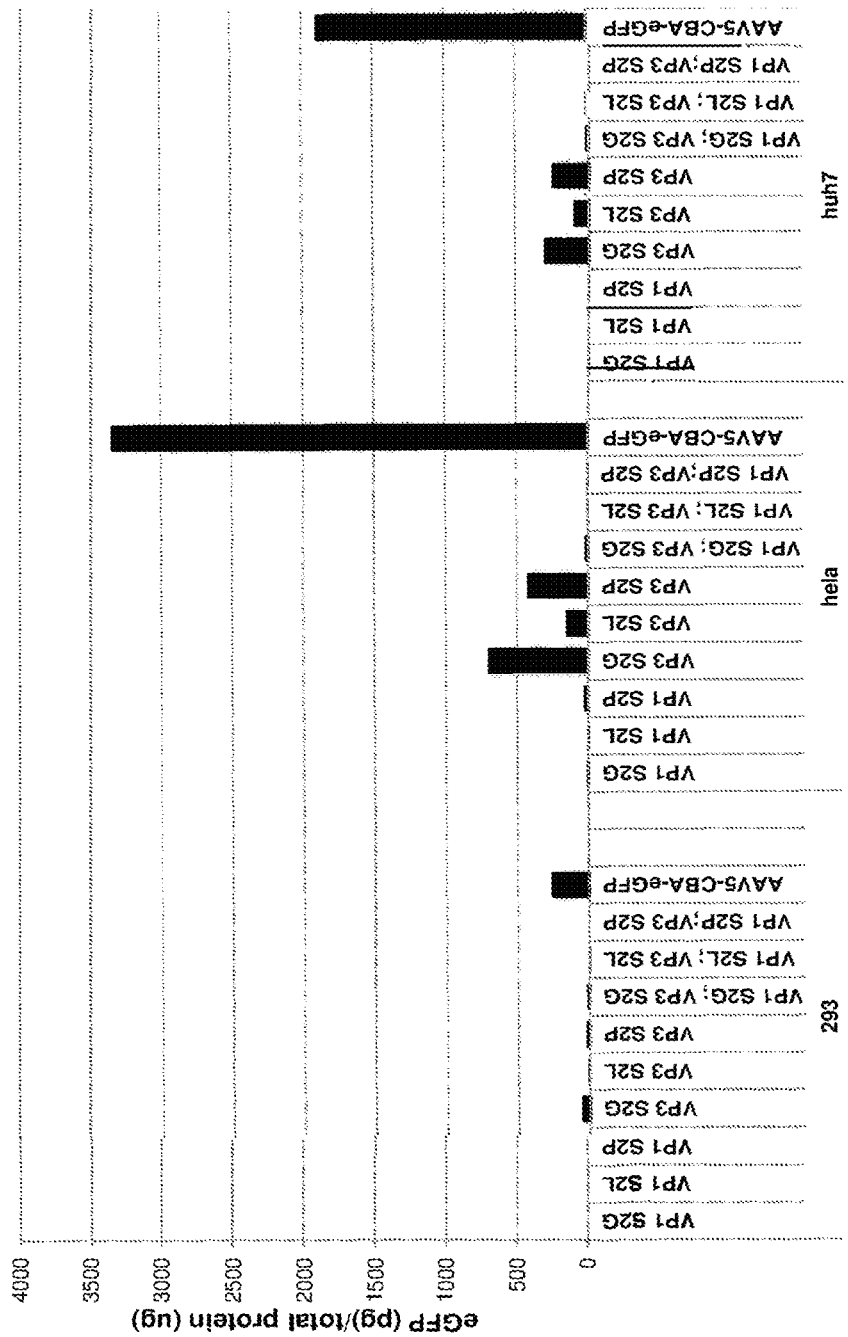
FIG. 12 shows eGFP expression (as measured by ELISA) by cells transduced with the indicated AAV5 deacetylated variants as compared to transduction with parental unmodified AAV5. Three cell lines were used: 293, HeLa, and HuH7.

FIG. 11 shows that, based on vector genome analyses, AAV5 deacetylated mutant vectors infected all three test cell lines at similar, but reduced, levels as compared to the parental unmodified AAV5 particles. FIG. 12 shows that AAV5 deacetylated mutant vectors all resulted in reduced eGFP expression in all three cell lines, as compared to transduction with parental unmodified AAV5.

Conclusions

As predicted, no acetylation was observed in N-terminal Ser to Pro/Leu/Gly mutant variants when examined by LC/MS. AAV5 deAC variants showed robust vector production, and AAV5 deAC variants infected cells at levels comparable to parental AAV5. However, functional protein levels in cells infected with deAC variants were greatly reduced when compared to the parental AAV5. These data suggest that tropism is minimally affected by a lack of N-terminal deacetylation in VP1/VP3, but downstream processing (e.g., trafficking and/or degradation) is significantly affected. Since the variants tested demonstrated reduced in vitro activity, one of skill in the art may appreciate that variants characterized by reduced or eliminated acetylation could be employed, inter alia, when decreased levels of transduction are desirable.

Example 5: Assessment of Deamidation of AAV Capsid Proteins

Examples 1 and 3 demonstrate techniques that allow the interrogation of post-translational modifications of AAV capsid proteins and explore the role of deamidation of the AAV2 capsid. The following Example tested whether deamidation reduces potency and/or induces truncation of capsid proteins, and whether different manufacturing processes can induce different levels of deamidation.

Methods

AAV particles were generated and deamidation status assayed as described in Example 3.

Results

Figure 13:
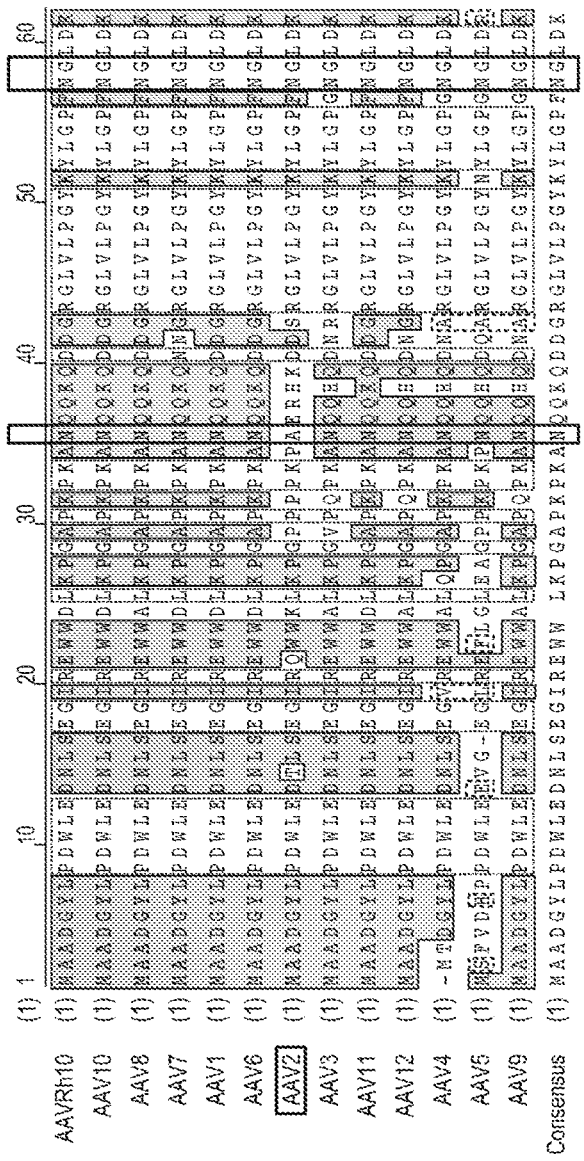
FIG. 13 provides the sequence alignment of 13 AAV serotypes, highlighting the conserved N57G58 deamidation site and the A35 residue in AAV2. AAVRh10 (SEQ ID NO: 31); AAV10 (SEQ ID NO: 31); AAV8 (SEQ ID NO: 32); AAV7 (SEQ ID NO: 33); AAV1 (SEQ ID NO: 31); AAV6 (SEQ ID NO: 31); AAV2 (SEQ ID NO: 34); AAV3 (SEQ ID NO: 35); AAV11 (SEQ ID NO: 31); AAV12 (SEQ ID NO: 36); AAV4 (SEQ ID NO: 37); AAV5 (SEQ ID NO: 38); AAV9 (SEQ ID NO: 39); Consensus (SEQ ID NO: 40).

As described in Example 3, a potential deamidation site is found at N57/G58 in the phospholipase A2 domain (Ca++ binding site) in VP1 of the AAV2 capsid. The N57/G58 motif is conserved across AAV serotypes (FIG. 13). Example 3 showed that AAV2 produced by PCL exhibited nearly a 3-fold increase in deamidation as compared to AAV2 produced by TTx (see FIGS. 6A & 6B and Table 8).

Figure 14:
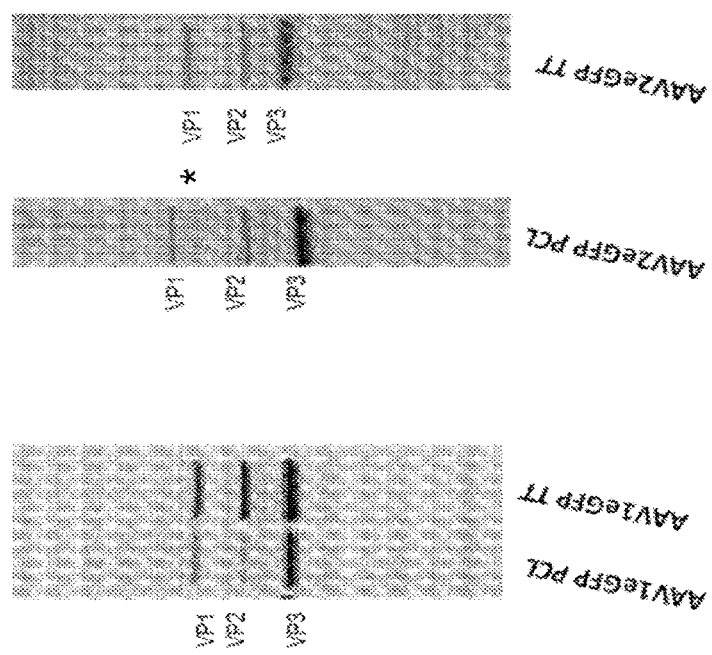
FIG. 14 shows a protein gel of VP1, VP2, and VP3 capsid proteins from AAV1 or AAV2 particles produced by the PCL or TTx method. *highlights the truncated VP1 (tVP1) protein.

In examining VP1, VP2, and VP3 production by protein gels, a truncated VP1 protein (tVP1) was detected only in AAV2 capsid proteins produced by the PCL method (FIG. 14).

A series of AAV2 deamidation mutants was generated next. These mutants targeted the Gly residue in the canonical NG sequence. Mutations targeting the A35 residue (see FIG. 13), the N-terminal amino acid for tVP1 were also generated, as shown in Table 11. The pAF277 and pAF279 mutants bearing multiple mutations did not package.

TABLE 11

Deamidation mutants

| Name | mutation | avg drp/cell |
|---|---|---|
| pAF274 | G58K | 4.54E+03 |
| pAF275 | G58D | 5.00E+03 |
| pAF276 | G58Q | 5.41E+03 |
| pAF277 | G58, 383, 512, 716K | 1.2 |
| pAF278 | A35N | 6.89E+03 |
| pAF279 | A35N, G58, 383, 512, 765K | 2.2 |
| 293 | — | 0.9 |
| PIM45 | Control | 6.28E+03 |

K = positive charge (basic)
D = negative charge (acidic)
Q = polar

Figure 16:
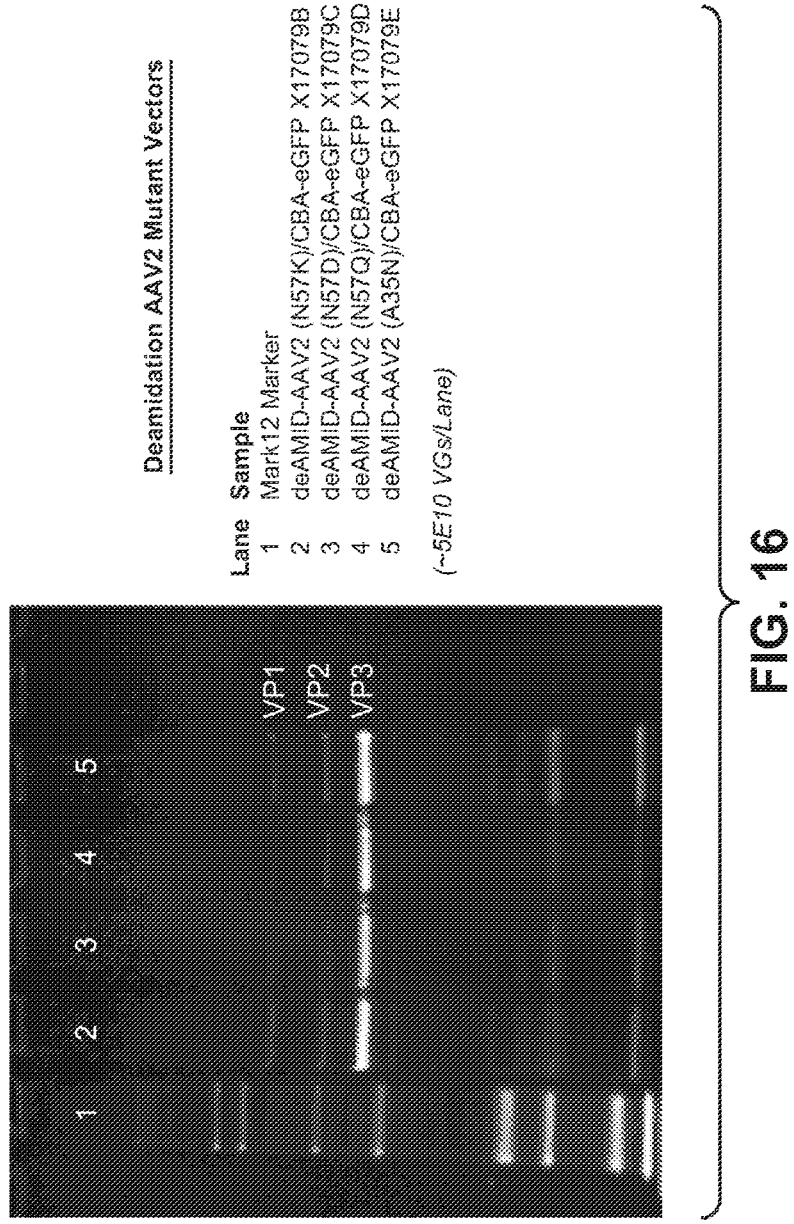
FIG. 16 shows the results of SYPRO protein gel analysis of production and VP1:VP2:VP3 ratio of AAV2 deamidation mutant variants.

Deamidation of variants were next analyzed by LC/MS as described in Example 3 above. The AAV2A35N and AAV2G58D variants had altered deamidation as compared to the parental AAV2 (FIG. 15). In particular, the AAV2A35N mutant had increased deamidation (17.8%) as compared to parental AAV2 (5.7%). The AAV2G58D variant had reduced deamidation (1.1%) as compared to parental AAV2. SYPRO protein gel analysis demonstrated that the AAV2 deamidation mutants exhibited the correct VP1:VP2:VP2 ratio (FIG. 16).

Figure 17:
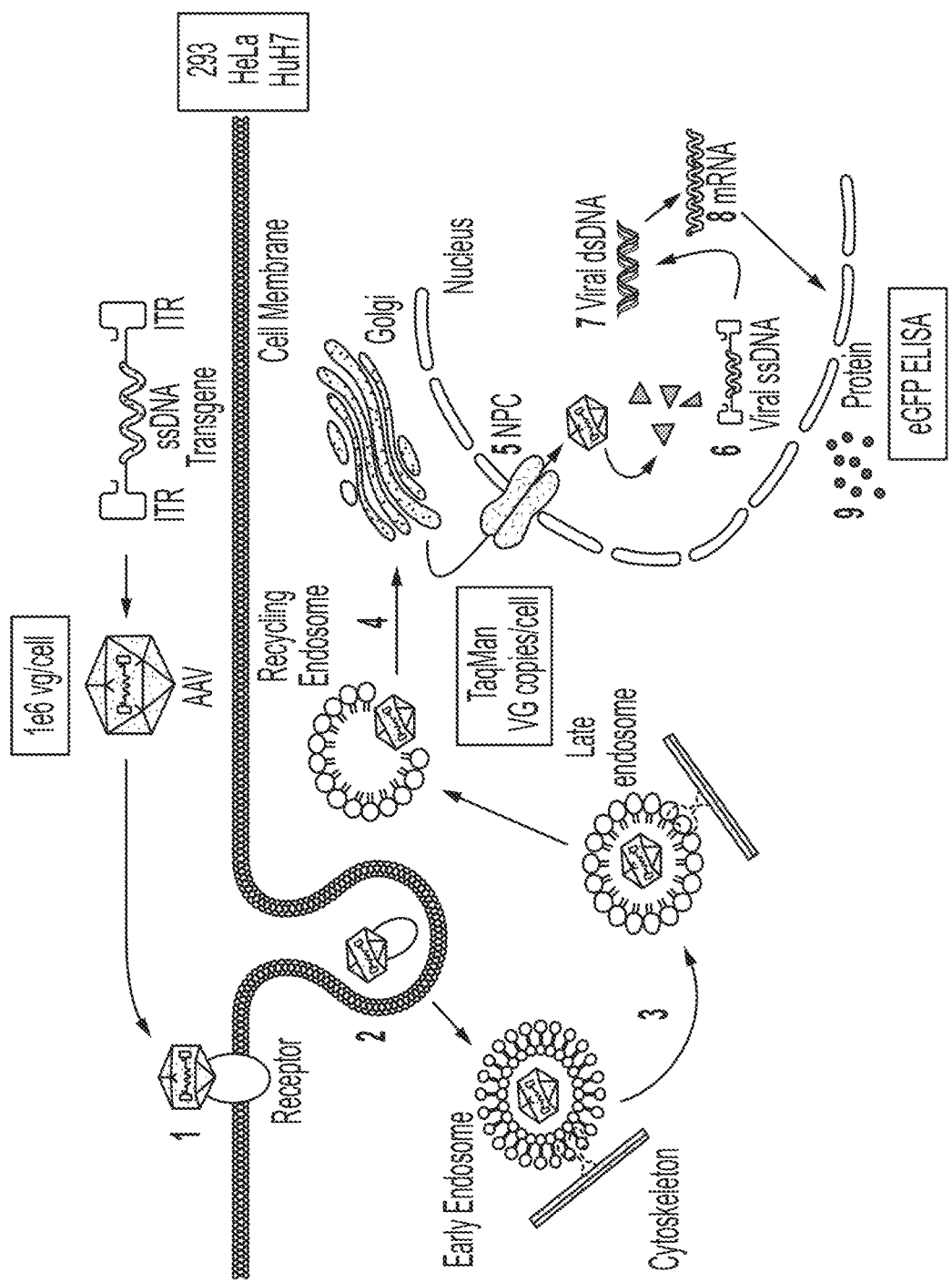
FIG. 17 illustrates an in vitro transduction assay for testing transduction efficiency of AAV2 deamidation variants.

Next, AAV2 deamidation variants were assayed in an in vitro transduction assay using eGFP as a reporter gene (FIG. 17). The assay was designed to evaluate transduction by AAV2 deamidation mutant variants at $10^6$ multiplicity of infection (MOI), comparing each variant to the parental, unmodified AAV2 particle. Three cell lines were used: 293, HuH7, and HeLa cells. Following infection, cells were assayed to determine vector genome copy number (vg/µg cellular protein) and eGFP expression (by ELISA). Vector genome copy number (vg/µg protein) represents the efficiency at which the AAV2 variant enters the cell, and eGFP represents the efficiency of capsid intracellular trafficking, since transgene expression requires the capsid/vector DNA to efficiently traffic to the nucleus (FIG. 17). Vector genomes were quantified by TaqMan analysis.

Figure 18:
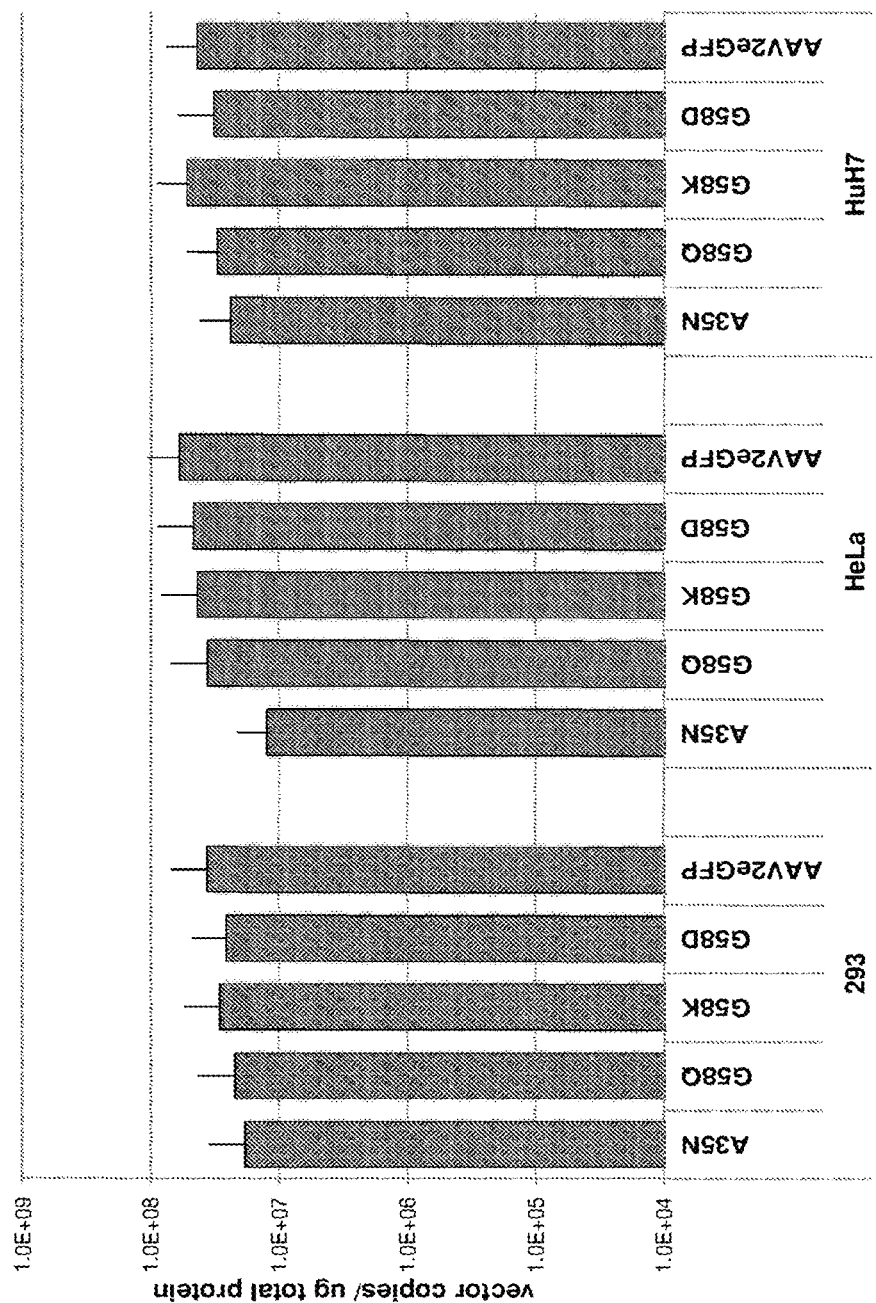
FIG. 18 shows the efficiency of cell entry by the indicated AAV2 deamidation variants or parental unmodified AAV2, as measured by vector genome copies/µg protein. Three cell lines were used: 293, HeLa, and HuH7.
Figure 19:
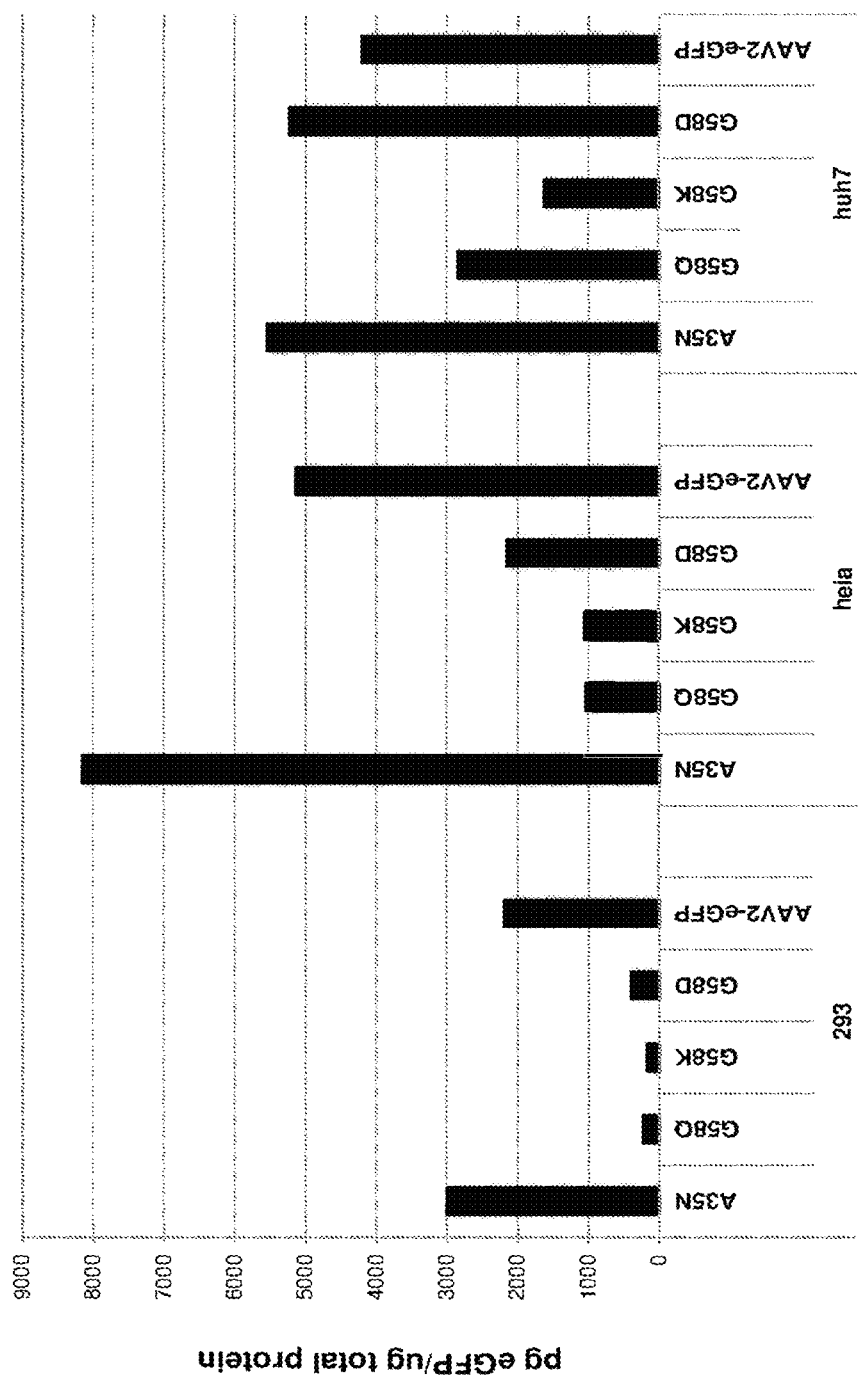
FIG. 19 shows eGFP expression (as measured by ELISA) by cells transduced with the indicated AAV2 deamidation variants as compared to transduction with parental unmodified AAV2. Three cell lines were used: 293, HeLa, and HuH7.

Vector genome analysis indicated that AAV2 deamidation mutant variants infected all cell lines tested at levels comparable to that of parental AAV2 vectors (FIG. 18). Importantly, the AAV2A35N variant was found to be more potent than the parental AAV2 vector for transduction in all three cell lines (FIG. 19). The AAV2G58D variant was found to be more potent than the parental AAV2 vector in HuH7 cells (FIG. 19).

Conclusions

In summary, AAV2 deamidation mutant vectors infect cells at levels comparable to the parent AAV2 particles (e.g., comparable vg/µg cellular protein). However, based on analysis of eGFP levels in transduced cells, the AAV2A35N variant had higher potency than the parental AAV2 in all cell lines tested, and the AAV2G58D variant had higher potency than the parental AAV2 in HuH7 cells (a liver-derived cell line). These results suggest that the A35N mutation may be effective in increasing vector potency for transducing many cell types, and that the G58D mutation may also be effective in increasing potency in certain cell types, e.g., liver cells.

REFERENCES

1. Girod, A., et al., *The VP1 capsid protein of adeno-associated virus type 2 is carrying a phospholipase A2 domain required for virus infectivity*. J Gen Virol, 2002. 83(Pt 5): p. 973-8.
2. Stahnke, S., et al., *Intrinsic phospholipase A2 activity of adeno-associated virus is involved in endosomal escape of incoming particles*. Virology, 2011. 409 (1): p. 77-83.
3. Bleker, S., F. Sonntag, and J. A. Kleinschmidt, *Mutational analysis of narrow pores at the fivefold symmetry axes of adeno-associated virus type 2 capsids reveals a dual role in genome packaging and activation of phospholipase A2 activity*. J Virol, 2005. 79 (4): p. 2528-40.
4. Popa-Wagner, R., et al., *Impact of VP1-specific protein sequence motifs on adeno-associated virus type 2 intracellular trafficking and nuclear entry*. J Virol, 2012. 86 (17): p. 9163-74.
5. Kashiwakura, Y., et al., *Hepatocyte growth factor receptor is a coreceptor for adeno-associated virus type 2 infection*. J Virol, 2005. 79 (1): p. 609-14.

6. Qing, K., et al., *Human fibroblast growth factor receptor 1 is a co-receptor for infection by adeno-associated virus 2*. Nat Med, 1999. 5 (1): p. 71-7.

7. Sanlioglu, S., et al., *Endocytosis and nuclear trafficking of adeno-associated virus type 2 are controlled by rac1 and phosphatidylinositol-3 kinase activation*. J Virol, 2000. 74 (19): p. 9184-96.

8. Summerford, C., J. S. Bartlett, and R. J. Samulski, *AlphaVbeta5 integrin: a co-receptor for adeno-associated virus type 2 infection*. Nat Med, 1999. 5 (1): p. 78-82.

9. Kern, A., et al., *Identification of a Heparin-Binding Motif on Adeno-Associated Virus Type 2 Capsids*. J Virol, 2003. 77 (20): p. 11072-11081.

10. Asokan, A., et al., *Adeno-associated virus type 2 contains an integrin alpha5beta1 binding domain essential for viral cell entry*. J Virol, 2006. 80 (18): p. 8961-9.

11. Xie, Q., et al., *The atomic structure of adeno-associated virus (AAV-2), a vector for human gene therapy*. Proc Natl Acad Sci USA, 2002. 99 (16): p. 10405-10.

12. DiMattia, M. A., et al., *Structural insight into the unique properties of adeno-associated virus serotype 9*. J Virol, 2012. 86 (12): p. 6947-58.

13. Nam, H. J., et al., *Structure of adeno-associated virus serotype 8, a gene therapy vector*. J Virol, 2007. 81 (22): p. 12260-71.

14. Kronenberg, S., et al., *A conformational change in the adeno-associated virus type 2 capsid leads to the exposure of hidden VP1 N termini*. J Virol, 2005. 79 (9): p. 5296-303.

15. Sonntag, F., et al., *Adeno-associated virus type 2 capsids with externalized VP1/VP2 trafficking domains are generated prior to passage through the cytoplasm and are maintained until uncoating occurs in the nucleus*. J Virol, 2006. 80 (22): p. 11040-54.

16. Murray, S., et al., *Characterization of the capsid protein glycosylation of adeno-associated virus type 2 by high-resolution mass spectrometry*. J Virol, 2006. 80 (12): p. 6171-6.

17. Salganik, M., et al., *Evidence for pH-dependent protease activity in the adeno-associated virus capsid*. J Virol, 2012. 86 (21): p. 11877-85.

18. Van Vliet, K., et al., *Adeno-associated virus capsid serotype identification: Analytical methods development and application*. J Virol Methods, 2009. 159 (2): p. 167-77.

19. Thomas, J. J., et al., *Viral characterization by direct analysis of capsid proteins*. Anal Chem, 1998. 70 (18): p. 3863-7.

20. Wang, L., L. C. Lane, and D. L. Smith, *Detecting structural changes in viral capsids by hydrogen exchange and mass spectrometry*. Protein Sci, 2001. 10 (6): p. 1234-43.

21. Hwang, C. S., A. Shemorry, and A. Varshavsky, *N-terminal acetylation of cellular proteins creates specific degradation signals*. Science, 2010. 327 (5968): p. 973-7.

22. Yan, Z., et al., *Ubiquitination of both Adeno-Associated Virus Type 2 and 5 Capsid Proteins Affects the Transduction Efficiency of Recombinant Vectors*. J Virol, 2002. 76 (5): p. 2043-2053.

SEQUENCES

All polypeptide sequences are presented N-terminal to C-terminal unless otherwise noted.

All nucleic sequences are presented 5' to 3' unless otherwise noted.

```
Nucleotide sequence of potential AAV2 VP3
initiation codons (ATG codons underlined)
                                         (SEQ ID NO: 1)
ATGGCTACAGGCAGTGGCGCACCAATGGCAGAC Polypeptide sequence corresponding to potential
AAV2 VP3 initiation codons (methionines
underlined)
                                         (SEQ ID NO: 2)
MATGSGAPMAD AAV2 VP1 polypeptide sequence
                                         (SEQ ID NO: 3)
MAADGYLPDWLEDTLSEGIRQWWKLKPGPPPPKPAERHKDDSRGLVLPG

YKYLGPFNGLDKGEPVNEADAAALEHDKAYDRQLDSGDNPYLKYNHADA

EFQERLKEDTSFGGNLGRAVFQAKKRVLEPLGLVEEPVKTAPGKKRPVE

HSPVEPDSSSGTGKAGQQPARKRLNFGQTGDADSVPDPQPLGQPPAAPS

GLGTNTMATGSGAPMADNNEGADGVGNSSGNWHCDSTWMGDRVITTSTR

TWALPTYNNHLYKQISSQSGASNDNHYFGYSTPWGYFDFNRFHCHFSPR

DWQRLINNNWGFRPKRLNFKLFNIQVKEVTQNDGITTIANNLTSTVQVF

TDSEYQLPYVLGSAHQGCLPPFPADVFMVPQYGYLTLNNGSQAVGRSSF

YCLEYFPSQMLRTGNNFTFSYTFEDVPFHSSYAHSQSLDRLMNPLIDQY

LYYLSRINTPSGTTTQSRLQFSQAGASDIRDQSRNWLPGPCYRQQRVSK

TSADNNNSEYSWTGATKYHLNGRDSLVNPGPAMASHKDDEEKFFPQSGV

LIFGKQGSEKTNVDIEKVMITDEEEIRTTNPVATEQYGSVSTNLQRGNR

QAATADVNTQGVLPGMVWQDRDVYLQGPIWAKIPHTDGHFHPSPLMGGF

GLKHPPPQILIKNTPVPANPSTTFSAAKFASFITQYSTGQVSVEIEWEL

QKENSKRWNPEIQYTSNYNKSVNVDFTVDINGVYSEPRPIGTRYLTRNL

VP1 N-terminal tryptic peptide (N-terminal
alanine is acetylated)
                                         (SEQ ID NO: 4)
AADGYLPDWLEDTLSEGIR VP3 N-terminal Asp-N peptide (N-terminal alanine
is acetylated)
                                         (SEQ ID NO: 5)
ATGSGAPM Common VP1 N-terminal sequence
                                         (SEQ ID NO: 6)
MAADGYLPDWLED Nucleotide sequence of potential AAV7 VP3
initiation codons (start codons underlined)
                                         (SEQ ID NO: 7)
GTGGCTGCAGGCGGTGGCGCACCAATGGCAGACAATAAC Nucleotide sequence of mutated ITR
                                         (SEQ ID NO: 8)
CACTCCCTCTCTGCGCGCTCGCTCGCTCACTGAGGCCGGGCGACCAAAG
GTCGCCCACGCCCGGGCTTTGCCCGGGCG
```

SEQUENCE LISTING

```
Sequence total quantity: 40
SEQ ID NO: 1                    moltype = DNA  length = 33
FEATURE                         Location/Qualifiers
misc_feature                    1..33
                                note = Synthetic Construct
source                          1..33
                                mol_type = other DNA
                                organism = synthetic construct
SEQUENCE: 1
atggctacag gcagtggcgc accaatggca gac                                           33

SEQ ID NO: 2                    moltype = AA  length = 11
FEATURE                         Location/Qualifiers
REGION                          1..11
                                note = Synthetic Construct
source                          1..11
                                mol_type = protein
                                organism = synthetic construct
SEQUENCE: 2
MATGSGAPMA D                                                                   11

SEQ ID NO: 3                    moltype = AA  length = 735
FEATURE                         Location/Qualifiers
source                          1..735
                                mol_type = protein
                                organism = Adeno-associated virus 2
SEQUENCE: 3
MAADGYLPDW LEDTLSEGIR QWWKLKPGPP PPKPAERHKD DSRGLVLPGY KYLGPFNGLD              60
KGEPVNEADA AALEHDKAYD RQLDSGDNPY LKYNHADAEF QERLKEDTSF GGNLGRAVFQ             120
AKKRVLEPLG LVEEPVKTAP GKKRPVEHSP VEPDSSSGTG KAGQQPARKR LNFGQTGDAD             180
SVPDPQPLGQ PPAAPSGLGT NTMATGSGAP MADNNEGADG VGNSSGNWHC DSTWMGDRVI             240
TTSTRTWALP TYNNHLYKQI SSQSGASNDN HYFGYSTPWG YFDFNRFHCH FSPRDWQRLI             300
NNNWGFRPKR LNFKLFNIQV KEVTQNDGTT TIANNLTSTV QVFTDSEYQL PYVLGSAHQG             360
CLPPFPADVF MVPQYGYLTL NNGSQAVGRS SFYCLEYFPS QMLRTGNNFT FSYTFEDVPF             420
HSSYAHSQSL DRLMNPLIDQ YLYYLSRTNT PSGTTTQSRL QFSQAGASDI RDQSRNWLPG             480
PCYRQQRVSK TSADNNNSEY SWTGATKYHL NGRDSLVNPG PAMASHKDDE EKFFPQSGVL             540
IFGKQGSEKT NVDIEKVMIT DEEEIRTTNP VATEQYGSVS TNLQRGNRQA ATADVNTQGV             600
LPGMVWQDRD VYLQGPIWAK IPHTDGHFHP SPLMGGFGLK HPPPQILIKN TPVPANPSTT             660
FSAAKFASFI TQYSTGQVSV EIEWELQKEN SKRWNPEIQY TSNYNKSVNV DFTVDTNGVY             720
SEPRPIGTRY LTRNL                                                             735

SEQ ID NO: 4                    moltype = AA  length = 19
FEATURE                         Location/Qualifiers
REGION                          1..19
                                note = Synthetic Construct
MOD_RES                         1
                                note = ACETYLATION -
source                          1..19
                                mol_type = protein
                                organism = synthetic construct
SEQUENCE: 4
AADGYLPDWL EDTLSEGIR                                                           19

SEQ ID NO: 5                    moltype = AA  length = 8
FEATURE                         Location/Qualifiers
REGION                          1..8
                                note = Synthetic Construct
MOD_RES                         1
                                note = ACETYLATION -
source                          1..8
                                mol_type = protein
                                organism = synthetic construct
SEQUENCE: 5
ATGSGAPM                                                                        8

SEQ ID NO: 6                    moltype = AA  length = 13
FEATURE                         Location/Qualifiers
REGION                          1..13
                                note = Synthetic Construct
source                          1..13
                                mol_type = protein
                                organism = synthetic construct
SEQUENCE: 6
MAADGYLPDW LED                                                                 13

SEQ ID NO: 7                    moltype = DNA  length = 39
FEATURE                         Location/Qualifiers
misc_feature                    1..39
```

```
                        note = Synthetic Construct
source                  1..39
                        mol_type = other DNA
                        organism = synthetic construct
SEQUENCE: 7
gtggctgcag gcggtggcgc accaatggca gacaataac                              39

SEQ ID NO: 8            moltype = DNA  length = 78
FEATURE                 Location/Qualifiers
misc_feature            1..78
                        note = Synthetic Construct
source                  1..78
                        mol_type = other DNA
                        organism = synthetic construct
SEQUENCE: 8
cactccctct ctgcgcgctc gctcgctcac tgaggccggg cgaccaaagg tcgcccacgc        60
ccgggctttg cccgggcg                                                     78

SEQ ID NO: 9            moltype = AA  length = 10
FEATURE                 Location/Qualifiers
REGION                  1..10
                        note = Synthetic Construct
source                  1..10
                        mol_type = protein
                        organism = synthetic construct
SEQUENCE: 9
YLGPFNGLDK                                                              10

SEQ ID NO: 10           moltype = AA  length = 83
FEATURE                 Location/Qualifiers
REGION                  1..83
                        note = Synthetic Construct
source                  1..83
                        mol_type = protein
                        organism = synthetic construct
SEQUENCE: 10
EVTQNDGTTT IANNLTSTVQ VFTDSEYQLP YVLGSAHQGC LPPFPADVFM VPQYGYLTLN        60
NGSQAVGRSS FYCLEYFPSQ MLR                                               83

SEQ ID NO: 11           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 11
YNLNGR                                                                  6

SEQ ID NO: 12           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 12
YHLNGR                                                                  6

SEQ ID NO: 13           moltype = AA  length = 18
FEATURE                 Location/Qualifiers
REGION                  1..18
                        note = Synthetic Construct
source                  1..18
                        mol_type = protein
                        organism = synthetic construct
SEQUENCE: 13
SANVDFTVDN NGLYTEPR                                                     18

SEQ ID NO: 14           moltype = AA  length = 18
FEATURE                 Location/Qualifiers
REGION                  1..18
                        note = Synthetic Construct
source                  1..18
                        mol_type = protein
                        organism = synthetic construct
SEQUENCE: 14
SVNVDFTVDT NGVYSEPR                                                     18
```

```
SEQ ID NO: 15            moltype = AA  length = 15
FEATURE                  Location/Qualifiers
REGION                   1..15
                         note = Synthetic Construct
source                   1..15
                         mol_type = protein
                         organism = synthetic construct
SEQUENCE: 15
APGKKRPVEH SPVEP                                                          15

SEQ ID NO: 16            moltype = AA  length = 735
FEATURE                  Location/Qualifiers
source                   1..735
                         mol_type = protein
                         organism = Adeno-associated virus 2
SEQUENCE: 16
MAADGYLPDW LEDTLSEGIR QWWKLKPGPP PPKPAERHKD DSRGLVLPGY KYLGPFNGLD          60
KGEPVNEADA AALEHDKAYD RQLDSGDNPY LKYNHADAEF QERLKEDTSF GGNLGRAVFQ         120
AKKRVLEPLG LVEEPVKTAP GKKRPVEHSP VEPDSSSGTG KAGQQPARKR LNFGQTGDAD         180
SVPDPQPLGQ PPAAPSGLGT NTMATGSGAP MADNNEGADG VGNSSGNWHC DSTWMGDRVI         240
TTSTRTWALP TYNNHLYKQI SSQSGASNDN HYFGYSTPWG YFDFNRFHCH FSPRDWQRLI         300
NNNWGFRPKR LNFKLFNIQV KEVTQNDGTT TIANNLTSTV QVFTDSEYQL PYVLGSAHQG         360
CLPPFPADVF MVPQYGYLTL NNGSQAVGRS SFYCLEYFPS QMLRTGNNFT FSYTFEDVPF         420
HSSYAHSQSL DRLMNPLIDQ YLYYLSRTNT PSGTTTQSRL QFSQAGASDI RDQSRNWLPG         480
PCYRQQRVSK TSADNNNSEY SWTGATKYHL NGRDSLVNPG PAMASHKDDE EKFFPQSGVL         540
IFGKQGSEKT NVDIEKVMIT DEEEIRTTNP VATEQYGSVS TNLQRGNRQA ATADVNTQGV         600
LPGMVWQDRD VYLQGPIWAK IPHTDGHFHP SPLMGGFGLK HPPPQILIKN TPVPANPSTT         660
FSAAKFASFI TQYSTGQVSV EIEWELQKEN SKRWNPEIQY TSNYNKSVNV DFTVDTNGVY         720
SEPRPIGTRY LTRNL                                                         735

SEQ ID NO: 17            moltype = AA  length = 239
FEATURE                  Location/Qualifiers
REGION                   1..239
                         note = Synthetic Construct
source                   1..239
                         mol_type = protein
                         organism = synthetic construct
SEQUENCE: 17
MAADGYLPDW LEDNLSEGIR EWWDLKPGAP KPKANQQKQD DGRGLVLPGY KYLGPFNGLD          60
KGEPVNAADA AALEHDKAYD QQLKAGDNPY LRYNHADAEF QERLQEDTSF GGNLGRAVFQ         120
AKKRVLEPLG LVEEGAKTAP GKKRPVEPSP QRSPDSSTGI GKKGQQPAKK RLNFGQTGDS         180
ESVPDPQPIG EPPAGPSGLG SGTMAAGGGA PMADNNEGAD GVGSSSGNWH CDSTWLGDR         239

SEQ ID NO: 18            moltype = AA  length = 239
FEATURE                  Location/Qualifiers
REGION                   1..239
                         note = Synthetic Construct
source                   1..239
                         mol_type = protein
                         organism = synthetic construct
SEQUENCE: 18
MAADGYLPDW LEDNLSEGIR EWWDLKPGAP KPKANQQKQD DGRGLVLPGY KYLGPFNGLD          60
KGEPVNAADA AALEHDKAYD QQLKAGDNPY LRYNHADAEF QERLQEDTSF GGNLGRAVFQ         120
AKKRVLEPLG LVEEAAKTAP GKKRPVEPSP QRSPDSSTGI GKKGQQPAKK RLNFGQTGES         180
ESVPDPQPIG EPPAGPSGLG SGTMAAGGGA PMADNNEGAD GVGSSSGNWH CDSTWLGDR         239

SEQ ID NO: 19            moltype = AA  length = 239
FEATURE                  Location/Qualifiers
REGION                   1..239
                         note = Synthetic Construct
source                   1..239
                         mol_type = protein
                         organism = synthetic construct
SEQUENCE: 19
MAADGYLPDW LEDNLSEGIR EWWALKPGAP KPKANQQKQD DGRGLVLPGY KYLGPFNGLD          60
KGEPVNAADA AALEHDKAYD QQLQAGDNPY LRYNHADAEF QERLQEDTSF GGNLGRAVFQ         120
AKKRVLEPLG LVEEGAKTAP GKKRPVEPSP QRSPDSSTGI GKKGQQPARK RLNFGQTGDS         180
ESVPDPQPLG EPPAAPSGVG PNTMAAGGGA PMADNNEGAD GVGSSSGNWH CDSTWLGDR         239

SEQ ID NO: 20            moltype = AA  length = 239
FEATURE                  Location/Qualifiers
REGION                   1..239
                         note = Synthetic Construct
source                   1..239
                         mol_type = protein
                         organism = synthetic construct
SEQUENCE: 20
MAADGYLPDW LEDNLSEGIR EWWDLKPGAP KPKANQQKQD NGRGLVLPGY KYLGPFNGLD          60
KGEPVNAADA AALEHDKAYD QQLKAGDNPY LRYNHADAEF QERLQEDTSF GGNLGRAVFQ         120
```

```
AKKRVLEPLG LVEEGAKTAP AKKRPVEPSP QRSPDSSTGI GKKGQQPARK RLNFGQTGDS  180
ESVPDPQPLG EPPAAPSSVG SGTVAAGGGA PMADNNEGAD GVGNASGNWH CDSTWLGDR   239

SEQ ID NO: 21           moltype = AA  length = 238
FEATURE                 Location/Qualifiers
REGION                  1..238
                        note = Synthetic Construct
source                  1..238
                        mol_type = protein
                        organism = synthetic construct
SEQUENCE: 21
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDR    238

SEQ ID NO: 22           moltype = AA  length = 238
FEATURE                 Location/Qualifiers
REGION                  1..238
                        note = Synthetic Construct
source                  1..238
                        mol_type = protein
                        organism = synthetic construct
SEQUENCE: 22
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDR    238

SEQ ID NO: 23           moltype = AA  length = 238
FEATURE                 Location/Qualifiers
REGION                  1..238
                        note = Synthetic Construct
source                  1..238
                        mol_type = protein
                        organism = synthetic construct
SEQUENCE: 23
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDR    238

SEQ ID NO: 24           moltype = AA  length = 238
FEATURE                 Location/Qualifiers
REGION                  1..238
                        note = Synthetic Construct
source                  1..238
                        mol_type = protein
                        organism = synthetic construct
SEQUENCE: 24
MAADGYLPDW LEDNLSEGIR EWWALKPGVP QPKANQQHQD NRRGLVLPGY KYLGPGNGLD   60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDR    238

SEQ ID NO: 25           moltype = AA  length = 232
FEATURE                 Location/Qualifiers
REGION                  1..232
                        note = Synthetic Construct
source                  1..232
                        mol_type = protein
                        organism = synthetic construct
SEQUENCE: 25
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPLESPQ EPDSSSGIGK KGKQPARKRL NFEEDTGAGD  180
GPPEGSDTSA MSSDIEMRAA PGGNAVDAGQ GSDGVGNASG DWHCDSTWSE GK          232

SEQ ID NO: 26           moltype = AA  length = 241
FEATURE                 Location/Qualifiers
REGION                  1..241
                        note = Synthetic Construct
source                  1..241
                        mol_type = protein
                        organism = synthetic construct
SEQUENCE: 26
MAADGYLPDW LEDNLSEGIR EWWALKPGAP QPKANQQHQD NGRGLVLPGY KYLGPFNGLD   60
KGEPVNEADA AALEHDKAYD KQLEQGDNPY LKYNHADAEF QQRLATDTSF GGNLGRAVFQ  120
AKKRILEPLG LVEEGVKTAP GKKRPLEKTP NRPTNPDSGK APAKKKQKDG EPADSARRTL  180
```

```
DFEDSGAGDG PPEGSSSGEM SHDAEMRAAP GGNAVEAGQG ADGVGNASGD WHCDSTWSEG    240
R                                                                   241

SEQ ID NO: 27           moltype = AA  length = 232
FEATURE                 Location/Qualifiers
REGION                  1..232
                        note = Synthetic Construct
source                  1..232
                        mol_type = protein
                        organism = synthetic construct
SEQUENCE: 27
MTDGYLPDWL EDNLSEGVRE WWALQPGAPK PKANQQHQDN ARGLVLPGYK YLGPGNGLDK    60
GEPVNAADAA ALEHDKAYDQ QLKAGDNPYL KYNHADAEFQ QRLQGDTSFG GNLGRAVFQA    120
KKRVLEPLGL VEQAGETAPG KKRPLIESPQ QPDSSTGIGK KGKQPAKKKL VFEDETGAGD    180
GPPEGSTSGA MSDDSEMRAA GGAAVEGGQ GADGVGNASG DWHCDSTWSE GH            232

SEQ ID NO: 28           moltype = AA  length = 228
FEATURE                 Location/Qualifiers
REGION                  1..228
                        note = Synthetic Construct
source                  1..228
                        mol_type = protein
                        organism = synthetic construct
SEQUENCE: 28
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGGP LGDNNQGADG VGNASGDWHC DSTWMGDR                228

SEQ ID NO: 29           moltype = AA  length = 238
FEATURE                 Location/Qualifiers
REGION                  1..238
                        note = Synthetic Construct
source                  1..238
                        mol_type = protein
                        organism = synthetic construct
SEQUENCE: 29
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDR     238

SEQ ID NO: 30           moltype = AA  length = 246
FEATURE                 Location/Qualifiers
REGION                  1..246
                        note = Synthetic Construct
source                  1..246
                        mol_type = protein
                        organism = synthetic construct
SEQUENCE: 30
MAADGYLPDW LEDNLSEGIR EWWXLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ    120
AKKRVLEPLG LVEEGAKTAP GKKRPVEXSP XXQXXPDSSS GIGKKGQXXX XXQPAKKRLN    180
FGQTGDSESV PDPQPLGEPP AAPSGLGXXT MAAGGGAPMA DNNEGADGVG NASGNWHCDS    240
TWLGDR                                                              246

SEQ ID NO: 31           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 31
MAADGYLPDW LEDNLSEGIR EWWDLKPGAP KPKANQQKQD DGRGLVLPGY KYLGPFNGLD    60
K                                                                   61

SEQ ID NO: 32           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 32
MAADGYLPDW LEDNLSEGIR EWWALKPGAP KPKANQQKQD DGRGLVLPGY KYLGPFNGLD    60
K                                                                   61

SEQ ID NO: 33           moltype = AA  length = 61
```

```
FEATURE                 Location/Qualifiers
REGION                  1..61
                        note = Synthetic Construct
source                  1..61
                        mol_type = protein
                        organism = synthetic construct
SEQUENCE: 33
MAADGYLPDW LEDNLSEGIR EWWDLKPGAP KPKANQQKQD NGRGLVLPGY KYLGPFNGLD    60
K                                                                   61

SEQ ID NO: 34           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 34
MAADGYLPDW LEDTLSEGIR QWWKLKPGPP PPKPAERHKD DSRGLVLPGY KYLGPFNGLD    60
K                                                                   61

SEQ ID NO: 35           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 35
MAADGYLPDW LEDNLSEGIR EWWALKPGVP QPKANQQHQD NRRGLVLPGY KYLGPGNGLD    60
K                                                                   61

SEQ ID NO: 36           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 36
MAADGYLPDW LEDNLSEGIR EWWALKPGAP QPKKANQQHQ DNGRGLVLPG KYLGPFNGLD    60
K                                                                   61

SEQ ID NO: 37           moltype = AA  length = 60
FEATURE                 Location/Qualifiers
REGION                  1..60
                        note = Synthetic Construct
source                  1..60
                        mol_type = protein
                        organism = synthetic construct
SEQUENCE: 37
MTDGYLPDWL EDNLSEGVRE WWALQPGAPK PKANQQHQDN ARGLVLPGYK YLGPGNGLDK    60

SEQ ID NO: 38           moltype = AA  length = 60
FEATURE                 Location/Qualifiers
REGION                  1..60
                        note = Synthetic Construct
source                  1..60
                        mol_type = protein
                        organism = synthetic construct
SEQUENCE: 38
MSFVDHPPDW LEEVGEGLRE FLGLEAGPPK PKPNQHQDQ ARGLVLPGYN YLGPGNGLDR     60

SEQ ID NO: 39           moltype = AA  length = 61
FEATURE                 Location/Qualifiers
REGION                  1..61
                        note = Synthetic Construct
source                  1..61
                        mol_type = protein
                        organism = synthetic construct
SEQUENCE: 39
MAADGYLPDW LEDNLSEGIR EWWALKPGAP QPKANQQHQD NARGLVLPGY KYLGPGNGLD    60
K                                                                   61

SEQ ID NO: 40           moltype = AA  length = 61
FEATURE                 Location/Qualifiers
REGION                  1..61
                        note = Synthetic Construct
source                  1..61
```

-continued

```
                    mol_type = protein
                    organism = synthetic construct
SEQUENCE: 40
MAADGYLPDW LEDNLSEGIR EWWXLKPGAP KPKANQQKQD DGRGLVLPGY KYLGPFNGLD    60
K                                                                  61
```

What is claimed is:

1. A method of analyzing a preparation of AAV particles, the method comprising
 a) denaturing the AAV particles,
 b) subjecting the denatured AAV particles to liquid chromatography/mass spectroscopy (LC/MS) intact protein analysis, and
 c) determining the masses of one or more viral proteins (VPs) of the particles in the preparation,
 wherein the method is performed in the absence of a gel separation step.

2. The method of claim 1, wherein the VPs comprise VP1, VP2, and VP3 capsid proteins and one more variants of VP1, VP2, or VP3 capsid proteins.

3. The method of claim 1, wherein the AAV particles are denatured with acetic acid, guanidine hydrochloride and/or an organic solvent.

4. The method of claim 1, wherein the liquid chromatography is reverse phase liquid chromatography, size exclusion chromatography, hydrophilic interaction liquid chromatography, or cation exchange chromatography.

5. The method of claim 1, wherein the liquid chromatography is reverse phase liquid chromatography.

6. The method of claim 5, wherein the reverse phase chromatography is performed with a C4 column.

7. The method of claim 1, wherein the liquid chromatography is ultra-performance liquid chromatography (UPLC).

8. The method of claim 1, wherein the mass spectrometry comprises assisted calibration.

9. The method of claim 8, wherein sodium iodide is used as a calibrant.

10. A method of determining post-translational modifications of viral proteins (VPs) in a preparation of viral particles, the method comprising
 a) denaturing the viral particles,
 b) subjecting the denatured viral particles to liquid chromatography/mass spectroscopy (LC/MS) intact protein analysis, and
 c) determining the masses of one or more VPs of the viral particles
 wherein a deviation of one or more of the masses of the one or more VPs from the theoretical masses of VPs that have not undergone post-translational modifications is indicative of post-translational modifications of the VPs,
 and wherein the method is performed in the absence of a gel separation step.

11. The method of claim 10, wherein the liquid chromatography is reverse phase liquid chromatography, size exclusion chromatography, hydrophilic interaction liquid chromatography, or cation exchange chromatography.

12. The method of claim 10, wherein the viral particles comprise a viral vector encoding a heterologous transgene.

13. The method of claim 10, wherein the liquid chromatography is reverse phase chromatography.

14. The method of claim 13, wherein the reverse phase chromatography is a C4 or C8 reverse chromatography.

15. The method of claim 10, wherein the liquid chromatography is ultra-performance liquid chromatography (UPLC).

16. The method of claim 10, wherein the mass spectrometry comprises assisted calibration.

17. The method of claim 16, wherein sodium iodide is used as a calibrant.

18. A method of determining the extent of deamidation of viral proteins (VPs) in a preparation of viral particles, the method comprising
 a) denaturing the viral particles,
 b) subjecting the denatured viral particles to liquid chromatography/mass spectrometry/mass spectrometry (LC/MS/MS) intact protein analysis, and
 c) determining the percentage of deamidated VPs in the preparation,
 wherein the method is performed in the absence of a gel separation step.

19. The method of claim 18, wherein the liquid chromatography is reverse phase chromatography, wherein the reverse phase chromatography is performed with a C4 column.

20. The method of claim 18, wherein the liquid chromatography is reverse phase chromatography, wherein the reverse phase chromatography is performed with a C8 column.

21. The method of claim 2, wherein the one more variants of VP1, VP2, or VP3 capsid proteins comprise one or more post-translational modifications, wherein the method comprises determining the masses of the VP1, VP2, and VP3 capsid proteins and the one more variants of VP1, VP2, or VP3 capsid proteins, and wherein a deviation of one or more of the masses of the variants of VP1, VP2, or VP3 capsid proteins from the theoretical masses of VP1, VP2, and VP3 capsid proteins that have not undergone post-translational modifications is indicative of post-translational modifications of the variants of VP1, VP2, or VP3 capsid proteins.

* * * * *

UNITED STATES PATENT AND TRADEMARK OFFICE
CERTIFICATE OF CORRECTION

PATENT NO. : 12,123,880 B2
APPLICATION NO. : 18/321542
DATED : October 22, 2024
INVENTOR(S) : Xiaoying Jin et al.

It is certified that error appears in the above-identified patent and that said Letters Patent is hereby corrected as shown below:

In the Claims

At Column 83, Claim 1, Line number 14, please replace "spectroscopy" with -- spectrometry --; and
At Column 83, Claim 10, Line number 46, please replace "spectroscopy" with -- spectrometry --.

Signed and Sealed this
Nineteenth Day of November, 2024

Katherine Kelly Vidal
*Director of the United States Patent and Trademark Office*